US008883817B2

(12) United States Patent
Sadée et al.

(10) Patent No.: US 8,883,817 B2
(45) Date of Patent: Nov. 11, 2014

(54) COMBINATION ANALGESIC EMPLOYING OPIOID AND NEUTRAL ANTAGONIST

(75) Inventors: Wolfgang Sadée, Upper Arlington, OH (US); Edward Bilsky, Biddeford, ME (US); Janet Yancey-Wrona, Freeport, ME (US)

(73) Assignee: AIKO Biotechnology, Portland, ME (US)

( * ) Notice: Subject to any disclaimer, the term of this patent is extended or adjusted under 35 U.S.C. 154(b) by 943 days.

(21) Appl. No.: 12/288,347

(22) Filed: Oct. 17, 2008

(65) Prior Publication Data

US 2009/0111844 A1    Apr. 30, 2009

Related U.S. Application Data

(60) Provisional application No. 60/981,034, filed on Oct. 18, 2007.

(51) Int. Cl.
*A61K 31/485* (2006.01)
*A61K 31/137* (2006.01)
*A61K 45/06* (2006.01)

(52) U.S. Cl.
CPC ............. *A61K 45/06* (2013.01); *A61K 31/485* (2013.01)
USPC ........................................ 514/282

(58) Field of Classification Search
USPC ........................................ 514/282
See application file for complete search history.

(56) References Cited

U.S. PATENT DOCUMENTS

| | | | |
|---|---|---|---|
| 3,523,906 A | 8/1970 | Vrancken et al. | 252/316 |
| 3,691,090 A | 9/1972 | Kitajima et al. | 252/316 |
| 3,737,337 A | 6/1973 | Schnoring et al. | 117/100 |
| 3,891,570 A | 6/1975 | Fukushima et al. | 252/316 |
| 3,960,757 A | 6/1976 | Morishita et al. | 252/316 |
| 4,175,119 A | 11/1979 | Porter | 424/10 |
| 4,176,186 A | 11/1979 | Goldberg et al. | 424/260 |
| 4,389,330 A | 6/1983 | Tice et al. | 427/213.36 |
| 4,457,933 A | 7/1984 | Gordon et al. | 424/260 |
| 4,459,278 A | 7/1984 | Porter | 424/10 |
| 4,719,215 A | 1/1988 | Goldberg | 514/282 |
| 4,760,069 A | 7/1988 | Rzeszotarski et al. | 514/282 |
| 4,861,781 A | 8/1989 | Goldberg | 514/282 |
| 5,019,400 A | 5/1991 | Gombotz et al. | 424/497 |
| 5,472,943 A | 12/1995 | Crain et al. | 514/12 |
| 5,512,578 A | 4/1996 | Crain et al. | 514/282 |
| 5,580,876 A | 12/1996 | Crain et al. | 514/282 |
| 5,650,173 A | 7/1997 | Ramstack et al. | 424/489 |
| 5,656,297 A | 8/1997 | Bernstein et al. | 424/484 |
| 5,767,125 A | 6/1998 | Crain et al. | 514/282 |
| 5,780,479 A | 7/1998 | Kim | 514/282 |
| 5,792,477 A | 8/1998 | Rickey et al. | 424/501 |
| 5,811,451 A | 9/1998 | Minoia et al. | 514/443 |
| 5,852,032 A | 12/1998 | Mason | 514/282 |
| 5,916,598 A | 6/1999 | Rickey et al. | 424/501 |
| 5,922,253 A | 7/1999 | Herbert et al. | 264/5 |
| 5,972,954 A | 10/1999 | Foss et al. | 514/282 |
| 6,004,970 A | 12/1999 | O'Malley et al. | 514/282 |
| 6,054,127 A | 4/2000 | Swain et al. | 424/194.1 |
| 6,110,503 A | 8/2000 | Rickey et al. | 424/501 |
| 6,136,817 A | 10/2000 | Schmidhammer | 514/279 |
| 6,194,006 B1 | 2/2001 | Lyons et al. | 424/489 |
| 6,228,863 B1 | 5/2001 | Palermo et al. | 514/282 |
| 6,271,240 B1 | 8/2001 | Simon | 514/282 |
| 6,274,591 B1 | 8/2001 | Foss et al. | 514/282 |
| 6,277,384 B1 | 8/2001 | Kaiko et al. | 424/400 |
| 6,306,425 B1 | 10/2001 | Tice et al. | 424/426 |
| 6,362,194 B1 | 3/2002 | Crain et al. | 514/285 |
| 6,375,957 B1 | 4/2002 | Kaiko et al. | 424/400 |
| 6,419,959 B1 | 7/2002 | Walter et al. | 424/490 |
| 6,451,806 B2 | 9/2002 | Farrar | 514/282 |
| 6,455,537 B1 | 9/2002 | Cooper | 514/289 |
| 6,469,030 B2 | 10/2002 | Farrar et al. | 514/331 |
| 6,475,494 B2 | 11/2002 | Kaiko et al. | 424/400 |
| 6,525,062 B2 | 2/2003 | Levine | 514/282 |
| 6,528,271 B1 | 3/2003 | Bohn et al. | 435/7.2 |
| 6,559,158 B1 | 5/2003 | Foss et al. | 514/282 |
| 6,559,159 B2 | 5/2003 | Carroll et al. | 514/282 |
| 6,569,866 B2 | 5/2003 | Simon | 514/282 |
| 6,593,367 B1 | 7/2003 | Dewey et al. | 514/561 |
| 6,608,075 B2 | 8/2003 | Foss et al. | 514/282 |
| 6,627,635 B2 | 9/2003 | Palermo et al. | 514/282 |
| 6,696,066 B2 | 2/2004 | Kaiko et al. | 424/400 |
| 6,713,488 B2 | 3/2004 | Sadée et al. | 514/282 |
| 6,716,449 B2 | 4/2004 | Oshlack et al. | 424/449 |
| 6,734,188 B1 | 5/2004 | Rhodes et al. | 514/282 |
| 6,790,854 B2 | 9/2004 | Tsushima et al. | 514/278 |
| 6,794,510 B2 | 9/2004 | Le Bourdonnec et al. | 546/192 |
| 6,825,205 B2 | 11/2004 | Kyle | 514/282 |

(Continued)

FOREIGN PATENT DOCUMENTS

| EP | 1 479 381 A1 | 11/2004 |
|---|---|---|
| EP | 1263438 | 5/2006 |

(Continued)

OTHER PUBLICATIONS www.clinicaltrials.gov, *A Phase 2, Double-Blind, Multiple-Dose Escalation Study to Evaluate NKTR-118 (Oral PEG-Naloxol) in Patients with Opioid-Induced Constipation (OIC)*, Sep. 27, 2009, 3 pages.

(Continued)

*Primary Examiner* — Shirley V Gembeh

(74) *Attorney, Agent, or Firm* — Sunstein Kann Murphy & Timbers LLP

(57) ABSTRACT

A non-addictive analgesic co-formulation comprising an opioid agonist in an amount sufficient to confer analgesia in a mammalian subject and a neutral opioid antagonist in an amount sufficient to inhibit peripheral effects, and insufficient to block substantial central effects, of the opioid agonist in the subject. Such formulations, and methods of using same, may also deter diversion, inhibit peripheral effects, and reduce addiction liability.

28 Claims, 31 Drawing Sheets

(56) References Cited

U.S. PATENT DOCUMENTS

| | | | |
|---|---|---|---|
| 6,919,350 B2 | 7/2005 | Chang et al. | 514/282 |
| 6,992,090 B2 | 1/2006 | Le Bourdonnec et al. | 514/317 |
| 7,008,939 B2 | 3/2006 | Christoph | 514/212.01 |
| 7,026,329 B2 | 4/2006 | Crain et al. | 514/285 |
| 7,034,036 B2 | 4/2006 | Schoenhard | 514/282 |
| 7,041,320 B1 | 5/2006 | Nuwayser | 424/497 |
| 7,056,500 B2 | 6/2006 | Bentley et al. | 424/78.18 |
| 7,091,354 B2 | 8/2006 | Le Bourdonnec et al. | 546/236 |
| 7,144,587 B2 | 12/2006 | Oshlack et al. | 424/490 |
| 7,172,767 B2 | 2/2007 | Kaiko et al. | 424/468 |
| 7,196,100 B2 | 3/2007 | Benesh et al. | 514/318 |
| 7,201,920 B2 | 4/2007 | Kumar et al. | 424/454 |
| 2001/0049375 A1 | 12/2001 | Sadée et al. | 514/282 |
| 2003/0187010 A1 | 10/2003 | Foss et al. | 514/282 |
| 2003/0191147 A1 | 10/2003 | Sherman et al. | 514/282 |
| 2003/0211157 A1 | 11/2003 | Simon | 424/486 |
| 2004/0024006 A1 | 2/2004 | Simon | 514/282 |
| 2004/0162308 A1 | 8/2004 | Foss et al. | 514/282 |
| 2004/0167147 A1 | 8/2004 | Foss et al. | 514/282 |
| 2004/0167148 A1 | 8/2004 | Foss et al. | 514/282 |
| 2004/0180916 A1 | 9/2004 | Levine | 514/282 |
| 2004/0254208 A1 | 12/2004 | Weber et al. | 514/282 |
| 2005/0038062 A1 | 2/2005 | Burns et al. | 514/282 |
| 2005/0165038 A1 | 7/2005 | Gordon | 514/282 |
| 2006/0069086 A1 | 3/2006 | Michalow | 514/220 |
| 2006/0111382 A1 | 5/2006 | Shafer et al. | 514/282 |
| 2006/0235038 A1 | 10/2006 | Simon | 514/282 |
| 2007/0099947 A1 | 5/2007 | Dean et al. | 514/282 |
| 2007/0105863 A1 | 5/2007 | Dolle et al. | 514/249 |
| 2007/0197573 A1 | 8/2007 | Sadée et al. | 514/282 |
| 2009/0111844 A1 | 4/2009 | Sadée et al. | 514/282 |

FOREIGN PATENT DOCUMENTS

| | | |
|---|---|---|
| WO | WO 96/37775 | 11/1996 |
| WO | WO 01/68080 | 9/2001 |
| WO | WO 2004/050020 | 6/2004 |
| WO | WO 2007/016108 | 2/2007 |

OTHER PUBLICATIONS

M.C. Holden Ko, et al., *Differential in Vivo Potencies of Naltrexone and 6B-Naltrexol in the Monkey*, The Journal of Pharmacology and Experimental Therapeutics, vol. 316, No. 2, 2006, pp. 772-779.

L. M. Sayre et al. (Abstract only), *Importance of C-6 chirality in conferring irreversible opioid antagonism to naltrexone-derived affinity labels*, NCBI, Sep. 26, 1983, 2 pages.

Anna Ferari, et al. *Serum time course of naltrexone and 6B-naltrexol levels during long term treatment in drug addicts*, ScienceDirect, 1998, 2 pages.

Sadée, et al., "Basal Opioid Receptor Activity, Neutral Antagonists, and Therapeutic Opportunities," *Life Sciences*, vol. 76, No. 13, Feb. 11, 2005, pp. 1427-1437.

Wang, et al., "Inverse Agonists and Neutral Antagonists at μ Opioid Receptor (MOR): Possible Role of Basal Receptor Signaling in Narcotic Dependence," *Journal of Neurochemistry*, vol. 77, No. 6, Jun. 2001, pp. 1590-1600.

European Patent Office, Jeans Arribrosch, Authorized Officer, Partial International Search Report dated Jun. 10, 2009; Application No. PCT/US2008/011915; 17 pages.

Haider, Ursula, Authorized Officer, *The International Search Report and the Written Opinion of the International Searching Authority*, International Application No. PCT/US2008/011915, International Searching Authority, Sep. 30, 2009, 34 pages.

Marczak, et al., "[N-Allyl-Dmtl]-endomorphins are μ-opioid receptor antagonists lacking inverse agonist properties," *J. Pharmacol. Exp. Ther. Fast Forward* (Jul. 12, 2007).

Wang, et al., "Basal signaling activity of mu opioid receptor in mouse brain: role in narcotic dependence," *J Pharmacol Exp Ther*.; 308(2):512-20 (Feb. 2004 Epub Nov. 4, 2003).

Raehal, et al., "In vivo characterization of 6β-naltrexol, an opioid ligand with less inverse agonist activity compared with naltrexone and naloxone in opioid-dependent mice," *J Pharmacol Exp Ther* 313(3):1150-62). (Jun. 2005; Epub Feb. 16, 2005).

Bilsky, et al., "Antinociceptive activity of [beta-methyl-2',6'-dimethyltyrosine(1)]-substituted cyclic [D-Pen(2), DPen(5)]Enkephalin and [D-Ala(2), Asp(4)]Deltorphin analogs," *J Pharmacol Exp Ther*; 293(1): 151-8, 1999.

Cone, et al., "The Urinary Excretion Profile of Naltrexone and Metabolites in Man," *Drug Metab and Disp* 2(6): 506-512 (1974).

Wall, et al., "Metabolism and Disposition of Naltrexone in Man after Oral and Intravenous Administration, Drug Metabolism and Disposition" *Drug Metabolism and Disposition*, 9(4):369-375 (1981).

Verebey K., "The Clinical Pharmacology of Naltrexone: Pharmacology and Pharmacodynamics," *Naltrexone: NIDA Research Monograph*, 28, R E Willette and G Barnett, eds. pp. 147-158 (1980).

Wall, et al., "The Metabolism of Naltrexone in Man," *Naltrexone: NIDA Research Monograph*, 28, R E Willette and G Barnett, eds. pp. 105-131 (1980).

Perez-Reyes, et al., "A Comparative Study of the Oral, Intravenous, and Subcutaneous Administration f 3 h-Naltrexone to normal male volunteers," *Naltrexone: NIDA Research Monograph* 28, R E Willette and G Barnett, eds. pp. 93-101) (1980).

Dunbar, et al., "Single- and Multiple-Dose Pharmacokinetics of Long-acting Injectable Naltrexone," *Alcohol: Clin and Exper Res.* 30(3):480-490 (2006).

Jayaram-Lindstrom, et al., "An open clinical trial of naltrexone for amphetamine dependence: Compliance and tolerability," *Nord J Pschy* 59(3):167-171 (2005).

Brewer, et al., "Case Report. Naltrexone: report of lack of hepatotoxicity in acute viral hepatitis, with a review of the literature," *Addict Bio* 9, 81-87) (2004).

Chatterjie, et al., "Sterospecific synthesis of the 6β-Hydroxy Metabolites of Naltrexone and Naloxone," *J. Med. Chem.*, 18, pp. 490-492 (1975).

Jiang, et al., *J. Med. Chem.* 20, pp. 1100-1102 (1977).

Plapp, B.V., "Control of Alcholo Metabolism," pp. 311-322 *Towards a Molecular Basis of Alcohol Use and Abuse*, eds. Janssen et al., Birkhaeuser Verlag, 1994.

Yancey-Wrona, et al., "6β-Naltrexol Prefrentially Antagonizes Opioid Effects on Gastrointestinal Transit Compared to Antinociception in Mice" *Life Sciences* 85 (2009) 413-20.

European Patent Office, Summons to Attend Oral Proceedings pursuant to Rule 115(1) EPC—International Application No. 08839342.6—1216, dated Jan. 5, 2012 (16 pages).

COMBINATION ANALGESIC EMPLOYING OPIOID AND NEUTRAL ANTAGONIST

CROSS REFERENCE TO RELATED APPLICATIONS

This application claims priority from U.S. Provisional Application Ser. No. 60/981,034, filed in the United States Patent and Trademark Office on Oct. 18, 2007, which is hereby incorporated by reference herein.

TECHNICAL FIELD

The present invention relates to co-formulations of opioid agonists and opioid antagonists, and in particular to such co-formulations using neutral antagonists.

BACKGROUND ART

Opioid agonists, while creating analgesia in humans and other mammalian subjects, typically are addictive and also typically have serious adverse side effects, including constipation and nausea. To address the addictive qualities of opioid agonists, the prior art teaches the use of co-formulations that include both opioid agonists and opioid antagonists. Most prior art co-formulations utilize opioid antagonists such as naltrexone or naloxone, which themselves have aversive effects in human and mammalian subjects. In fact, these compounds can trigger severe, and sometimes life-threatening, withdrawal symptoms. Such opioid antagonists are referred to in the present application as "aversive." U.S. Pat. No. 6,627,635 to Palermo et al. and U.S. Pat. Nos. 6,696,066, 6,475,494 and 6,375,957 to Kaiko et al. provide examples of co-formulations that employ aversive opioid antagonists. Recent research by Marczak et al. emphasizes the aversive effects of both naltrexone and naloxone in opioid-dependent subjects. Marczak E., Jinsmaa Y., Li T., Bryant S. D., Tsuda Y., Okada Y., Lazaraus L. H. (Jul. 12, 2007) "[N-Allyl-Dmt1]-endomorphins are μ-opioid receptor antagonists lacking inverse agonist properties," *J. Pharmacol. Exp. Ther. Fast Forward.*

U.S. Pat. No. 6,713,488 B2 to Wolfgang Sadée et al., which is hereby incorporated herein by reference and is hereinafter referred to as "Sadée," teaches the use of "neutral" opioid antagonists, which do not have aversive effects, to treat opioid agonist addiction. Sadée identifies as neutral antagonists certain naltrexone and naloxone analogs, including 6β-naltrexol and 6β-naltrexamide. Sadée also teaches that neutral antagonists can be used to treat other side-effects of opioid agonists, including constipation and respiratory depression.

Building on Sadée's research, United States Patent Application 2004/0024006 A1 to David Lew Simon, hereinafter referred to as "Simon," proposes non-addictive opioid agonist/antagonist co-formulations that include neutral opioid antagonists such as 6β-naltrexol. Simon's disclosure is prophetic in nature, however, and lacks supporting, experimental data. For example, paragraphs [0107] and [108] of Simon discuss a known effective dosage of morphine (0.15) mg/kg body weight) and then suggest a completely unknown and untested range of possible doses for 6β-naltrexol from 0.00026-0.0015 mg/kg is body weight, providing no data for such a formulation ever being effective. Similarly, in paragraph [0155] of Simon's application, Simon uses data provided by Kaiko in the U.S. Pat. No. 6,475,494 to propose that 0.5 to 12 mg of 6β-naltrexol be administered per 15 mg hydrocodone. These ratios of naltrexol to opioid range from 0.03:1 (i.e. 15.5-fold less naltrexol than opioid) to nearly a 1:1 ratio of naltrexol to opioid. Given the complete lack of supporting data, these suggested dosages are uninformative and effectively meaningless, representing mere guesses. Further, Kaiko teaches the use of antagonists that have aversive effects in humans and precipitate severe withdrawal symptoms. Simon extrapolates to propose a dosage chart in paragraph [0156] for other kinds of opioid agonists.

SUMMARY OF THE INVENTION

The present invention teaches the use of an opioid/opioid antagonist co-formulation, co-administration of the agonist with the antagonist, or separate but overlapping administration of the agonist with the neutral antagonist, wherein such co-formulation, co-administration or separate administration is uniquely designed to address both addiction liability of the opioid and peripheral side effects, such as constipation.

In a first embodiment of the invention there is provided a unit dosage of an analgesic composition comprising an opioid agonist in an amount sufficient to confer analgesia in a mammalian subject and a neutral opioid antagonist in an amount sufficient to inhibit peripheral effects, and insufficient to block substantial central effects, of the opioid agonist in the subject.

In a related embodiment of the invention the analgesic composition comprises an opioid agonist, which is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, noroxycodone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine and tramadol, in an amount sufficient to confer analgesia in a mammalian subject. In addition, the neutral opioid antagonist may be a naloxone or naltrexone analog showing neutral nonaversive properties.

Naltrexone analogs may be represented by formula Iα or Iβ, including pharmaceutically acceptable salts thereof:

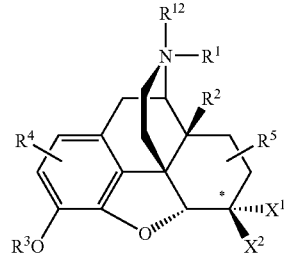

(Iα)

-continued

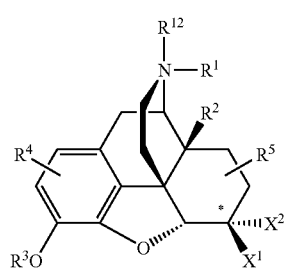

(Iβ)

wherein:
R$^1$ is cycloalkyl(alkyl), for example, C$_3$-C$_7$ (cycloalkyl) alkyl, for example, C$_3$-C$_7$ (cycloalkyl)methyl such as (cyclopropyl)methyl or C$_5$-C$_7$ (cycloalkenyl)alkyl;
R$^2$ is H, OH or esters thereof, such as —OAc(O$_2$C(alkyl)), for example O$_2$(C$_1$-C$_6$ alkyl);
R$^3$ is H, alkyl for example, C$_1$-C$_6$ alkyl, or (alkyl)C═O for example, ((C$_1$-C$_6$)alkyl)-C═O;
R$^4$ and R$^5$ are independently H, halogen (F, Cl, Br or I), alkyl, for example C$_1$-C$_6$ alkyl, alkoxy, such as C$_1$-C$_4$ alkoxy, nitro, amino, cyano, carboxyl or acyl which may be substituted for one or more hydrogens on the ring;
X$^1$ and X$^2$ are the same or different, and may be H, C$_1$-C$_6$ alkyl, —OR$^6$, —NR$^7$R$^8$R$^9$, —NCOR$^{10}$, —NO$_2$, or —SR$^{11}$, wherein,
R$^6$ and R$^{11}$ are independently H, alkyl, for example C$_1$-C$_6$ alkyl, substituted alkyl, cycloalkyl, for example C$_3$-C$_7$ cycloalkyl, substituted cycloalkyl, aryl, for example phenyl, naphthyl, imidazole, quinoline, isoquinoline, oxazole, benzoxazole, thiazole, pyrimidyl, pyrazolyl, indole, substituted aryl, acyl, for example C$_1$-C$_n$ acyl such as —C(O)C$_1$-C$_6$ alkyl wherein n is typically 6-10 but may be 10-20 or greater, aroyl, for example benzoyl, naphthoyl, imidazoyl, quinolinoyl, isoquinolinoyl, oxazoyl, benzoxazoyl, thiazoyl, indoyl, and pyrimidoyl, polyethyleneglycyl (PEGyl), or other similar substitutions such as polyether groups;
R$^7$, R$^8$ and R$^{10}$ are independently hydrogen, alkyl, for example C$_1$-C$_6$ alkyl, substituted alkyl, cycloalkyl for example C$_3$-C$_7$ cycloalkyl, substituted cycloalkyl, aryl, substituted aryl;
R$^9$ and R$^{12}$ can be present or absent and are independently hydrogen, alkyl, for example C$_1$-C$_6$ alkyl, substituted alkyl, cycloalkyl for example C$_3$-C$_7$ cycloalkyl, substituted cycloalkyl, aryl, for example phenyl, naphthyl, imidazole, quinoline, isoquinoline, oxazole, benzoxazole, thiazole, pyrimidyl, pyrazolyl, indole, substituted aryl;
and pharmaceutically acceptable salts thereof.

Naloxone analogs may be represented by formula Iα or Iβ, including pharmaceutically acceptable salts thereof:

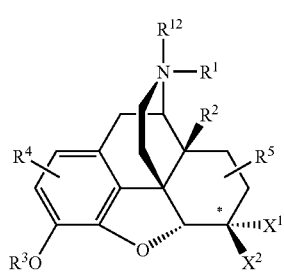

(Iα)

-continued

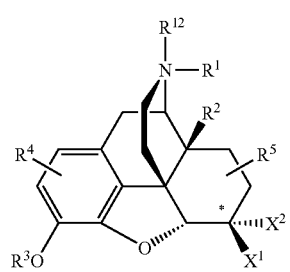

(Iβ)

wherein:
R$^1$ is alkenyl, for example C$_3$-C$_6$ alkenyl, such as allyl;
R$^2$ is H, OH or esters thereof, such as —OAc(O$_2$C(alkyl)), for example O$_2$(C$_1$-C$_6$ alkyl);
R$^3$ is H, alkyl for example, C$_1$-C$_6$ alkyl, or (alkyl)C═O for example, ((C$_1$-C$_6$)alkyl)-C═O;
R$^4$ and R$^5$ are independently H, halogen (F, Cl, Br or I), alkyl, for example C$_1$-C$_6$ alkyl, alkoxy, such as C$_1$-C$_4$ alkoxy, nitro, amino, cyano, carboxyl or acyl which may be substituted for one or more hydrogens on the ring;
X$^1$ and X$^2$ are the same or different, and may be H, alkyl, —OR$^6$, —NR$^7$R$^8$R$^9$, —NCOR$^{10}$, —NO$_2$, or —SR$^{11}$, wherein,
R$^6$ and R$^{11}$ are independently H, alkyl, for example C$_1$-C$_6$ alkyl, substituted alkyl, cycloalkyl, for example C$_3$-C$_7$ cycloalkyl, substituted cycloalkyl, aryl, for example phenyl, naphthyl, imidazole, quinoline, isoquinoline, oxazole, benzoxazole, thiazole, pyrimidyl, pyrazolyl, indole, substituted aryl, acyl, for example C$_1$-C$_n$ acyl such as —C(O)—C$_1$-C$_6$ alkyl wherein n is typically 6-10 but may be 10-20 or greater, aroyl, for example benzoyl, naphthoyl, imidazoyl, quinolinoyl, isoquinolinoyl, oxazoyl, benzoxazoyl, thiazoyl, indoyl, and pyrimidoyl, polyethyleneglycyl (PEGyl), or other similar substitutions such as polyether groups;
R$^7$, R$^8$ and R$^{10}$ are independently hydrogen, alkyl, for example C$_1$-C$_6$ alkyl substituted alkyl, cycloalkyl for example C$_3$-C$_7$ cycloalkyl, substituted cycloalkyl, aryl, substituted aryl;
R$^9$ and R$^{12}$ can be present or absent and are independently hydrogen, alkyl, for example C$_1$-C$_6$ alkyl, substituted alkyl, cycloalkyl for example C$_3$-C$_7$ cycloalkyl, substituted cycloalkyl, aryl, for example phenyl, naphthyl, imidazole, quinoline, isoquinoline, oxazole, benzoxazole, thiazole, pyrimidyl, pyrazolyl, indole, substituted aryl;
and pharmaceutically acceptable salts thereof.

For generic formulae I α and Iβ, when X$^1$ and X$^2$ are the same, the stereocenter at this position, marked by an asterisk, goes away.

In related embodiments, the naloxone or naltrexone analog may be, including 6β-naltrexol, 6β-naltrexamide, 6β-naloxol, 6α-naltrexol, 6α-naloxol, 6α-naltrexamine, 6-deoxynaltrexone, 6β-naltrexamine, and 6α-naltrexamide, pharmaceutically acceptable physical isomorphs thereof, and pharmaceutically acceptable salts thereof.

In a further related embodiment of the invention described above, the mammalian subject is a human.

In another related embodiment of the invention described above, the analgesic composition is for oral or intravenous administration and the neutral opioid antagonist is 6β-naltrexol. Dosage ranges for the neutral antagonist relative to the analgesic, in separate formulations for co-administration, may range from a dosage of approximately 0.0008-0.08 mg of 6β-naltrexol per kg of body weight of the subject for i.v. administration of both the antagonist and agonist, and from a dosage range of approximately 0.008-0.24 mg 6β-naltrexol per kg of body weight for oral administration of both the antagonist and agonist, and from a dosage range of from 0.008-0.08 mg of 6β-naltrexol per kg of body weight for oral administration of the antagonist and i.v. administration of the agonist. These dosage ranges were calculated as "human equivalent dosages" from the effective dosages determined in rodent models; it is anticipated that some dosage adjustment be made for other species, and specifically humans. The dosage for the analgesic in separate formulations suitable for co-administration with the neutral antagonist, was an $A_{90}$ dosage, which means it confers 90% analgesic activity.

In another related embodiment of the invention described above, the neutral opioid antagonist is 6β-naltrexol in a dosage of approximately 0.0008-0.24 mg per kg of body weight of the subject.

In another related embodiment of the invention described above, the neutral opioid antagonist is 6β-naltrexamide in a dosage of approximately 0.0024-0.8 mg per kg of body weight of the subject.

In another related embodiment of the invention described above, the analgesic composition is co-administered orally with neutral opioid antagonist. In still further related embodiments, the neutral opioid antagonist is 6β-naltrexamide in an oral administration with the agonist given by i.v., wherein the neutral antagonist dosage is approximately 0.024-0.8 mg per kg of body weight of the subject. Again, the analgesic is given at an $A_{90}$ dose.

Similar ranges are determined, as indicated, for other neutral antagonists of the present invention.

Another embodiment comprises a method for inhibiting peripheral effects of an opioid agonist while still permitting substantial central effects of the opioid agonist in a subject, the method comprising co-administering the opioid agonist with an effective amount of a unit dosage of a neutral opioid antagonist formulated as described to a subject in need thereof.

Still another embodiment provides a method of deterring addiction in a subject being administered an opioid agonist, the method comprising co-administering the opioid agonist with an effective amount of a unit dosage of a neutral opioid antagonist formulated according to as described to a subject in need thereof.

In related embodiments, the opioid agonist and unit dosage are administered orally, perorally, intragastrically, sublingually, by suppository, or intravenously.

Other embodiments provide a pharmaceutical formulation that deters diversion of an opioid agonist, the formulation comprising an amount of opioid agonist sufficient to induce a euphoric state or sufficient to relieve pain upon ingestion or administration, the opioid agonist having a blood half-life, and an effective amount of a neutral opioid antagonist with a ratio fixed relative to that of the opioid agonist, the neutral antagonist having a blood half-life substantially longer than the blood half-life of the opioid agonist, wherein upon successive administration, the blood concentration ratio of neutral opioid antagonist to opioid agonist increases with each successive administration, as measured in mg per kg of body weight of the subject, and such that repeated administration of the formulation in a dosage regimen exceeding therapeutically recommended limits results in reduced euphoria and reduced pain relief in the subject and so deters diversion.

Yet another embodiment provides a method for inhibiting peripheral effects of an opioid agonist while still permitting substantial central effects of the opioid agonist in a subject in need thereof, the method comprising co-administering to the subject in need thereof the opioid agonist with an effective amount of a unit dosage of a neutral opioid antagonist, the effective amount sufficient to inhibit peripheral effects and insufficient to block substantial central effects in the subject.

A more particular embodiment provides a method of deterring addiction in a subject being administered an opioid agonist, the method comprising co-administering to the subject the opioid agonist with an effective amount of a unit dosage of a neutral opioid antagonist, the effective amount sufficient to reduce euphoria and reduce pain relief upon successive administrations beyond therapeutically recommended limits, thereby deterring addiction.

In related method embodiments, the unit dosage of the opioid antagonist is selected from the group consisting of 6β-naltrexol, 6β-naltrexamide, 6β-naloxol, 6α-naltrexol, 6α-naloxol, 6α-naltrexamine, 6β-naltrexamine, 6-deoxynaltrexone, and 6α-naltrexamide, pharmaceutically acceptable physical isomorphs thereof, and pharmaceutically acceptable salts thereof.

In other related method embodiments, the opioid agonist and unit dosage may be administered in a manner selected from the group consisting of orally, perorally, intragastrically, sublingually, by suppository, intravenously and a combination thereof, and wherein co-administration is overlapping such that administration may be of a single co-formulation comprising agonist and antagonist, or may be simultaneous or sequential administration of separate agonist and antagonist formulations.

In various related embodiments of this invention, the opioid agonist of the analgesic composition is hydrocodone. In other particular embodiments, the unit dosage, pharmaceutical composition, and any or all of the methods may further comprise a neutral opioid antagonist that is suitable for formulation in a slow-release formulation, or is formulated in a slow-release formulation.

In a further related embodiment of the invention described above, the neutral opioid antagonist has a blood half-life substantially longer than the blood half-life of the opioid agonist, so that repeated abusive administration of the dosage causes a greater increase in blood concentration of the antagonist than of the agonist, so as to deter diversion, discourage abuse and/or reduce addiction liability to the agonist resulting from such administration.

In a further related embodiment of the invention described above, the neutral antagonist has physicochemical properties similar to that of the opioid agonist, so as to deter diversion of the agonist by extraction or other means.

In various embodiments, whether the embodiments are methods for inhibiting peripheral effects, deterring diversion or addiction, or reducing addiction liability, among other methods, are whether the embodiments are for a unit dosage or a pharmaceutical composition, the neutral antagonist may be formulated alone or together with the opioid agonist in a slow-release co-formulation. In such co-formulations, the neutral antagonist may be provided with an opioid agonist wherein only the neutral antagonist is provided in a slow-release form. Other embodiments provide a neutral antagonist with an opioid agonist in a co-formulation, wherein only the opioid agonist is provided in the co-formulation in a slow-release form. Still other embodiments provide a neutral antagonist with the opioid agonist in a co-formulation, wherein both the neutral antagonist and the opioid agonist are formulated as slow-release agents.

To deter diversion the neutral antagonist of the present invention is relatively lipophilic, similar to the agonists; moreover, greatest protection against diversion is achieved by making the two components in a co-formulation not easily separable. Further, the neutral antagonist is potent and is at least partially excluded from the brain, not primarily by means of high polarity, which also tends to reduce receptor potency (such as occurs with methylnaltrexone (MNTX)), but by other means, including but not limited to, the action of an extrusion pump (e.g. —the multi-drug resistance pump MDR1, which also keeps loperamide (immodium) out of the brain). The combination of these features makes the compounds of the invention unique. Lastly, such potent and relatively lipophilic antagonists have the tendency to show significantly delayed central activity (for kinetic reasons) compared to peripheral effects. This is advantageous for short term use, and it facilitates dosage schedules that prevent inappropriate dosage escalation.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1A:
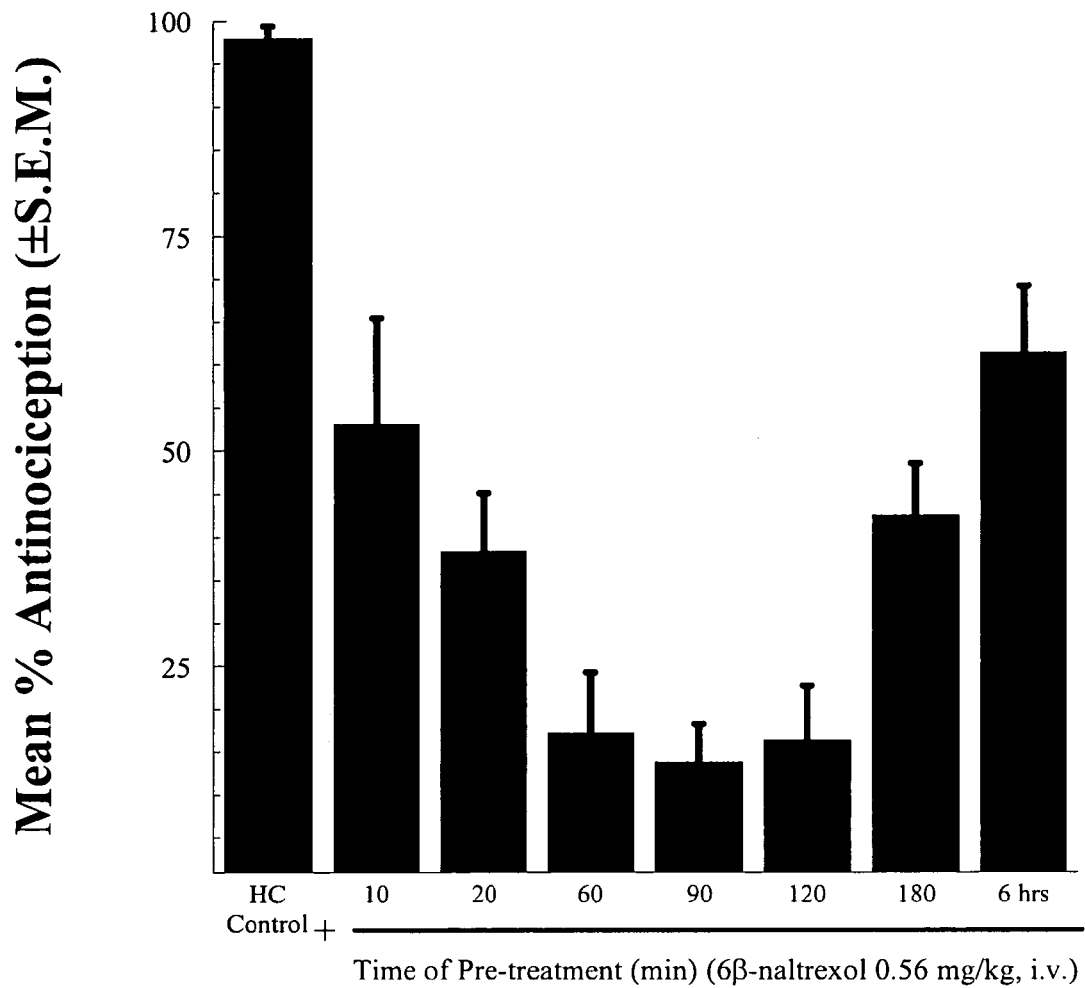
FIG. 1A is a graph that shows data reflecting the duration of the inhibitory effects of intravenously-administered 6β-naltrexol on an antinociceptive, intravenous dose of hydrocodone, and demonstrates the time of peak effect of antinociception inhibition.

Definitions. As used in this description and the accompanying claims, the following terms shall have the meanings indicated, unless the context otherwise requires:

6β-naltrexol is a naltrexone analog with the following structure:

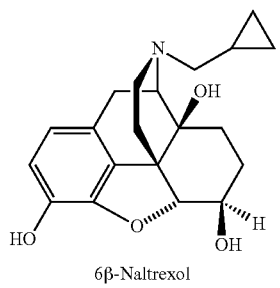

6β-Naltrexol

6β-naltrexamide is a naltrexone analog with the following structure:

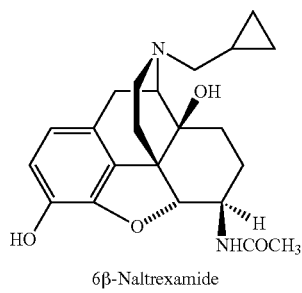

6β-Naltrexamide

Compounds 6β-Naltrexol and 6β-Naltrexamide may be represented by the generic formula Iβ, where the stereocenter at position 6 is indicated by an asterisk.

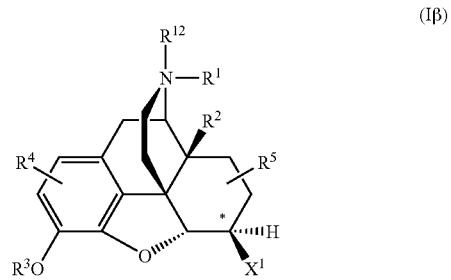

(Iβ)

The alpha isomers of 6-Naltrexol and 6-Naltrexamide may be represented by the generic formula Iα:

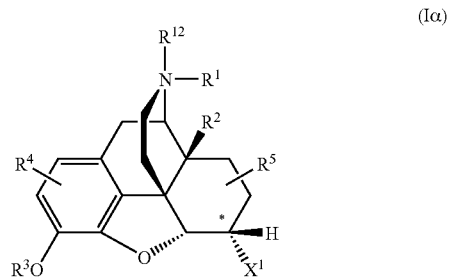

(Iα)

For generic formulae I α and Iβ, when $X^1$ and $X^2$ are the same, the stereocenter at this position, marked by an asterisk, goes away.

"$ID_{50}$ value" refers to a dose which inhibits activity by 50%.

"A blood half-life substantially longer than the blood half-life of the opioid agonist" as used herein means a blood half-life that is in the order of 2-fold greater, or more, as measured at $t_{1/2}=60$ min than that for the opioid agonist.

"$A_{90}$ dose" refers to the dose, for example of an opioid agonist, which produces 90% analgesic activity.

Pharmaceutically acceptable salts of the naltrexone and naloxone analogs, which are neutral antagonists at the μ opioid receptor, include salts derived from an appropriate base, such as an alkali metal (for example, sodium, potassium), an alkaline earth metal (for example, calcium, magnesium), ammonium and $NX._4^+$ (wherein X is $C_1$-$C_4$ alkyl). Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids.

In enantiomeric forms, compounds of the invention include individual enantiomers of the compounds in single species form substantially free of the corresponding enantiomer, as well as in admixture (in mixtures of enantiomeric pairs and/or in mixtures of multiple enantiomer species).

Opiates are a class of centrally acting compounds and are frequently used agents for pain control. Opiates are narcotic agonistic analgesics and are drugs derived from opium, such as morphine, codeine, and many synthetic congeners of morphine, with morphine being the most widely used derivative. Opioids are natural and synthetic drugs with morphine-like actions and include the opiates. Opioids are narcotic agonistic analgesics which produce drug dependence of the morphine type and are subject to control under federal narcotics law because of their addicting properties.

The chemical classes of opioids with morphine-like activity are the purified alkaloids of opium consisting of phenanthrenes and benzylisoquinolines, semi-synthetic derivatives of morphine, phenylpiperidine derivatives, morphinan derivatives, benzomorphan derivatives, diphenyl-heptane derivatives, and propionanilide derivatives. The principal phenanthrenes are morphine, codeine, and thebaine. The principal benzoisoquinolines are papaverine, a smooth muscle relaxant, and noscapine. Semi-synthetic derivatives of morphine include diacetylmorphine (heroin), hydromorphone, oxymorphone, hydrocodone, apomorphine, etorpine, and oxycodone. Phenylpiperidine derivatives include meperidine and its congeners diphenoxylate and loperamide, alphaprodine, anileridine hydrochloride or phosphate, and piminodine esylate. Morphinan derivatives include levorphanol. The diphenyl-heptane derivatives include methadone and its congeners, and propoxyphene. Propionanilide derivatives include fentanyl citrate and its congeners sufentanil citrate and alfenatil hydrochloride.

As used herein, a "therapeutically effective amount" refers to the amount of the naltrexone or naloxone analog or sustained release composition having the naltrexone or naloxone analog incorporated therein, needed to elicit the desired biological response following administration. The desired biological response herein can be sufficient blockade of the µ opioid receptor resulting in reducing adverse effects associated with current pain management such as diarrhea and constipation and without significantly inhibiting the central effects such as pain relief.

The neutral antagonist compositions of this invention can be administered in vivo, for example, a human, or an animal. Alternatively, a neutral antagonist can also be administered orally, transdermally, or parenterally such as by injection, implantation (e.g., subcutaneously, intramuscularly, intraperitoneally, intracranially, and intradermally), administration to mucosal membranes (e.g., intranasally, intravaginally, intrapulmonary, buccally or by means of a suppository), or in situ delivery (e.g., by enema or aerosol spray) to provide the desired dosage of naltrexone or naloxone analog to modulate undesirable effects of narcotic analgesic (such constipation, nausea, vomiting) in the treatment of pain or anesthesia, in an individual in need thereof.

"Neutral antagonists" as that term is used herein, refers to agents that block the effects of an agonist at the target receptor, but do not significantly affect the level of spontaneous activity present at the target receptor. "Neutral antagonist at the µ opioid receptor" as that term is used herein refers to an agent which can bind selectively to the resting, drug-sensitive µ opioid receptor state, to the constitutively active µ opioid receptor state, or to both, blocking the effects of an agonist at the receptor, but not significantly effecting the level of spontaneous activity present at the receptor.

The naloxone and naltrexone analogs represented by the structures presented herein can be synthesized using standard synthetic procedures such as those described in March J., Advanced Organic Chemistry, 3rd Ed. (1985), employing, for example, naltrexone or naloxone as the starting material.

Many of the analogs of naltrexone and naloxone which possess neutral antagonist activity at the µ opioid receptor, for example, the analogs wherein the 6-keto functionality has been reduced to an —OH functionality, are known compounds, and their syntheses have been described, for example, by Chatterjie et al., *J. Med. Chem.*, 18, pp. 490-492 (1975) and Jiang et al., J. Med. Chem., 20, pp. 1100-1102 (1977), incorporated by reference herein. When modification of the naltrexone or naloxone at the 6-keto position results in an additional chiral carbon in the analog, the β orientation at the newly formed chiral carbon is preferred over the α orientation, although the latter may be also appropriate in certain applications. This preference is based upon the probably slower conversion of the β analogs back to naloxone or naltrexone. Further, if desired, conversion of the naltrexone or naloxone analog can be blocked by any suitable inhibitory agent. For example, in the case of 6β or 6α-naloxol or naltrexol, conversion of the —OH at the 6 position back to the keto functionality of the naloxone or naltrexone can be inhibited with alcohol dehydrogenase inhibitors, such as 4-methylpyrazole (Plapp, B. V., "Control of Alcohol Metabolism," pp. 311-322 in Towards a Molecular Basis of Alcohol Use and Abuse, eds. Janssen et al., Birkhaeuser Verlag, 1994). Further, the replacement of the 6-keto functionality with, for example, an amine or amide resulting in 6α- and 6β-naltrexamine and naltrexamide is likely to undergo much slower, if any, conversion to naltrexone.

Other examples of potential neutral antagonists include the C-6-$H_2$ reduced analogue of naltrexol (access to the CNS++), whose molecular formula is $C_{20}H_{25}NO_3$ and whose IUPAC name is 17-(cyclopropylmethyl)4,5-epoxy-3,14-dihydroxymorphinan but for the purposes of this application is referred to as 6-deoxynaltrexone. Still other possibilities for neutral antagonists, based on the naloxone or naltrexone core formulas, can be envisioned, or may be identified, and are considered to fall within the scope of the invention and encompassed by the claims. For example, the C-6 position could be modified in other ways, whether by replacement of the keto group with halogens, alkyl- and alkoxyl groups, alkylamine groups, vinyl groups, secondary and tertiary amine groups, among others, or by modification at other sites, or in other ways, that retain the neutral antagonist activity at the µ receptor.

This definition of neutral antagonist also encompasses compounds that are not based on the naltrexone or naloxone core formulas, but may represent a new type of compound that still possesses the properties associated with a neutral antagonist of the µ receptor.

Thus, while the concept of neutral antagonist has been particularly shown and described with references to preferred embodiments thereof, it will be understood by those skilled in the art that various changes in form and details to the neutral antagonist core formulas, or to the development of completely unrelated core formulas for neutral antagonists, may be made therein without departing from the scope of the invention encompassed by the appended claims.

The term "sustained release composition" as defined herein, can comprise a biocompatible polymer having incorporated therein at least one naloxone or naltrexone analog which is a neutral antagonist at the µ opioid receptor. Suitable biocompatible polymers, can be either biodegradable or non-biodegradable polymers or blends or copolymers thereof, as described herein.

The sustained release compositions of the present inventions may comprise a neutral antagonist formulated alone or together with an opioid agonist in a slow-release co-formulation. In such co-formulations, the neutral antagonist may be provided with an opioid agonist wherein only the neutral antagonist is provided in a slow-release form. In other co-formulations with a neutral antagonist and an opioid agonist, only the opioid agonist is provided in the co-formulation in a slow-release form. And in still other co-formulations with a neutral antagonist and an opioid agonist, both the neutral antagonist and the opioid agonist are formulated as slow-release agents.

The sustained release compositions of this invention can be formed into many shapes such as a film, a pellet, a rod, a filament, a cylinder, a disc, a wafer or a microparticle. A microparticle is preferred. A "microparticle" as defined herein, comprises a polymer component having a diameter of less than about one millimeter and having a naltrexone or naloxone analog which is a neutral antagonist at the μ opioid receptor dispersed therein. A microparticle can have a spherical, non-spherical or irregular shape. Typically, the microparticle will be of a size suitable for injection. A preferred size range for microparticles is from about one to about 180 microns in diameter.

As defined herein, a sustained release of a naltrexone or naloxone analog of the present invention is a release of the agent from a sustained release composition. As explained above, a sustained release of a neutral antagonist with an opioid agonist may be release of the antagonist, or release of the agonist, or release of both the neutral antagonist and the opioid agonist from a sustained release composition. The release occurs over a period which is longer than that period during which a therapeutically significant amount of the naloxone or naltrexone analog, or the opioid agonist, would be available following direct administration of a solution of the analog. The period of sustained release can be, for example, about one day, about two days, about seven days, about ten days to one month, or more, as needed to attain the desired results. A sustained release of a naltrexone or naloxone analog of the invention from a sustained release composition, or of an opioid agonist in a co-formulation with a neutral antagonist from a sustained release composition, may be a continuous or a discontinuous release, with relatively constant or varying rates of release. The continuity of release and level of release can be affected by the type of polymer composition used (e.g., monomer ratios, molecular weight, and varying combinations of polymers), agent loading, and/or selection of excipients to produce the desired effect.

The polymers of the sustained release compositions described herein are biocompatible. Suitable biocompatible polymers, can be either biodegradable or non-biodegradable polymers or blends or copolymers thereof, as described herein.

Suitable biocompatible polymers, can be either biodegradable or non-biodegradable polymers or blends or copolymers thereof, as described herein. A polymer is biocompatible if the polymer and any degradation products of the polymer are non-toxic to the recipient and also possess no significant deleterious or untoward effects on the recipient's body, such as an immunological reaction at the injection site.

"Biodegradable", as defined herein, means the composition will degrade or erode in vivo to form smaller chemical species. Degradation can result, for example, by enzymatic, chemical and physical processes. Suitable biocompatible, biodegradable polymers include, for example, poly(lactides), poly(glycolides), poly(lactide-co-glycolides), poly(lactic acid)s, poly(glycolic acid)s, polycarbonates, polyesteramides, polyanhydrides, poly(amino acids), polyorthoesters, poly(dioxanone)s, poly(alkylene alkylate)s, copolymers or polyethylene glycol and polyorthoester, biodegradable polyurethane, blends thereof, and copolymers thereof.

Suitable biocompatible, non-biodegradable polymers include non-biodegradable polymers selected from the group consisting of polyacrylates, polymers of ethylene-vinyl acetates and other acyl substituted cellulose acetates, non-degradable polyurethanes, polystyrenes, polyvinylchloride, polyvinyl fluoride, poly(vinyl imidazole), chlorosulphonate polyolefin, polyethylene oxide, blends thereof, and copolymers thereof.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weight is of about 2,000 Daltons to about 2,000,000 Daltons.

In a particular embodiment, the polymer is biodegradable polymer or copolymer. In a more preferred embodiment, the polymer is a poly(lactide-co-glycolide) (hereinafter "PLG"). The PLG can have a lactide:glycolide ratio, for example, of about 10:90, 25:75, 50:50, 75:25 or 90:10 and a molecular weight of about 5,000 Daltons to about 70,000 Daltons.

It is understood that when the naltrexone or naloxone analog, which is a neutral antagonist at the μ opioid receptor, or when the opioid agonist, separately or in a co-formulation with a neutral antagonist, is incorporated into a biocompatible polymer for sustained release of the analog and/or agonist, the sustained release composition can include additional components which can stabilize the analog and/or modify the release profile of the naltrexone or naloxone analog from the sustained release composition. That is, the naltrexone or naloxone analog, or opioid agonist, of the sustained release composition can be stabilized against loss of potency and/or loss of activity, all of which can occur during formation of the sustained release composition having the naltrexone or naloxone analog and/or opioid agonist dispersed therein, and/or prior to and during in vivo release of the analog and/or agonist. In addition, the period of release of the naltrexone or naloxone analog, and/or the opioid agonist, can be prolonged.

A suitable excipient or a specific combination of excipients can be employed in the sustained release composition. "Excipient", as that term is used herein, is any agent which binds or interacts in a covalent or non-covalent manner or is included with the naloxone or naltrexone analog in the sustained release composition.

Suitable excipients include, for example, carbohydrates, amino acids, fatty acids, surfactants, and bulking agents, and are known to those skilled in the art. An acidic or a basic excipient is also suitable. The amount of excipient used is based on ratio to the naltrexone or naloxone analog, on a weight basis. For amino acids, fatty acids and carbohydrates, such as sucrose, trehalose, lactose, mannitol, dextran and heparin, the ratio of carbohydrate to analog, is typically between about 1:10 and about 20:1. For surfactants the ratio of surfactant to analog is typically between about 1:1000 and about 2:1. Bulking agents typically comprise inert materials. Suitable bulking agents are known to those skilled in the art.

The excipient can also be a metal cation component which acts to modulate the release of the naltrexone or naloxone analog. A metal cation component used in modulating release typically comprises at least one type of multivalent metal cation. Examples of metal cation components suitable to modulate release include or contain, for example, $Mg(OH)_2$, $MgCO_3$ (such as $4MgCO_3 \cdot Mg(OH)_2 \cdot 5H_2O$), $MgSO_4$, $Zn(OAc)_2$, $Mg(OAc)_2$, $ZnCO_3$ (such as $3Zn(OH)_2 \cdot 2ZnCO_3$), $ZnSO_4$, $ZnCl_2$, $MgCl_2$, $CaCO_3$, $Zn_3(C_6H_5O_7)_2$ and $Mg_3(C_6H_5O_7)_2$. A suitable ratio of metal cation component to polymer is between about 1:99 to about 1:2 by weight. The optimum ratio depends upon the polymer and the metal cation component utilized. A polymer matrix containing a dispersed metal cation component to modulate the release of a an agent from the polymer matrix is further described in U.S. Pat. No. 5,656,297 to Bernstein et al. the teachings of which are incorporated herein by reference in their entirety.

A number of methods are known by which sustained release compositions (polymer/active agent matrices) can be formed. In many of these processes, the material to be encapsulated is dispersed in a solvent containing a wall forming material. At a single stage of the process, solvent is removed from the microparticles and thereafter the microparticle product is obtained.

Methods for forming a composition for the sustained release of biologically active agent are described in U.S. Pat. No. 5,019,400, issued to Gombotz et al., and issued U.S. Pat. No. 5,922,253 issued to Herbert et al. the teachings of which are incorporated herein by reference in their entirety.

In this method, a mixture comprising a biologically active agent, a biocompatible polymer and a polymer solvent is processed to create droplets, wherein at least a significant portion of the droplets contains polymer, polymer solvent and the active. These droplets are then frozen by a suitable means. Examples of means for processing the mixture to form droplets include directing the dispersion through an ultrasonic nozzle, pressure nozzle, Rayleigh jet, or by other known means for creating droplets from a solution.

Means suitable for freezing droplets include directing the droplets into or near a liquified gas, such as liquid argon or liquid nitrogen to form frozen microdroplets which are then separated from the liquid gas. The frozen microdroplets are then exposed to a liquid or solid non-solvent, such as ethanol, hexane, ethanol mixed with hexane, heptane, ethanol mixed with heptane, pentane or oil.

The solvent in the frozen microdroplets is extracted as a solid and/or liquid into the non-solvent to form a polymer/active agent matrix comprising a biocompatible polymer and a biologically active agent. Mixing ethanol with other non-solvents, such as hexane, heptane or pentane, can increase the rate of solvent extraction, above that achieved by ethanol alone, from certain polymers, such as poly(lactide-co-glycolide) polymers.

A wide range of sizes of sustained release compositions can be made by varying the droplet size, for example, by changing the ultrasonic nozzle diameter. If the sustained release composition is in the form of microparticles, and very large microparticles are desired, the microparticles can be extruded, for example, through a syringe directly into the cold liquid. Increasing the viscosity of the polymer solution can also increase microparticle size. The size of the microparticles which can be produced by this process ranges, for example, from greater than about 1000 to about 1 micrometers in diameter.

Yet another method of forming a sustained release composition, from a suspension comprising a biocompatible polymer and a biologically active agent, includes film casting, such as in a mold, to form a film or a shape. For instance, after putting the suspension into a mold, the polymer solvent is then removed by means known in the art, or the temperature of the polymer suspension is reduced, until a film or shape, with a consistent dry weight, is obtained.

A further example of a conventional microencapsulation process and microparticles produced thereby is disclosed in U.S. Pat. No. 3,737,337, incorporated by reference herein in its entirety, wherein a solution of a wall or shell forming polymeric material in a solvent is prepared. The solvent is only partially miscible in water. A solid or core material is dissolved or dispersed in the polymer-containing mixture and, thereafter, the core material-containing mixture is dispersed in an aqueous liquid that is immiscible in the organic solvent in order to remove solvent from the microparticles.

Another example of a process in which solvent is removed from microparticles containing a substance is disclosed in U.S. Pat. No. 3,523,906, incorporated herein by reference in its entirety. In this process a material to be encapsulated is emulsified in a solution of a polymeric material in a solvent that is immiscible in water and then the emulsion is emulsified in an aqueous solution containing a hydrophilic colloid. Solvent removal from the microparticles is then accomplished by evaporation and the product is obtained.

In still another process as shown in U.S. Pat. No. 3,691,090, incorporated herein by reference in its entirety, organic solvent is evaporated from a dispersion of microparticles in an aqueous medium, preferably under reduced pressure.

Similarly, the disclosure of U.S. Pat. No. 3,891,570, incorporated herein by reference in its entirety, shows a method in which solvent from a dispersion of microparticles in a polyhydric alcohol medium is evaporated from the microparticles by the application of heat or by subjecting the microparticles to reduced pressure.

Another example of a solvent removal process is shown in U.S. Pat. No. 3,960,757, incorporated herein by reference in its entirety.

Tice et al., in U.S. Pat. No. 4,389,330, describe the preparation of microparticles containing an active agent by a method comprising: (a) dissolving or dispersing an active agent in a solvent and dissolving a wall forming material in that solvent; (b) dispersing the solvent containing the active agent and wall forming material in a continuous-phase processing medium; (c) evaporating a portion of the solvent from the dispersion of step (b), thereby forming microparticles containing the active agent in the suspension; and (d) extracting the remainder of the solvent from the microparticles.

Further suitable methods of preparation are described in U.S. Pat. No. 6,194,006 to Lyons et al., U.S. Pat. Nos. 6,110,503, 5,916,598 and 5,792,477 to Rickey et al. and U.S. Pat. No. 5,650,173 to Ramstack et al. the entire content of all of which is hereby incorporated by reference.

While this invention has been particularly shown and described with references to preferred embodiments thereof, it will be understood by those skilled in the art that various changes in form and details may be made therein without departing from the scope of the invention encompassed by the appended claims.

Effect of 6β-Naltrexol on Hydrocodone-Induced Antinociception

Previous work confirms that 6β-naltrexol antagonizes the central effects of opioids. For example, research by Wang D, Raehal K M, Bilsky E J, Sadee W. (2001 June) "Inverse agonists and neutral antagonists at mu opioid receptor (MOR): possible role of basal receptor signaling in narcotic dependence," *J Neurochem.;* 77(6):1590-600 showed that 6β-naltrexol reverses morphine-induced antinociception when administered intraperitoneally. Other experiments have further shown that 6β-naltrexol prevents the stereotypic circling induced by morphine in non-dependent and chronically dependent mice (Wang D., Raehal K. M., Lin E. T., Lowery J. J., Kieffer B. L., Bilsky E. J., Sadee W. (2004 February Epub 2003 Nov. 4) "Basal signaling activity of mu opioid receptor in mouse brain: role in narcotic dependence," *J Pharmacol Exp Ther.;* 308(2):512-20; Raehal K. M., Lowery J. J., Bhamidipati C. M., Paolino R. M., Blair J. R., Wang D., Sadee W., Bilsky E. J. (2005 June; Epub 2005 Feb. 16) "In vivo characterization of 6β-naltrexol, an opioid ligand with less inverse agonist activity compared with naltrexone and naloxone in opioid-dependent mice," *J Pharmacol Exp Ther* 313(3):1150-62).

Experimental Data Demonstrates that 6β-Naltrexol Reverses Hydrocodone-Induced Antinociception.

Example 1

Tail-Flick Assay

Antinociception was assessed using a 55° C. warm-water tail-flick assay (Bilsky E. J., Qian X., Hruby V. J., Porreca F. (2000 April) "Antinociceptive activity of [beta-methyl-2',6'-dimethyltyrosine(1)]-substituted cyclic [D-Pen(2), D-Pen(5)]Enkephalin and [D-Ala(2),Asp(4)]Deltorphin analogs," *J Pharmacol Exp Ther*; 293(1):151-8; Raehal K. M., Lowery J. J., Bhamidipati C. M., Paolino R. M., Blair J. R., Wang D., Sadee W., Bilsky E. J. (2005 June; Epub 2005 Feb. 16) "In vivo characterization of 6beta-naltrexol, an opioid ligand with less inverse agonist activity compared with naltrexone and naloxone in opioid-dependent mice," *J Pharmacol Exp Ther* 313(3):1150-62). Male ICR mice (UNE) or CD-1 mice (Charles River) 25-40 grams were used in all procedures. Mice were weighed and the tails marked with indelible ink, with an n size of 8-10 mice/group. The latency to the first sign of a rapid tail-flick was used as the behavioral endpoint (Jannsen et al., 1963). Briefly, each mouse was tested for baseline latency by immersing the distal third of its tail into the water bath and recording the time until a vigorous tail-flick response to the noxious stimulus. Latencies typically averaged between 1.5 and 2.5 s in drug naïve subjects with any mice having a baseline latency greater than 5 s eliminated from further testing. Upon completion of baseline testing mice were injected and retested for tail-flick latencies at various times after injection (typically 10, 20, 30, 45, 60, 90, 120 and 180 minutes or until the test latency approaches the baseline latency, e.g., less than 20% MPE for the group.). A maximal score was assigned to mice not responding within 10 s to avoid tissue damage. The percentage of antinociception was calculated as (test latency−baseline latency)/(10−baseline latency)*100.

Antinociception Studies for Determining Time of Peak Effect of 6β-naltrexol.

Figure 1B:
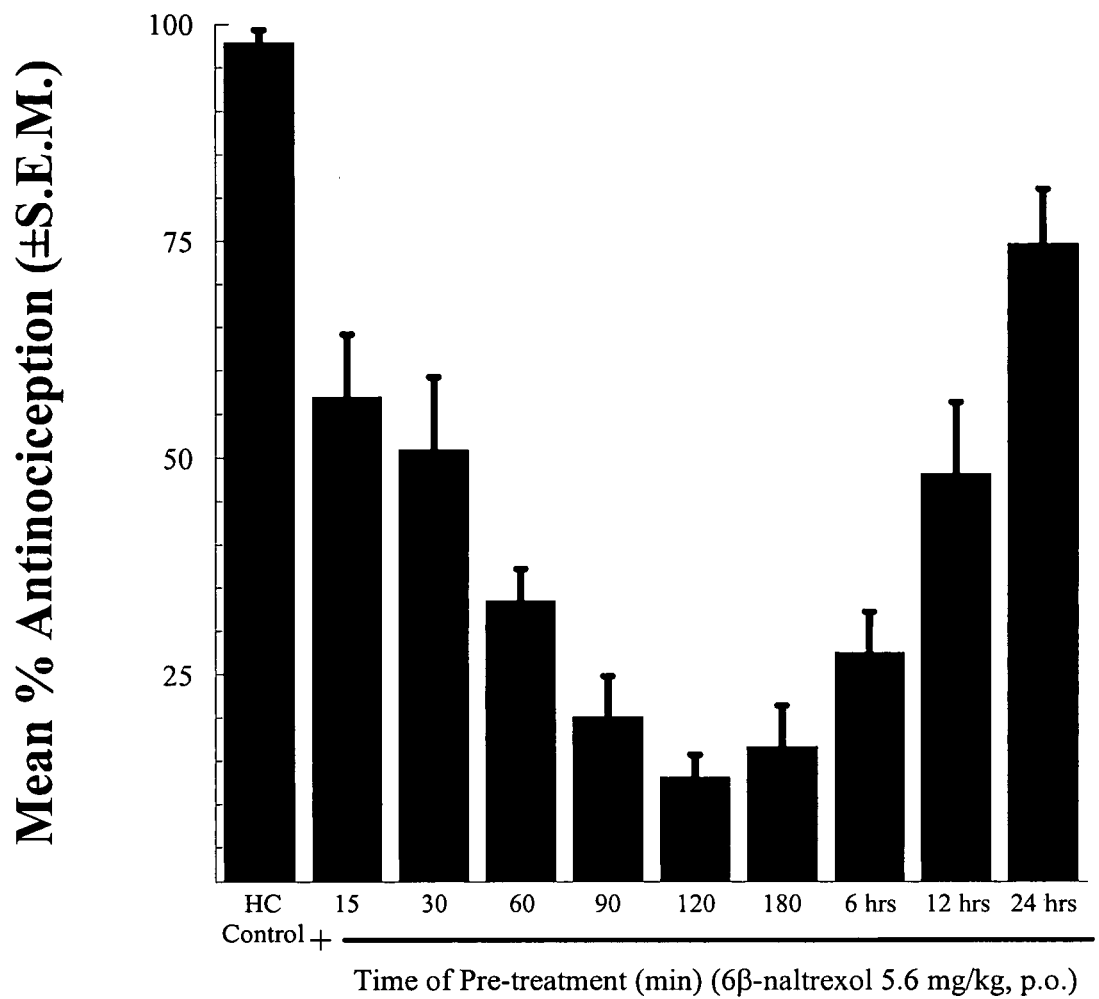
FIG. 1B is a graph that shows data reflecting the duration of the inhibitive effects of orally-administered 6β-naltrexol on an antinociceptive, intravenous dose of hydrocodone, and demonstrates the time of peak effect of antinociception inhibition.

The duration of 6β-naltrexol effects was measured by pretreating mice with 6β-naltrexol at various times prior to an injection of an antinociceptive $A_{90}$ dose of hydrocodone (3.2 mg/kg, i.v., dose determined previously; data not shown). Mice were tested 10 min later at the time of peak effect for hydrocodone in the tail-flick assay. 6β-naltrexol doses of 0.56 mg/kg for i.v. administration (FIG. 1A) and 5.6 mg/kg for p.o. administration (FIG. 1B) were used.

These time ranging experiments illustrated that 6β-naltrexol was capable of reversing the centrally mediated antinociceptive effects of hydrocodone (FIGS. 1A and 1B), with a time of peak effect at 90 min for i.v. administration and 120 min when administered p.o.

Antinociception Studies for Determining Antagonist Potencies.

Figure 2A:
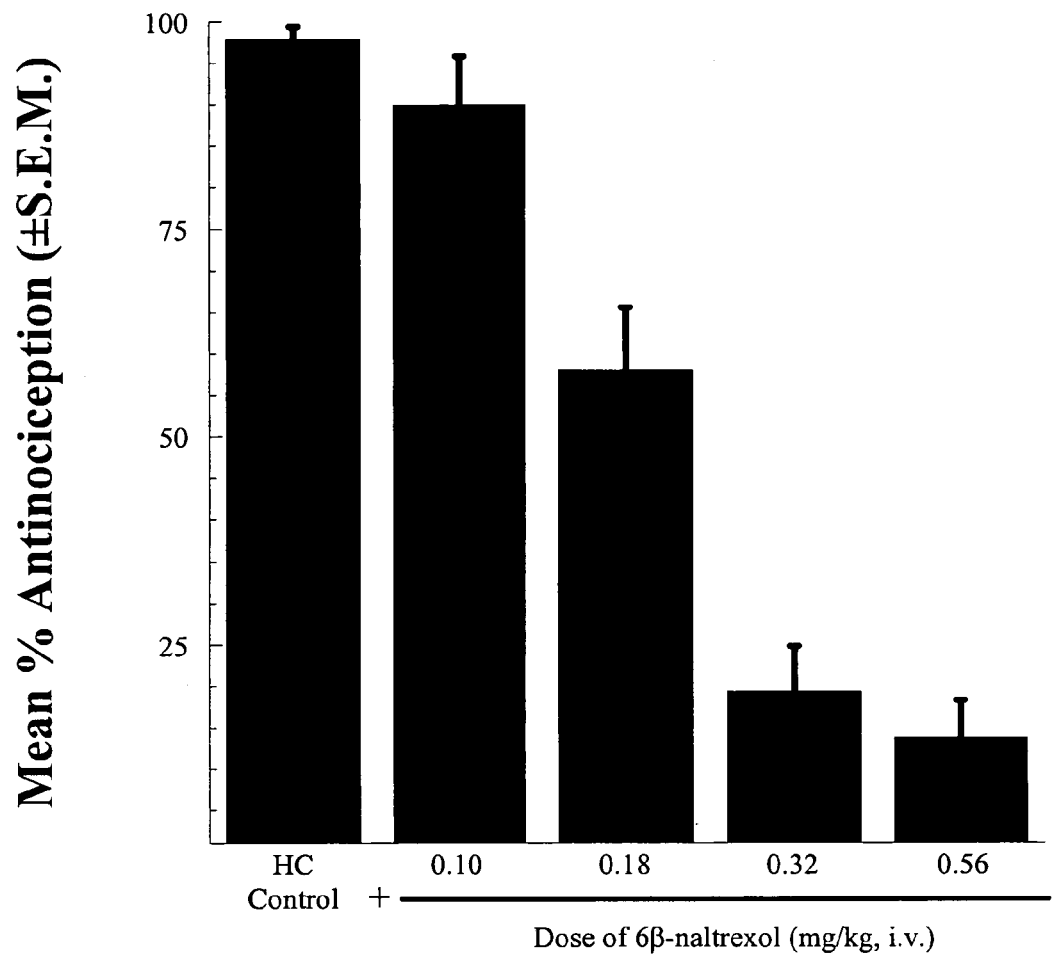
FIG. 2A is a dose response curve reflecting the potency of the inhibitive effects of intravenously-administered 6β-naltrexol on an antinociceptive, intravenous dose of hydrocodone.
Figure 2B:
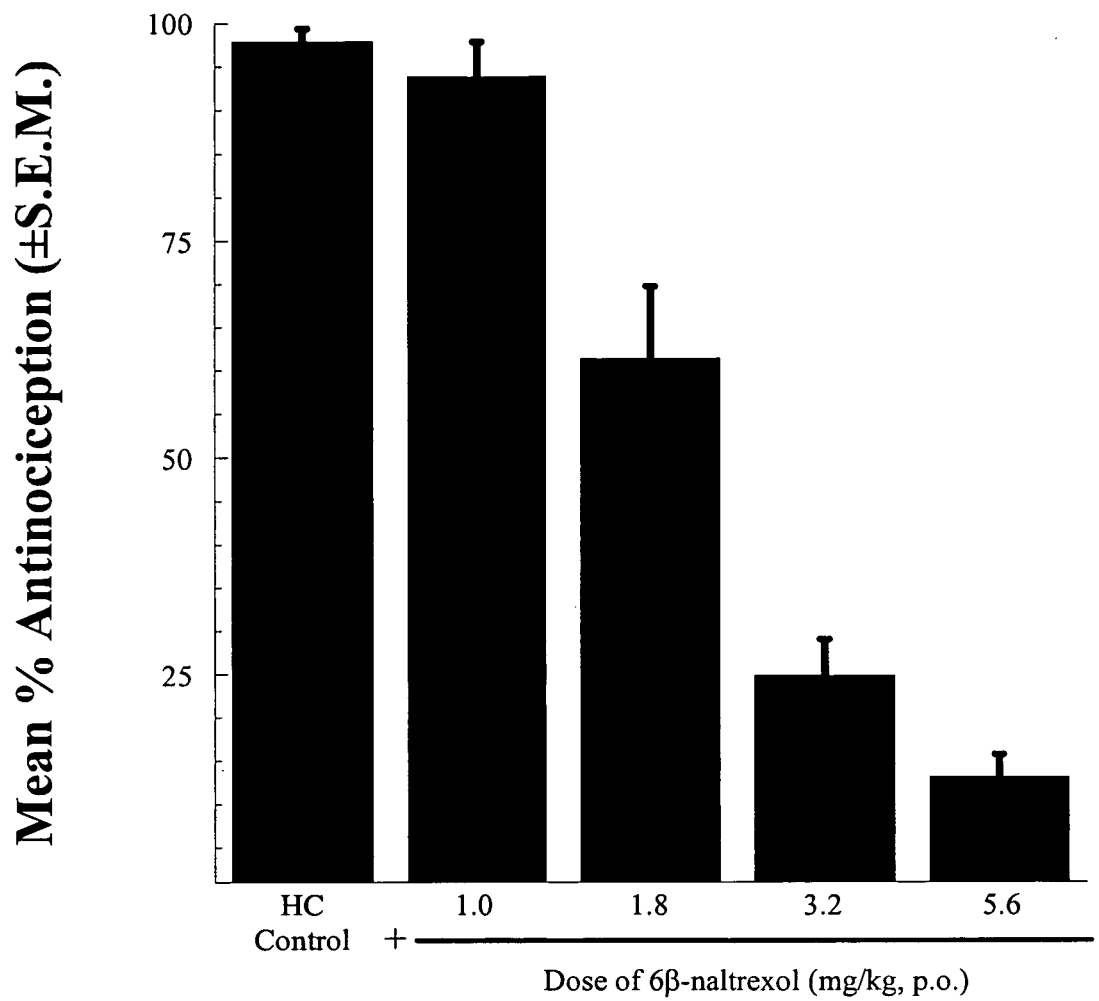
FIG. 2B is a dose response curve reflecting the potency of the inhibitive effects of orally-administered 6β-naltrexol on an antinociceptive, intravenous dose of hydrocodone.

Both oral and i.v. potencies were determined by administering vehicle or various doses of 6β-naltrexol at appropriate times prior to an $A_{90}$ dose of hydrocodone (3.2 mg/kg, i.v.). The respective i.v. and p.o. pretreatment times were 90 min (FIG. 2A) and 120 min (FIG. 2B). Mice were tested 10 min post hydrocodone injection (time of hydrocodone peak effect) in the 55° C. tail-flick assay. At least three doses were tested to produce a dose-response curve. The percent antinociception was then calculated for each dose and compared to hydrocodone controls.

These dose response curves were used to determine $ID_{50}$ value for 6β-naltrexol. The percentage of inhibition or reversal of the hydrocodone-induced antinociception was calculated as (test−hydrocodone control)/(saline control−hydrocodone control)*100. From this data an $ID_{50}$ value (and 95% confidence interval) was calculated for each route using linear regression (FlashCalc software; Dr. Michael Ossipov, University of Arizona, Tucson, Ariz.). $ID_{50}$ values for 6β-naltrexol inhibition of hydrocodone-induced antinociception were determined to be 0.222 mg/kg (95% CI=0.194-0.253) for i.v. administration, and 2.35 mg/kg (95% CI=2.11-2.63) for oral administration, consistent with this compound's 14% bioavailability in the rodent (previously determined data not shown).

Antinociception Studies for Oral Co-Administration.

The tail-flick assay was used to construct full dose- and time-response summaries for 6β-naltrexol in combination with hydrocodone. Vehicle or various doses of 6β-naltrexol were orally co-administered with an $A_{90}$ dose of hydrocodone (32 mg/kg, p.o.) determined previously (data not shown) at t=0 min. Tail-flick latencies were determined at t=10, 20, 30, 45, 60, 90, 120 and 180 minutes post injection (or until 20% MPE was reached) and % antinociception was calculated for each mouse (FIG. 3).

Figure 3:
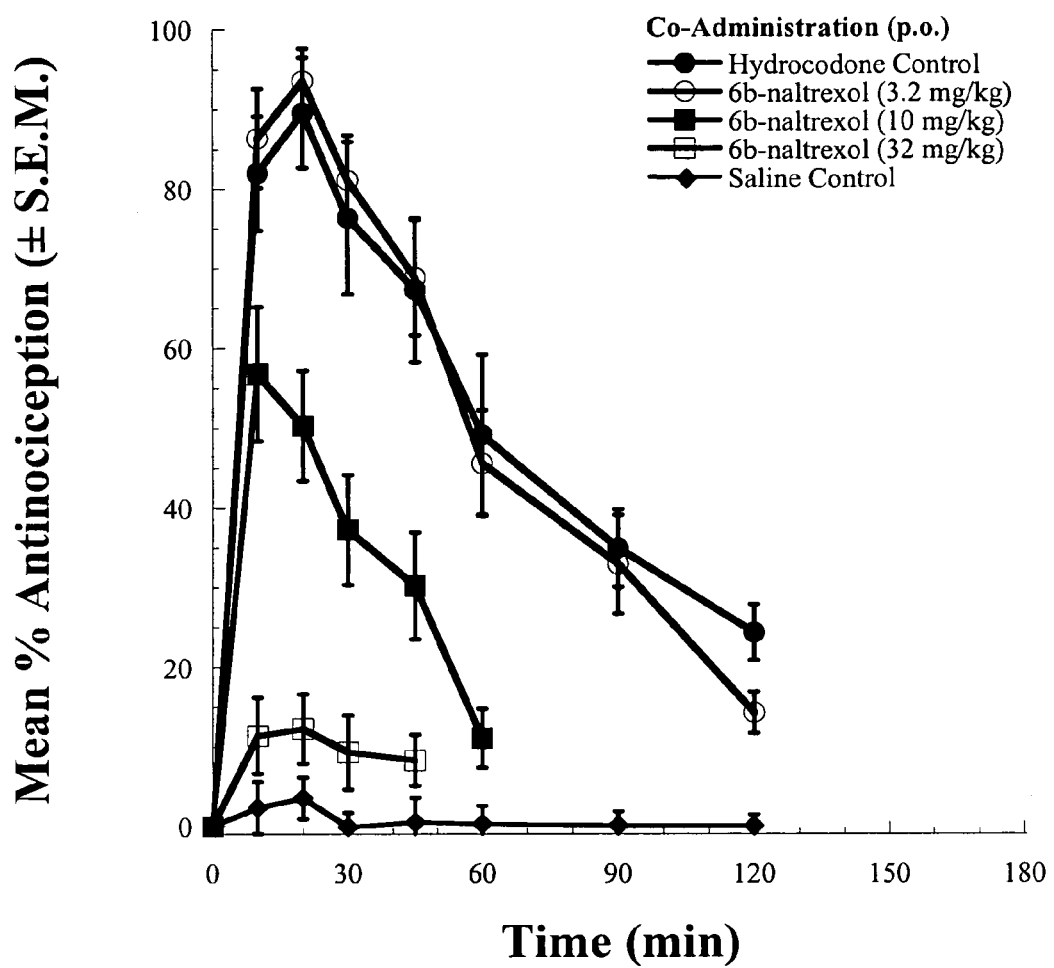
FIG. 3 is a graph that shows data reflecting the potency of the inhibitive effects of various concentrations of orally-administered 6β-naltrexol on an orally-co-administered, antinociceptive dose of hydrocodone.

The antinociception experiments shown in FIG. 3 yield an $ID_{50}$ value of 12.3 mg/kg (95% CI=10.4-14.7) for 6β-naltrexol co-administered with hydrocodone.

The experiments shown in FIGS. 1-3 demonstrate that 6β-naltrexol blocks hydrocodone-induced antinociception regardless of the route of administration.

Effect of 6β-Naltrexol on Hydrocodone-Induced Gastrointestinal Tract Slowing

Example 2

GI Transit Assay

Opioid-induced GI inhibition was measured using a standard protocol (Current Protocols in Pharmacology, number 5.3). Male CD-1 mice (Charles River) 25-40 grams are used in all procedures. Mice are weighed and the tails marked with indelible ink, with an n size of 8-10 mice/group. Mice were deprived of food for approximately 18 hr prior to the start of the experiment. 6β-naltrexol or saline was injected at 1 ml/100 g bodyweight (route and pretreatment time vary) prior to an oral delivery of a charcoal suspension (constant volume of 250 µL). At t=0 minutes, the oral charcoal is delivered using an 18 gauge curved gavage needle (Popper & Sons) on a 1 cc syringe. The suspension is made the day of use at 10% charcoal (100-400 mesh) with 2.5% arabic acid in distilled water and mixed thoroughly and repeatedly to minimize needle obstruction. Animals were sacrificed 30 min after administration of the charcoal meal by light ether anesthesia followed by cervical dislocation. The small intestine (duodenum to cecum) was dissected out and carefully uncoiled. The distance covered by the charcoal was measured and compared to the total length of the small intestine for each animal. The mean percent transit was then calculated as (distance covered by the charcoal)/(total length of the small intestine)*100.

GI Transit Studies for Determining 6β-Naltrexol Potency.

Figure 4A:
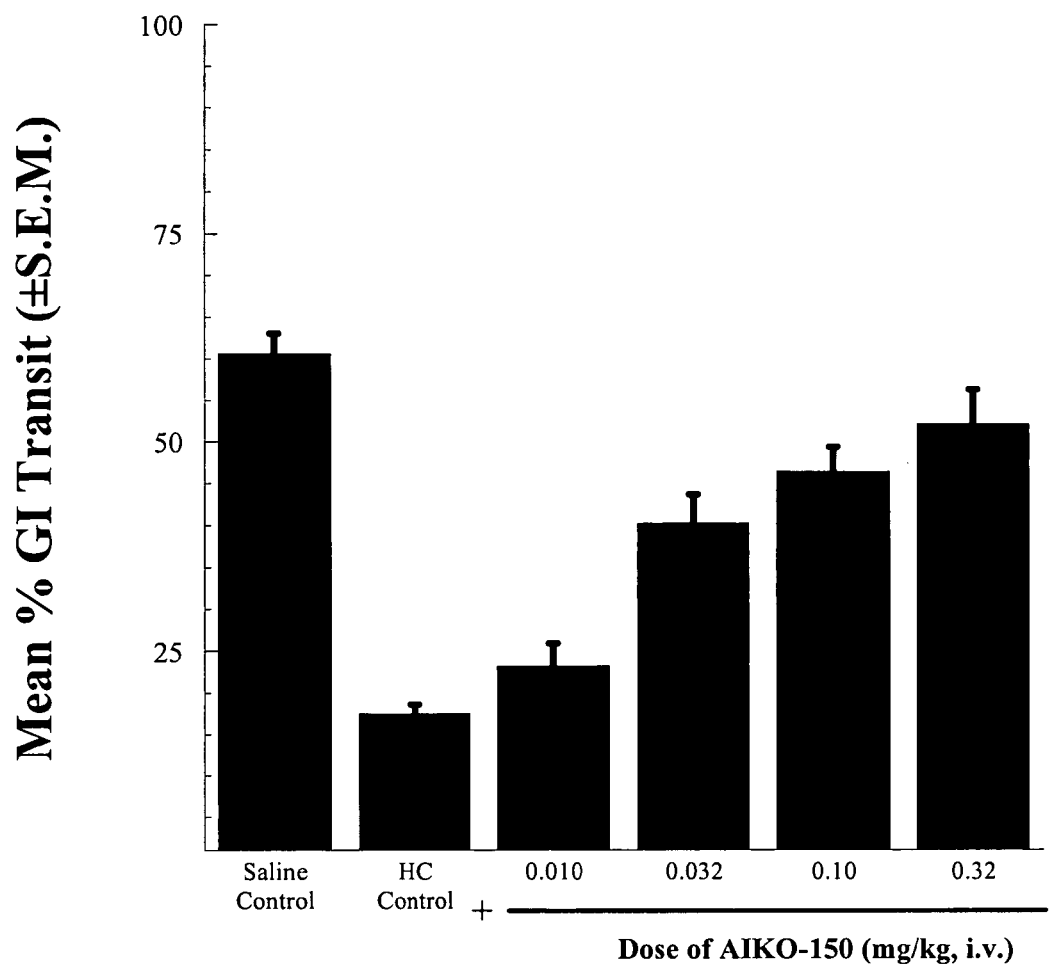
FIG. 4A is a dose response curve reflecting the potency of intravenously-administered 6β-naltrexol to reverse hydrocodone-induced GI transit slowing, where the two compounds are not co-administered.
Figure 4B:
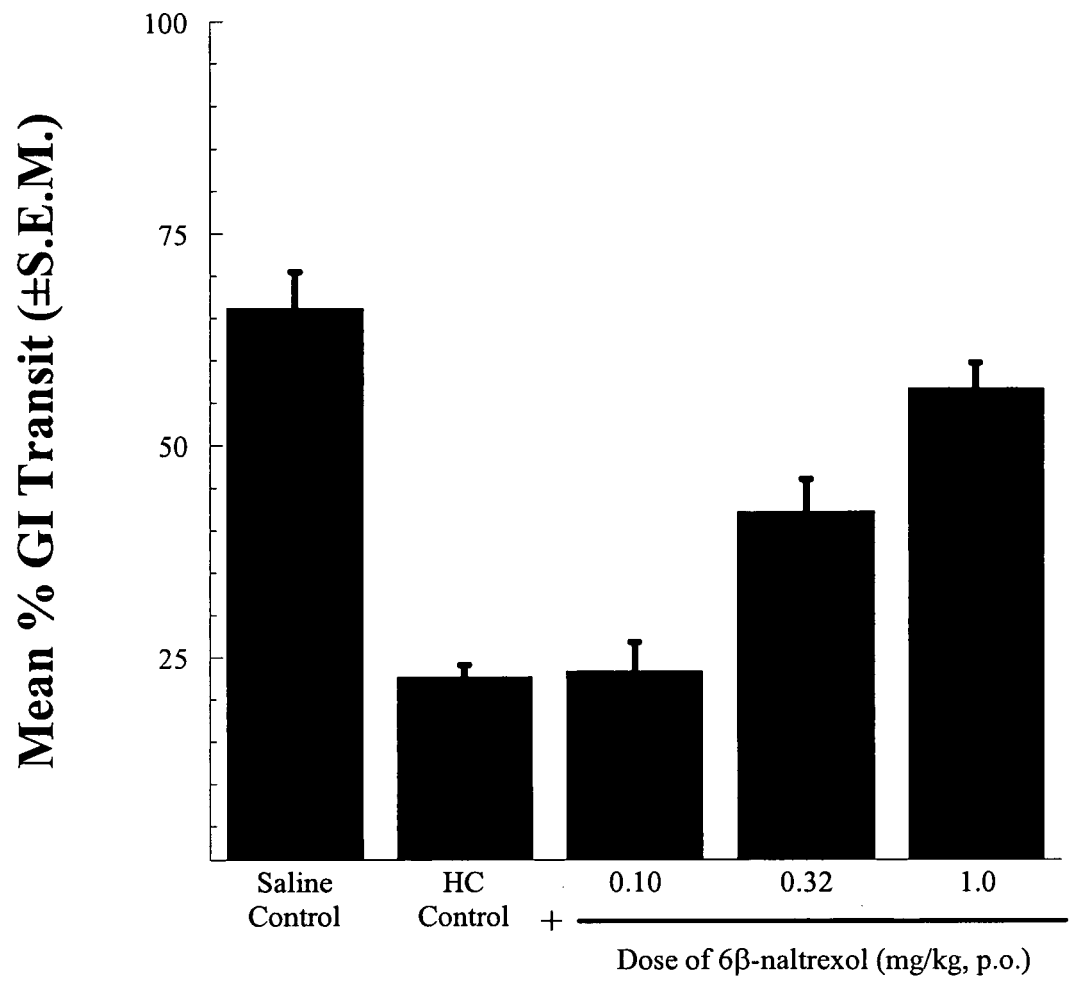
FIG. 4B is a dose response curve reflecting the potency of orally-administered 6β-naltrexol to reverse hydrocodone-induced GI transit slowing, where the two compounds are not co-administered.

The ability of 6β-naltrexol to block hydrocodone induced GI inhibition was assessed. Both i.v. (FIG. 4A) and oral potencies (FIG. 4B) were determined by administering vehicle or various doses of 6β-naltrexol prior to an antinociceptive $A_{90}$ dose of hydrocodone (3.2 mg/kg, i.v.). The pretreatment times corresponded with the time of peak effect for the antinociception studies. The charcoal meal was given 10 min following the injection of hydrocodone. Vehicle (saline) controls were also assessed i.v. The percentage of GI transit was calculated for each mouse and a dose-response curve was constructed for the antagonist. At least three doses were used for each route and the results were compared to saline and hydrocodone controls.

$ID_{50}$ values were calculated for 6β-naltrexol to determine potency to inhibit hydrocodone effects. 6β-naltrexol and hydrocodone were administered at appropriate times so that time of peak effect (as determined in the tail-flick assay) occurred during charcoal administration. 6β-naltrexol dose-dependently reversed the inhibition of GI transit by hydrocodone ($A_{90}$ dose, i.v.), yielding $ID_{50}$ values of 0.0443 mg/kg (95% CI=0.0275-0.0713) and 0.410 (95% CI=0.310-0.543) mg/kg for i.v. and p.o. (FIGS. 4A and 4B) administration, respectively.

GI Transit Studies for Oral Co-Administration.

Figure 5:
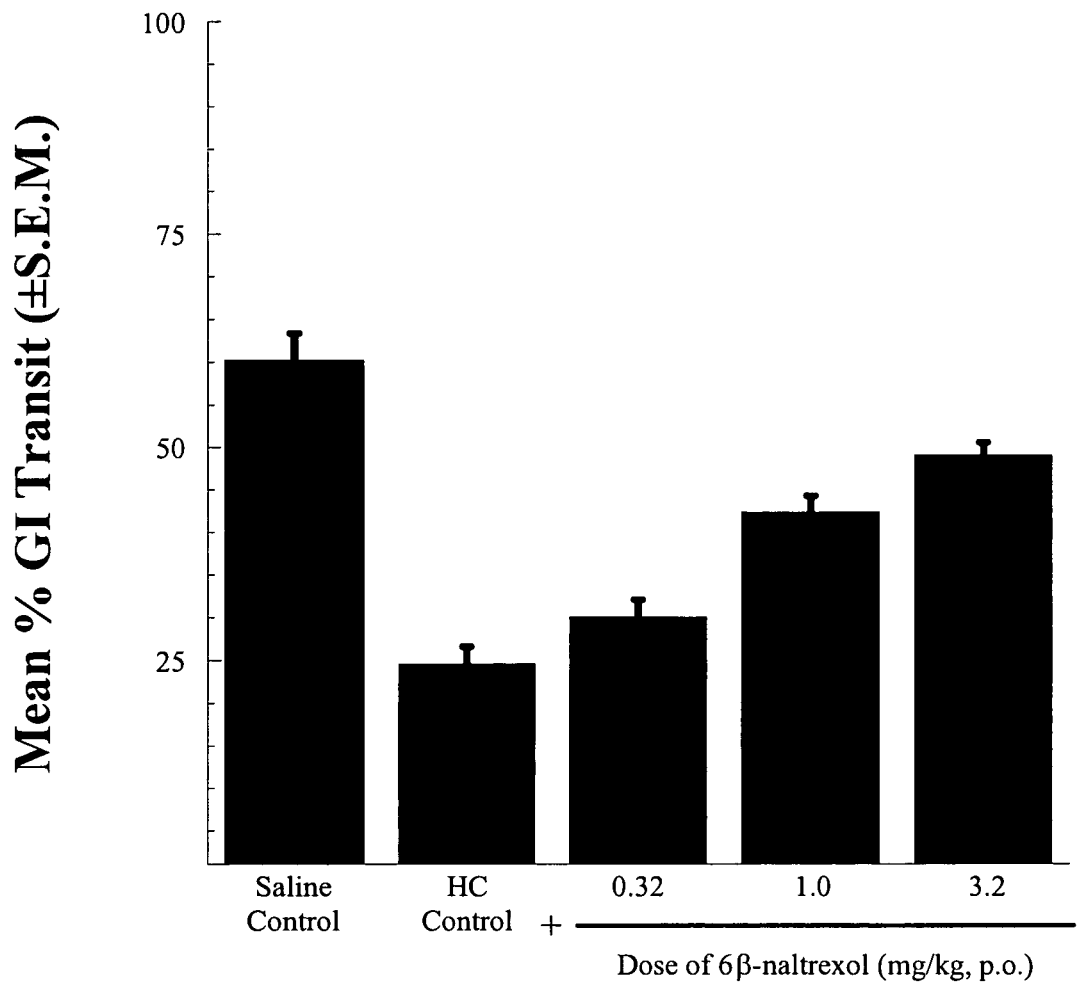
FIG. 5 is a dose response curve reflecting the potency of 6β-naltrexol to reverse hydrocodone-induced GI transit slowing when the two compounds are orally co-administered.

Vehicle (saline) or various doses of 6β-naltrexol were orally co-administered with an antinociceptive $A_{90}$ dose of hydrocodone (32 mg/kg, p.o.) 60 min prior to charcoal administration (FIG. 5). This time was chosen so that the time of peak effect for the antagonist would occur during intestinal transit of the charcoal meal. Vehicle (saline) controls were also assessed p.o. to compare the observed effects to opioid naïve mice. The percentage of GI transit was calculated for each mouse and a dose-response curve was constructed. At least three doses were used and the results were compared to saline and hydrocodone controls. 6β-naltrexol again dose-dependently reversed GI inhibition (FIG. 5) with an $ID_{50}$ of 1.290 mg/kg (95% CI=0.990-1.68).

Statistical Analysis.

The dose-response curves shown in FIG. 2-5 were used to estimate and compare central (antinociception) to peripheral (GI transit) potencies of 6β-naltrexol. The percentage of inhibition or reversal of the hydrocodone effect in either assay was determined for each mouse in the antagonist groups. The percent reversal was calculated as (test−hydrocodone control)/(saline control−hydrocodone control)*100. From this data an $ID_{50}$ value (and 95% confidence interval) was calculated for each route/antagonist/assay using linear regression (FlashCalc software; Dr. Michael Ossipov, University of Arizona, Tucson, Ariz.).

Potency of 6β-Naltrexol for Slowing GI-Transit and for Reversing Antinociception.

Figure 6A:
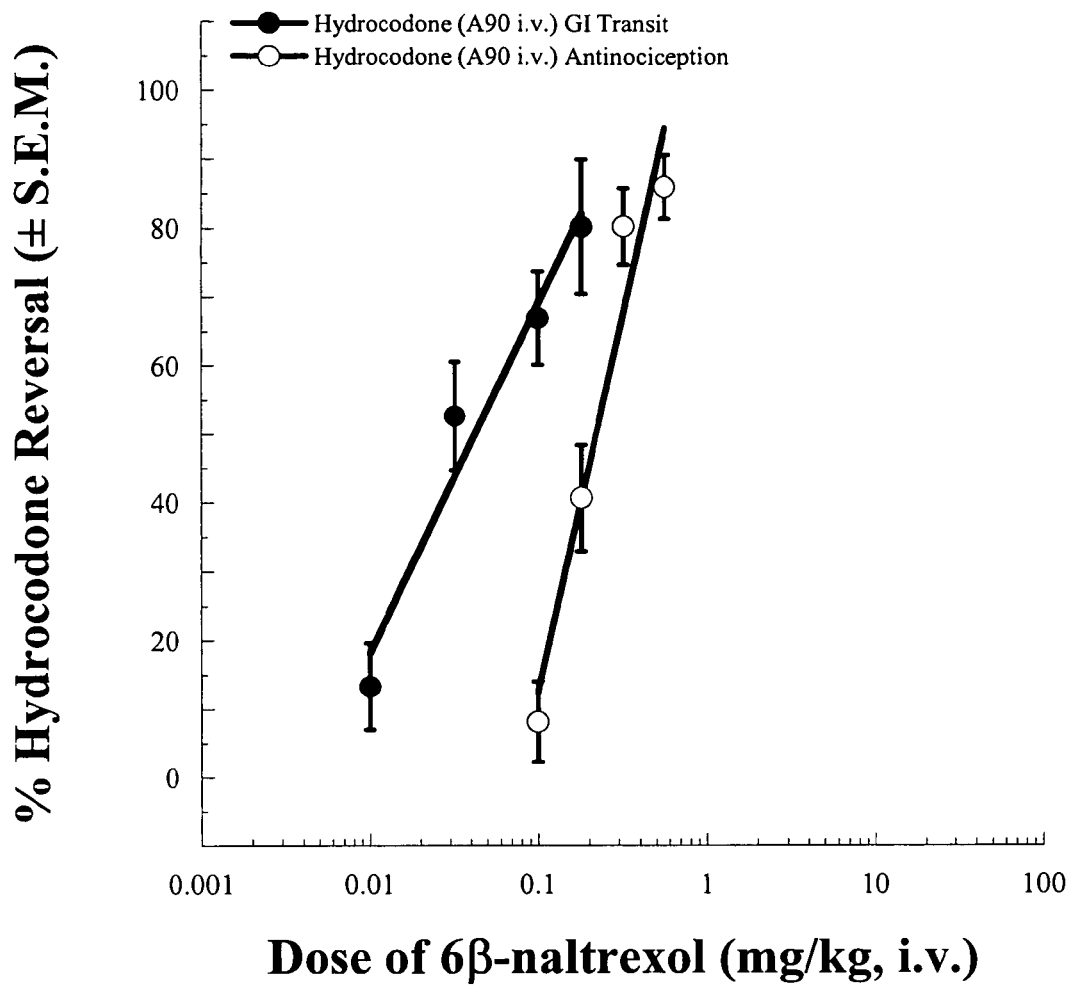
FIG. 6A shows the summarized potency data for inhibition of hydrocodone activity by 6β-naltrexol in GI transit studies (peripheral effects) and antinociception studies (central effects), where both 6β-naltrexol and hydrocodone were administered intravenously.
Figure 6B:
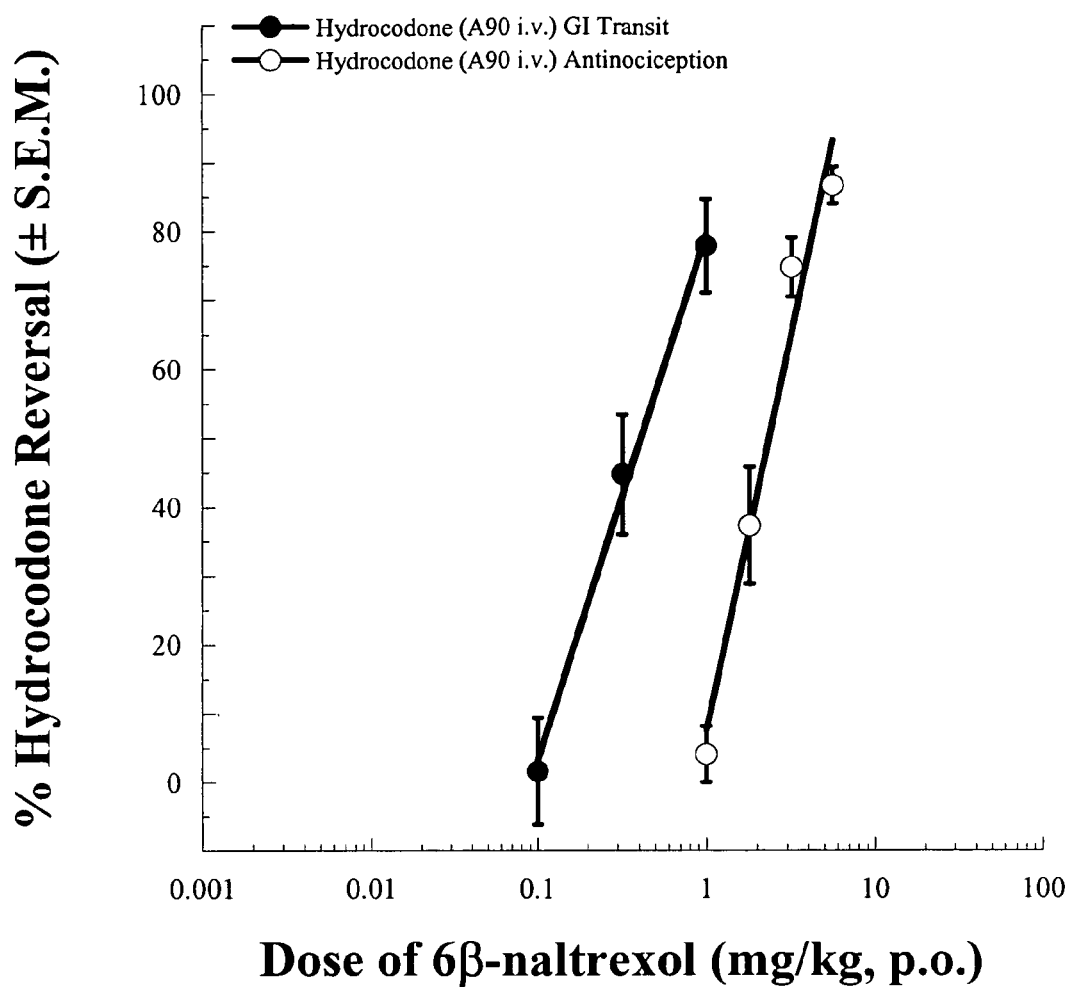
FIG. 6B shows the summarized potency data for inhibition of hydrocodone activity by 6β-naltrexol in GI transit studies (peripheral effects) and antinociception studies (central effects), where 6β-naltrexol was administered orally and hydrocodone was administered intravenously.
Figure 6C:
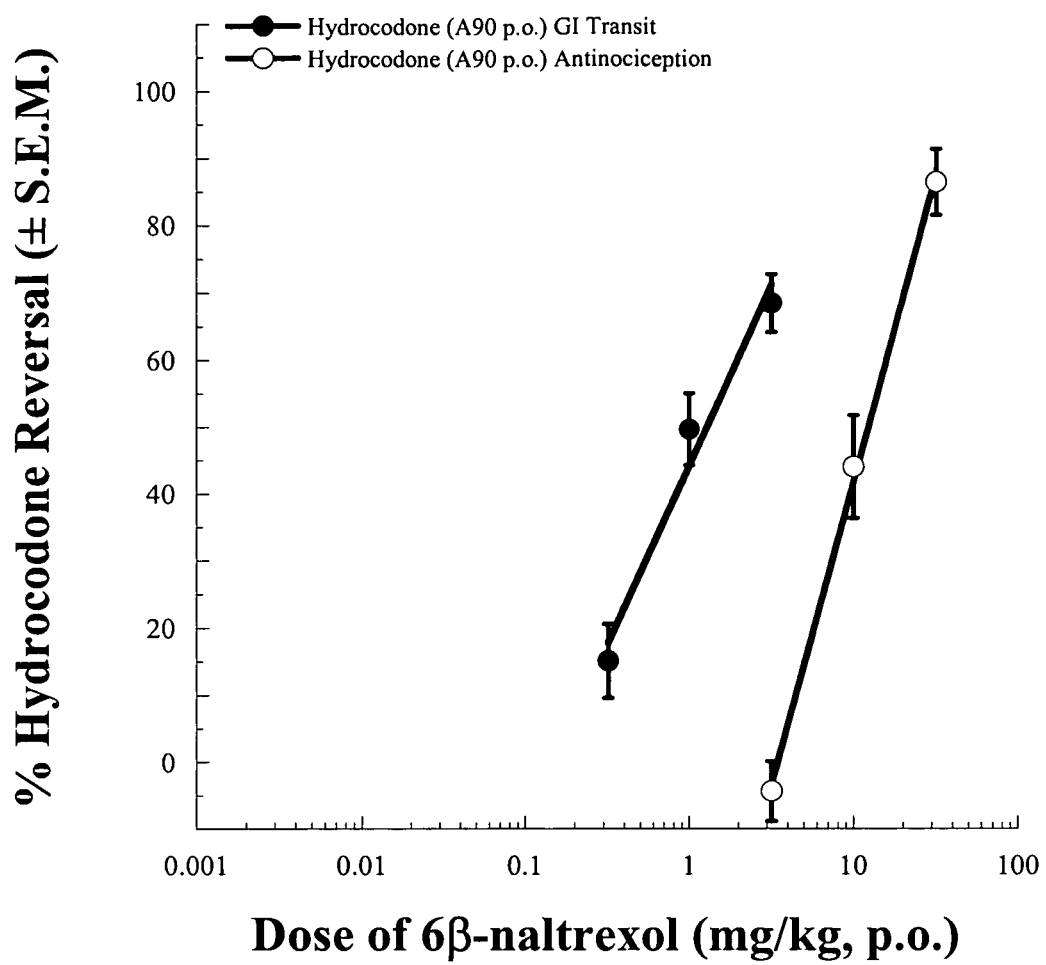
FIG. 6C shows the summarized potency data for inhibition of hydrocodone activity by 6β-naltrexol in the GI transit studies (peripheral effects) and antinociception studies (central effects) where both 6β-naltrexol and hydrocodone were orally co-administered.

Comparison of the calculated potencies ($ID_{50}$) for 6β-naltrexol to reverse either the central effects, antinociception, or peripheral effects, GI-transit slowing, induced by hydrocodone, led to the surprising discovery that 6β-naltrexol is 5-10-fold more potent peripherally than centrally. FIGS. 6A-C demonstrate this potency difference showing data derived from the dose response curves described above.

6β-naltrexol was found to have significant shifts in potency between the two assays for all administration parameters (FIGS. 6A-C). Both i.v. (FIG. 6A) and p.o. (FIG. 6B) administration of 6β-naltrexol were approximately 5-times more potent at reversing GI effects of i.v. hydrocodone than antinociceptive effects (Table 1). Furthermore, oral co-administration with hydrocodone resulted in a 9.53-fold shift in potency (FIG. 6C, Table 1). These data suggest that 6β-naltrexol is more potent at inhibiting peripheral effects than central effects induced by opioids.

Calculations of $ID_{50}$ potencies from these data further suggest that 6β-naltrexol is 9.5-fold more potent for slowing GI-transit than for reversing antinociception when both drugs are administered orally, as would be utilized for therapeutic use (Table 1).

These results indicate that there is a therapeutic window of effectiveness for 6β-naltrexol where peripheral side effects of opioid use are reduced without inhibition of analgesia. In the case of orally co-administered 6β-naltrexol and hydrocodone, that therapeutic window occurs when 6β-naltrexol is administered to a mouse from 0.1-3.0 mg/kg (FIG. 6C).

TABLE 1

The fold-shift in peripheral vs. central potency was calculated from the data presented in FIG. 6A-C and is shown in Table 1 as (antinociception $ID_{50}$)/(GI transit $ID_{50}$). (A fold-shift less than 1.0 indicates a greater central potency over peripheral potency.)

| Drug Combination | GI Transit $ID_{50}$ (95% CI) (mg/kg) | Antinociception $ID_{50}$ (95% CI) (mg/kg) | Fold-Shift |
|---|---|---|---|
| 6β-naltrexol (i.v.)/ Hydrocodone (i.v.) | 0.0443 (0.0275-0.0713) | 0.222 (0.194-0.253) | 5.01 |
| 6β-naltrexol (p.o.)/ Hydrocodone (i.v.) | 0.410 (0.310-0.543) | 2.35 (2.11-2.63) | 5.73 |
| 6β-naltrexol (p.o.)/ Hydrocodone (p.o.) | 1.290 (0.990-1.68) | 12.3 (10.4-14.7) | 9.53 |

This therapeutic window is surprising because it diverges dramatically from the ratios postulated by Simon in United States Patent Application 2004/0024006 A1. Our data also demonstrate that use of the dosages postulated by Simon (see United States Patent Application 2004/0024006 A1 at paragraphs [107] and [155]) would either have no effect (in the case of paragraph [107]) or have the unwanted effect of reversing antinociception (in the case of paragraph [155]).

The mouse data can be extrapolated to provide for effective formulation for humans. The 0.1-3.0 mg/kg mouse suggests a Human Equivalent Dose (HED) of 0.0081-0.243 mg/kg. This calculation is based on a body surface area calculation published in FDA guidelines for Estimating the Safe Starting Dose in Clinical Trials for Therapeutics in Adult Healthy Volunteers, available on Aug. 16, 2007 at www.fda.gov/cber/gdlns/dose.htm. If this dose is applied to a 70 kilo human, the human subject would need between 0.567-17.0 mg to have the desired effect of relieving GI transit slowing without inhibiting analgesia. A person skilled in the art could predict and conduct clinical testing to confirm similar pharmacokinetics in humans and determine the absolute correct dosage.

It should be noted that the concentrations required to reverse the antinociceptive effects of hydrocodone are consistent with the human blood levels of 6β-naltrexol obtained after standard naltrexone treatment for alcohol or opioid addiction maintenance where blocking the central effect is intended. Typically, a minimum dose of 50 mg naltrexone is administered daily to a human patient. The human must be opioid-free so there are no compounding effects on GI slowing or drug interactions altering pharmacokinetics or absorption. The literature teaches that approximately 43% of naltrexone is converted to 6β-naltrexol (for examples, see: Cone, E J, Gorodetzky C W, and Yea S Y (1974) "The Urinary Excretion Profile of Naltrexone and Metabolites in Man," Drug Metab and Disp 2(6): 506-512; ReVia™ Label; Wall M. E., Brine D. R, Perez-Reyes M. (1981) "Metabolism and Disposition of Naltrexone in Man after Oral and Intravenous Administration, Drug Metabolism and Disposition" *Drug Metabolism and Disposition,* 9(4):369-375; Verebey K. (1980) "The Clinical Pharmacology of Naltrexone: Pharmacology and Pharmacodynamics," *Naltrexone: NIDA Research Monograph,* 28, R E Willette and G Barnett, eds. pp 147-158; Wall M. E., Brine D. R., Perez-Reyes M. (1980)

"The Metabolism of Naltrexone in Man," *Naltrexone: NIDA Research Monograph*, 28, R E Willette and G Barnett, eds. pp 105-131; Perez-Reyes M. and Wall M. E. (1980) "A Comparative Study of the Oral, Intravenous, and Subcutaneous Administration f 3 h-Naltrexone to normal male volunteers," *Naltrexone: NIDA Research Monograph* 28, R E Willette and G Barnett, eds. pp 93-101), meaning humans are exposed to 20 mg of 6β-naltrexol following such a dose. Given that human dosages are determined for a standard 70 kg person, persons are routinely exposed to >0.3 mg 6β-naltrexol/kg body weight daily and often much higher dosages and blood levels are utilized. As such, there is evidence that this treatment level is safe in humans (for examples, see: Dunbar J. L., Turncliff R. Z., Dong Q., Silverman B. L., Ehrich E. W., Lasseter K. C. (2006) "Single- and Multiple-Dose Pharmacokinetics of Long-acting Injectable Naltrexone," *Alcohol: Clin and Exper Res.* 30(3):480-490; Jayaram-Lindstrom N., Wennberg P., Beck O., Franck J. (2005) "An open clinical trial of naltrexone for amphetamine dependence: Compliance and tolerability," *Nord J Pschy* 59(3):167-171; Brewer C. and Wong V. S. (2004) "Case Report. Naltrexone: report of lack of hepatotoxicity in acute viral hepatitis, with a review of the literature," *Addict Bio* 9, 81-87).

Substantially Longer Retention of 6β-Naltrexol and 6β-Naltrexamide in Plasma and Brain Tissue after i.p Injection in Mice Compared to Naltrexone.

Example 3

This study shows crude pharmacokinetics of 6β-naltrexol and 6b-naltrexamide in mouse plasma and brain (the naltrexol data were published in Wang et al. 2004; the naltrexamide data were not published) compared with naltrexone. Mice were injected i.p. with 1 mg/kg naltrexone, 1 mg/kg 6β-naltrexol, 1 mg/kg 6β-naltrexamide, 10 mg/kg 6β-naltrexol or 10 mg/kg 6β-naltrexamide and sacrificed after 10 or 60 min. Blood samples and whole brain were collected. Samples were analyzed for the presence of the antagonists using mass spectrometry.

Naltrexone, 6β-naltrexol and 6β-naltrexamide were extracted from plasma or brain tissue homogenates, measured by liquid chromatography/mass spectrometry/mass spectrometry (LC/MS/MS), using APCI/positive ionization. Nalbuphine served as the internal standard. The method was sensitive to ~1 ng/mL (g) (3-4 nM). 6β-Naltrexol was detectable in plasma but not brain tissue after the naltrexone dose (1.9 ng/mL and 1.7 ng/mL after 10 and 60 min, respectively). In contrast, no naltrexone was detectable after administration of 6β-naltrexol. The concentrations of two compounds in each row of the table represent the injected parent drug only. Mean±SD, n=3.

As shown, similar brain levels were achieved with equipotent doses of naltrexone and 6β-naltrexol or 6β-naltrexamide (1 mg/kg and 10 mg/kg, respectively). Surprisingly, after 60 min, the levels of 6β-naltrexol and 6β-naltrexamide had not changed from those measured at 10 min, whereas the levels of naltrexone declined nearly 90% by 60 min. This indicates a substantially longer retention in plasma and particularly in brain for 6β-naltrexol and 6β-naltrexamide than for naltrexone. These data can be extrapolated to suggest a substantially longer half-life for 6β-naltrexol and 6β-naltrexamide than that of opioid agonists such as naltrexone, in general. In humans the half-life of naltrexone is 4 hours, while that of 6β-naltrexol is ~15 hours. Importantly, both 6β-naltrexol and 6β-naltrexamide are much more effectively retained in the brain, suggesting a much longer effective duration of action compared to naltrexone in mice, while immediate access is considerably less. Opioid agonist half lives in humans are typically shorter, ~2-6 hours.

TABLE 2

Concentrations of naltrexone, 6βnaltrexol and 6β-naltrexamide in plasma and brain tissue after i.p. injection in mice.

| Injection | Plasma concentration (ng/ml) Time after injection (min) | | Brain concentration (ng/g) Time after injection (min) | |
|---|---|---|---|---|
| | 10 | 60 | 10 | 60 |
| Naltrexone, 1 mg/kg | 54 ± 16 | 4 ± 1 | 69 ± 20 | 9 ± 1 |
| 6β-Naltrexol, 1 mg/kg | 61 ± 7 | 24 ± 28 | 7 ± 6 | 9 ± 1 |
| 6β-Naltrexol, 10 mg/kg | 857 ± 122 | 75 ± 25 | 89 ± 6 | 74 ± 14 |
| 6β-Naltrexamide, 1 mg/kg | 115 ± 2 | 18 ± 1 | 6 ± 1 | 4 ± 1 |
| 6β-Naltrexamide, 10 mg/kg | 933 ± 221 | 166 ± 77 | 27 ± 6 | 24 ± 1 |

6β-Naltrexol+Opioid as a Co-Formulated Product

The results in Table 1 and Table 2 indicate that a co-formulated product containing a specified dose of hydrocodone and 6β-naltrexol can be created that will effectively treat moderate to severe pain with limited peripheral side effects such as, but not limited to, constipation, and may possibly also reduce nausea and vomiting. The pain relief would be similar to treatment with hydrocodone alone while the peripheral side effects would be much reduced.

Moreover, this co-formulation will confer abuse resistance because the central effects of the opioid will be antagonized by the 6β-naltrexol when doses exceeding those prescribed are taken by any route of administration, including if the tablet is manipulated, crushed and injected or snorted. In the case where doses exceeding those prescribed are taken orally, the substantially longer half-life of 6β-naltrexol compared to opioid will cause 6β-naltrexol to accumulate to doses that will sufficiently penetrate the CNS to antagonize centrally-mediated opioid effects such as pain relief and euphoria. This will be beneficial in cases of both accidental and intentional overdose. Due to the substantially longer half-life of 6β-naltrexol compared to opioid agonists, the effects will become more profound as doses are increased, thus preventing this co-formulated product from oral or other abuse as is now common for opioids.

In other words, the substantially longer half-life for the neutral antagonists than of the opioid agonists means the neutral antagonist will accumulate. Dosage will therefore be determined such that when steady-state is achieved, there will be relief of the GI side effects (including possibly nausea and vomiting) without impacting pain relief. The co-formulation will be made, factoring in a calculation for regular dosing of the opioid, such that the patient or subject will receive the appropriate level of neutral antagonist to relieve GI side effects, yet still allow the opioid agonist to relieve pain. Taking higher than prescribed doses of the co-formulation prevents addiction and deters abuse because at higher or multiple doses, the neutral antagonist begins to accumulate and then competes with the effects of the opioid, lessening the pain relief, or, if the formulation is taken for pleasure, the euphoria.

In cases where the co-formulation is injected as a form of abuse, the higher bioavailability of the antagonist administered directly to the bloodstream will allow antagonism of the central effects at lower doses. As with oral administration, the effects will become more profound over time as levels of the antagonist continue to accumulate through repeated dosing due to the limited half-life of the opioid. Yet, because 6β-naltrexol is a neutral antagonist, these effects will manifest without, or with substantially less, precipitating withdrawal, providing an effective means for preventing misuse. See Sadee and Simon.

Effect of 6β-Naltrexamide on Hydrocodone-Induced Antinociception

Example 4

Tail Flick Assay

The tail-flick assay was used to measure antinociception as described above under Example 1.

Antinociception Studies for Determining Time of Peak Effect of 6β-Naltrexamide.

Figure 7A:
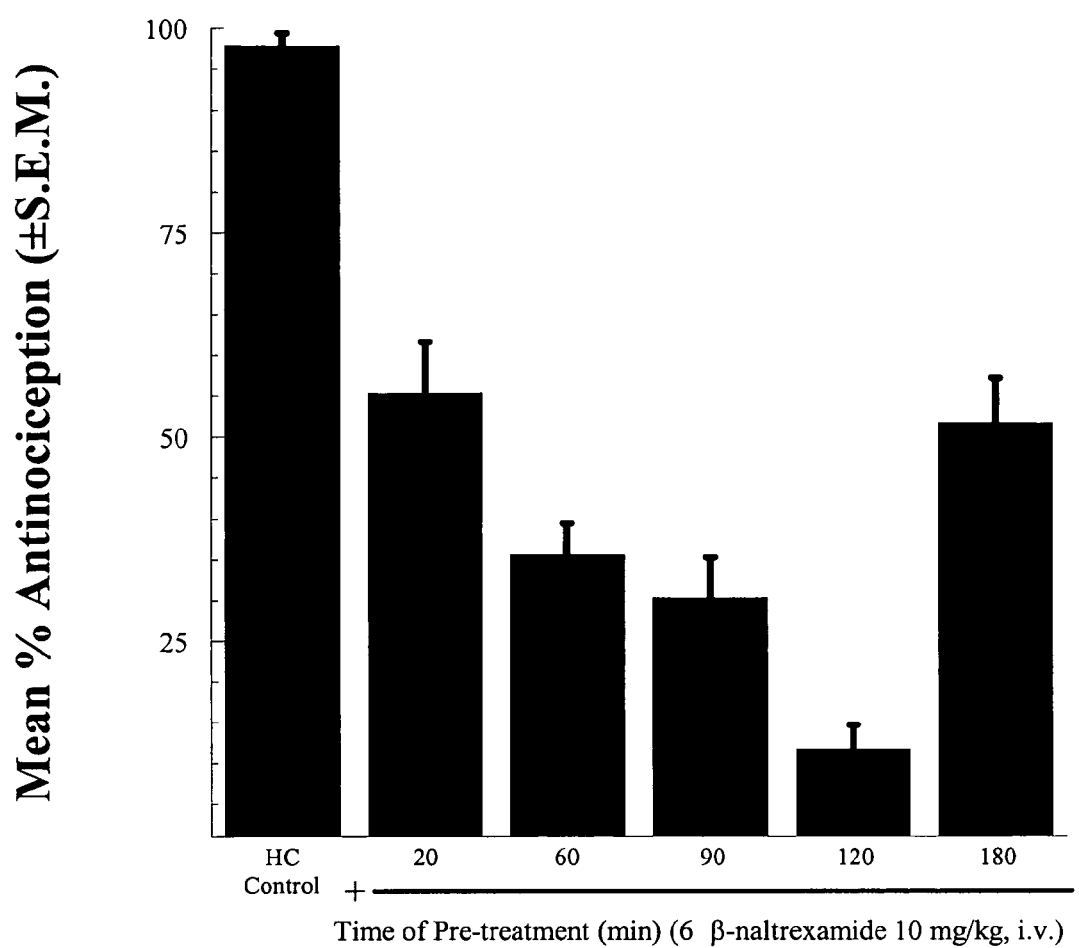
FIG. 7A is a graph that shows data reflecting the duration of the inhibitive effects of intravenously-administered 6β-naltrexamide on an antinociceptive, intravenous dose of hydrocodone, and demonstrates the time of peak effect of antinociception inhibition.
Figure 7B:
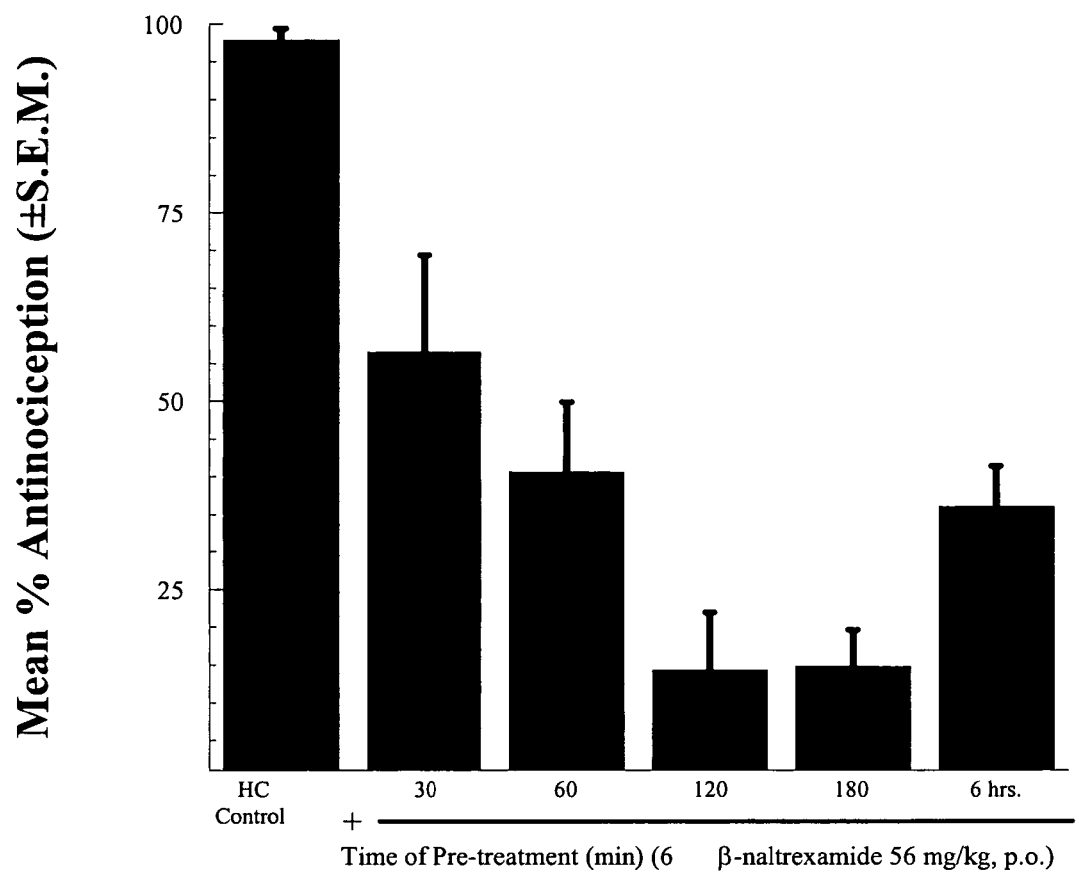
FIG. 7B is a graph that shows data reflecting the duration of the inhibitive effects of orally-administered 6β-naltrexamide on an antinociceptive, intravenous dose of hydrocodone, and demonstrates the time of peak effect of antinociception inhibition.

The duration of 6β-naltrexamide effects were measured by pretreating mice with 6β-naltrexamide at various times prior to an injection of an antinociceptive $A_{90}$ dose of hydrocodone (3.2 mg/kg, i.v., dose determined previously; data not shown). Mice were then tested 10 min later, at time of peak effect for hydrocodone, in the tail-flick assay. 6β-naltrexamide doses of 10 mg/kg (FIG. 7A) and 56 mg/kg (FIG. 7B) were used for i.v. and p.o. administration, respectively.

These time ranging experiments illustrated that 6β-naltrexamide was capable of reversing the centrally mediated antinociceptive effects of hydrocodone (FIGS. 7A and 7B), with a time of peak effect at 120 min for i.v. administration and 120-180 min when administered p.o.

Antinociception Studies for Determining Antagonist Potencies.

Figure 8A:
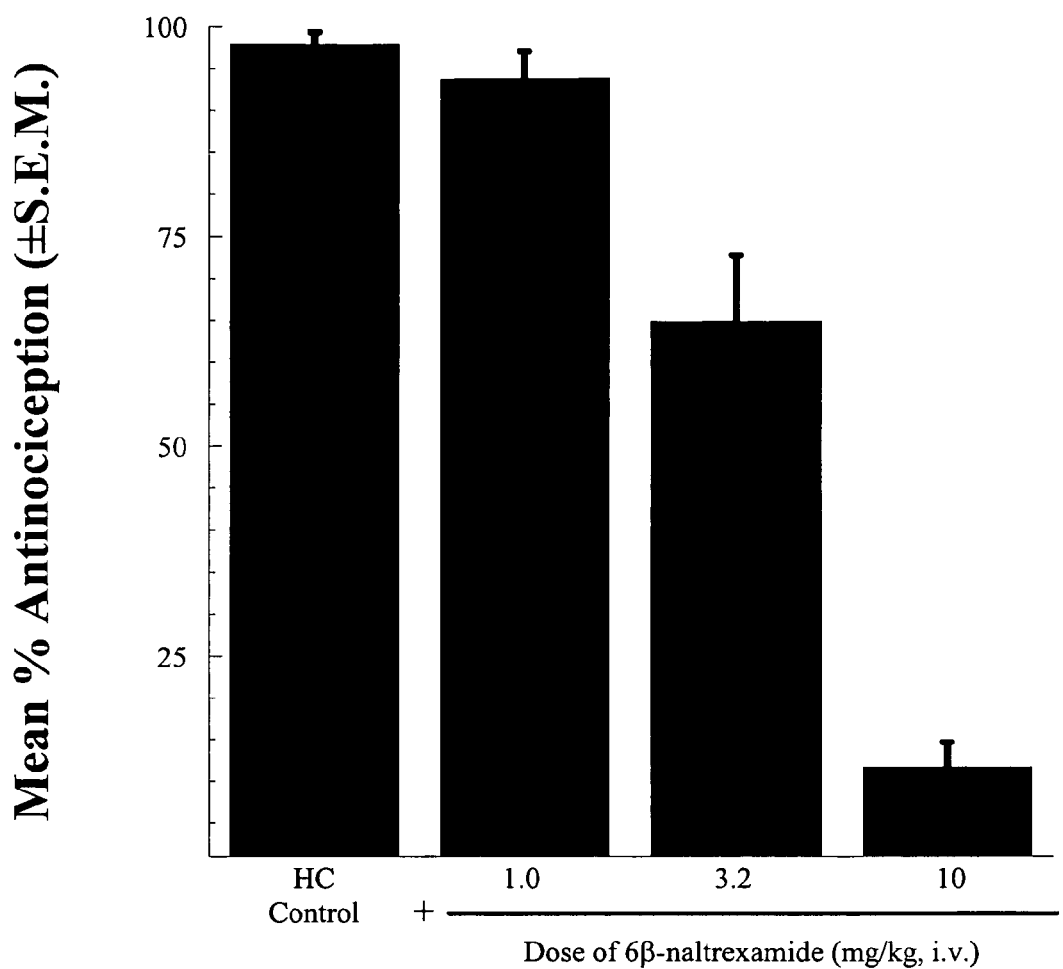
FIG. 8A is a dose response curve reflecting the potency of the inhibitive effects of intravenously-administered 6β-naltrexamide on an antinociceptive, intravenous dose of hydrocodone.
Figure 8B:
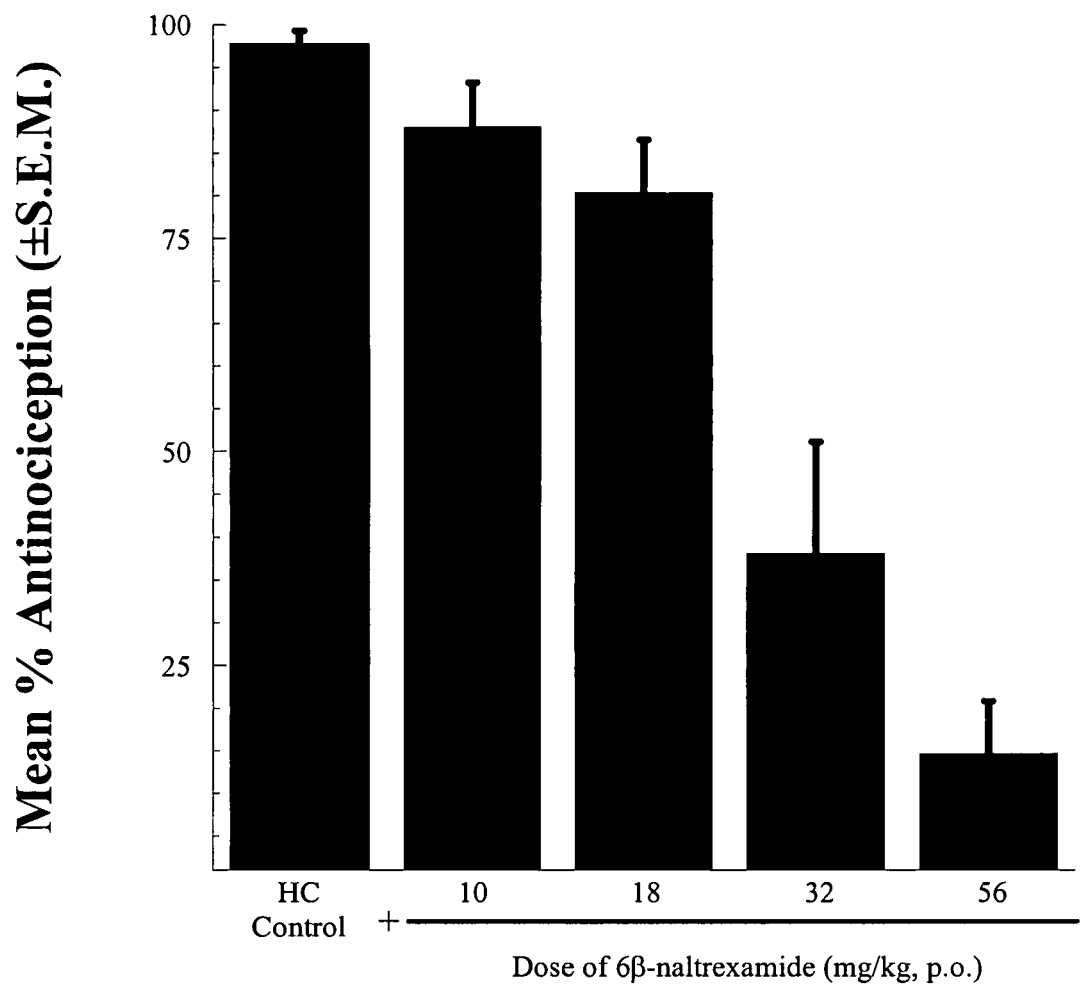
FIG. 8B is a dose response curve reflecting the potency of the inhibitive effects of orally-administered 6β-naltrexamide on an antinociceptive, intravenous dose of hydrocodone.

Both oral and i.v. potencies were determined by administering vehicle or various doses of 6β-naltrexamide at appropriate times prior to an $A_{90}$ dose of hydrocodone (3.2 mg/kg, i.v.). The respective i.v. (FIG. 8A) and p.o. (FIG. 8B) pretreatment times were 120 min. Mice were tested 10 min post hydrocodone injection (time of hydrocodone peak effect) in the 55° C. tail-flick assay. At least three doses were tested to produce a dose-response curve. The percent antinociception was then calculated for each dose and compared to hydrocodone controls.

These dose response curves were used to determine $ID_{50}$ value for 6β-naltrexamide. The percentage of inhibition, or reversal of the hydrocodone-induced antinociception, was calculated as (test−hydrocodone control)/(saline control−hydrocodone control)*100. From this data an $ID_{50}$ value (and 95% confidence interval) was calculated for each route using linear regression (FlashCalc software; Dr. Michael Ossipov, University of Arizona, Tucson, Ariz.). $ID_{50}$ values for 6β-naltrexamide inhibition of hydrocodone-induced antinociception were determined to be 4.06 mg/kg (95% CI=3.27-5.04) for i.v. administration, and 27.4 (22.6-33.2) for oral administration.

Antinociception Studies for Oral Co-Administration.

The tail-flick assay was used to construct full dose- and time-response summaries for 6β-naltrexamide in combination with hydrocodone. Vehicle or various doses of antagonist were orally co-administered with an $A_{90}$ dose of hydrocodone (32 mg/kg, p.o.) determined previously (data not shown). Tail-flick latencies were determined at t=10, 20, 30, 45, 60, 90, 120 and 180 minutes post injection (or until 20% MPE was reached) and % antinociception was calculated for each mouse (FIG. 9).

Figure 9:
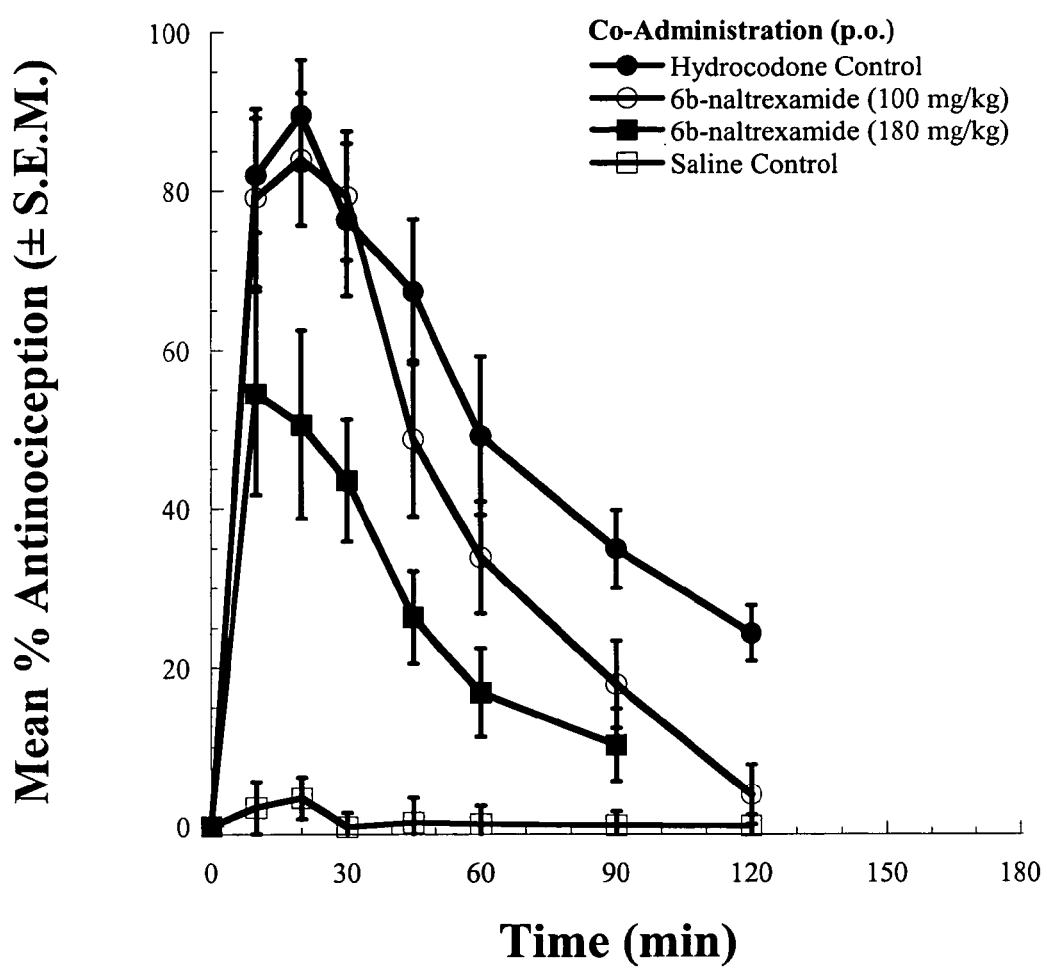
FIG. 9 is a graph that shows data reflecting the potency of the inhibitive effects of various concentrations of orally-administered 6β-naltrexamide on an orally-co-administered, antinociceptive dose of hydrocodone.

The experiments shown in FIG. 7-9 demonstrate that 6β-naltrexamide blocks hydrocodone-induced antinociception regardless of the route of administration, with a potency approximately 10-fold lower than that of 6β-naltrexol.

Effect of 6β-Naltrexamide on Hydrocodone-Induced Gastrointestinal Tract Slowing

Example 5

GI Transit Assay

Opioid-induced GI transit inhibition was measured using standard protocols as described above under Example 2.

GI Transit Studies for Determining 6β-Naltrexamide Potency.

Figure 10A:
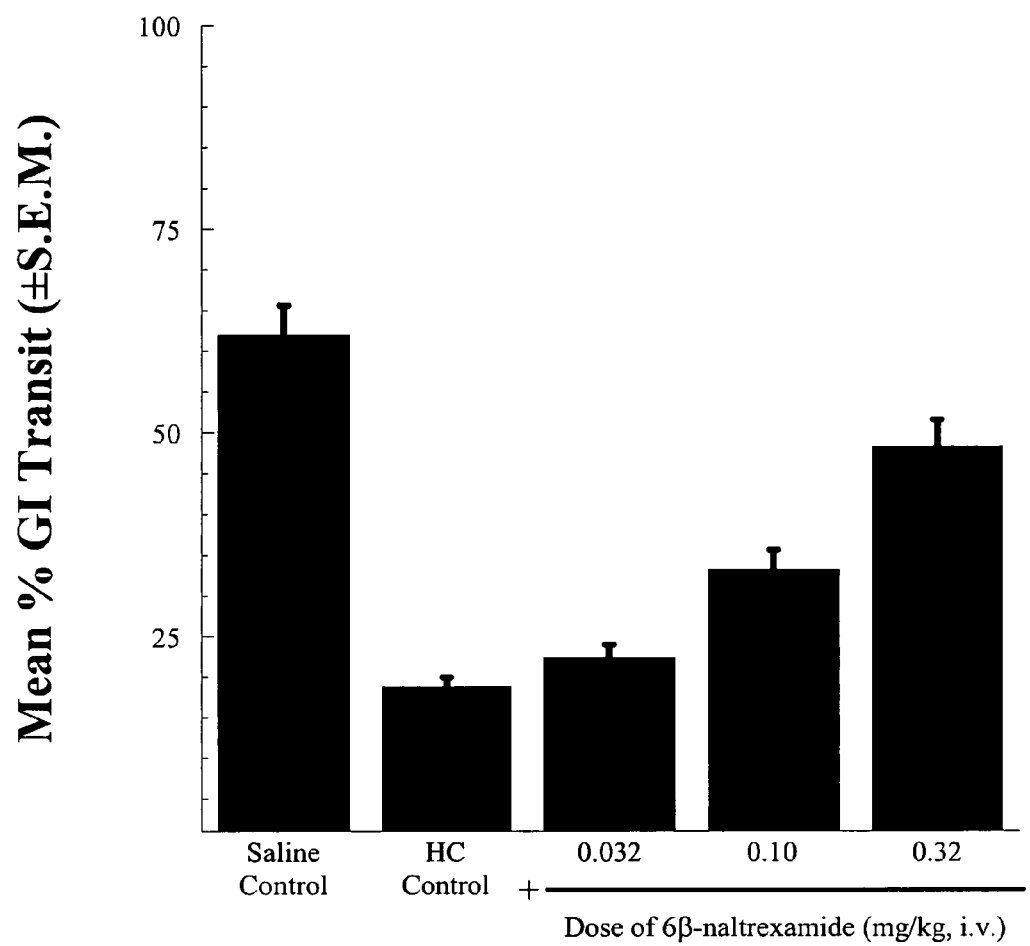
FIG. 10A is a dose response curve reflecting the potency of intravenously-administered 6β-naltrexamide to reverse hydrocodone-induced GI transit slowing, where the two compounds are not co-administered.
Figure 10B:
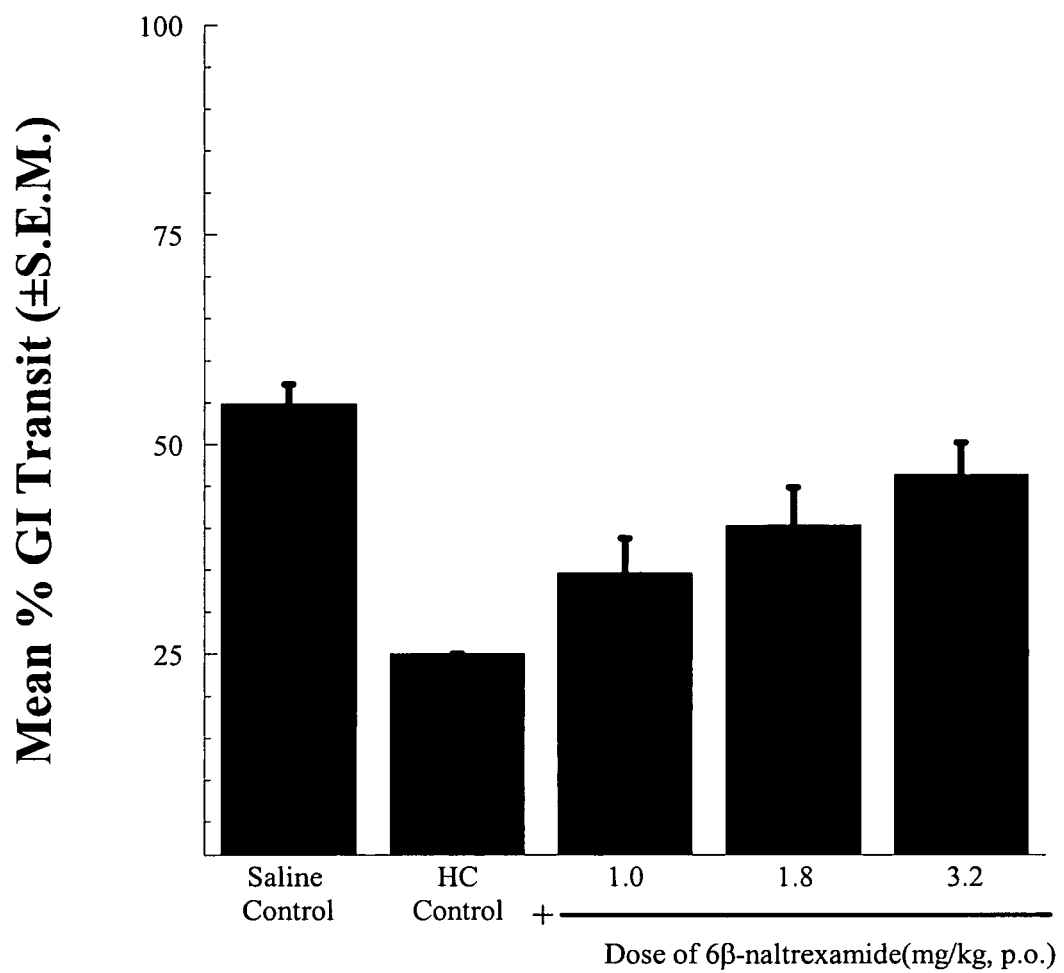
FIG. 10B is a dose response curve reflecting the potency of orally-administered 6β-naltrexamide to reverse hydrocodone-induced GI transit slowing, where the two compounds are not co-administered.

The ability of 6β-naltrexamide to block hydrocodone induced GI inhibition was assessed. Both i.v. (FIG. 10A) and oral potencies (FIG. 10B) were determined by administering vehicle or various doses of 6β-naltrexamide prior to an antinociceptive $A_{90}$ dose of hydrocodone (3.2 mg/kg, i.v.). The pretreatment times corresponded with the time of peak effect for the antinociception studies. The charcoal meal was given 10 min following the injection of hydrocodone. Vehicle (saline) controls were also assessed i.v. The percentage of GI transit was calculated for each mouse and a dose-response curve was constructed for the antagonist. At least three doses were used for each route and the results were compared to saline and hydrocodone controls.

$ID_{50}$ values were calculated for 6β-naltrexamide to determine potency to inhibit hydrocodone effects. 6β-naltrexamide and hydrocodone were administered at appropriate times so that time of peak effect (as determined in the tail-flick assay) occurred during charcoal administration. When given i.v. (FIG. 10A) and p.o. (FIG. 10B) 6β-naltrexamide dose-dependently reversed the inhibition of GI transit by hydrocodone ($A_{90}$ dose, i.v.), yielding $ID_{50}$ values of 0.173 (95% CI=0.131-0.230) and 1.92 (95% CI=1.03-3.56) for i.v. and p.o. administration, respectively.

GI Transit Studies for Oral Co-Administration.

Vehicle (saline) or various doses of 6β-naltrexamide are orally co-administered with an antinociceptive $A_{90}$ dose of hydrocodone (32 mg/kg, p.o.) 60 min prior to charcoal administration. This time is chosen so that the time of peak effect for the antagonist will occur during the intestinal transit of the charcoal meal. Vehicle (saline) controls are also assessed p.o. to compare the observed effects to opioid naïve mice. The percentage of GI transit is calculated for each mouse and a dose-response curve is constructed. At least three doses are used for each antagonist and the results are compared to saline and hydrocodone controls.

When given i.v. and p.o., 6β-naltrexamide is expected to dose-dependently reverse the inhibition of GI transit by hydrocodone and other analgesics with an $ID_{50}$ in the range of 0.1 to 0.2 mg/kg and 1 to 2 mg/kg for i.v. and p.o. administration, respectively.

Statistical Analysis.

The dose-response curves shown in FIG. 7-10 were used to estimate and compare central (antinociception) to peripheral (GI transit) potencies of 6β-naltrexamide. The percentage of inhibition or reversal of the hydrocodone effect in either assay was determined for each mouse in the 6β-naltrexamide groups. The percent reversal was calculated as (test−hydrocodone control)/(saline control−hydrocodone control)*100. From this data an $ID_{50}$ value (and 95% confidence interval) was calculated for each route/antagonist/assay using linear regression (FlashCalc software; Dr. Michael Ossipov, University of Arizona, Tucson, Ariz.).

Potency of 6β-Naltrexamide for Slowing GI-Transit and for Reversing Antinociception.

Figure 11A:
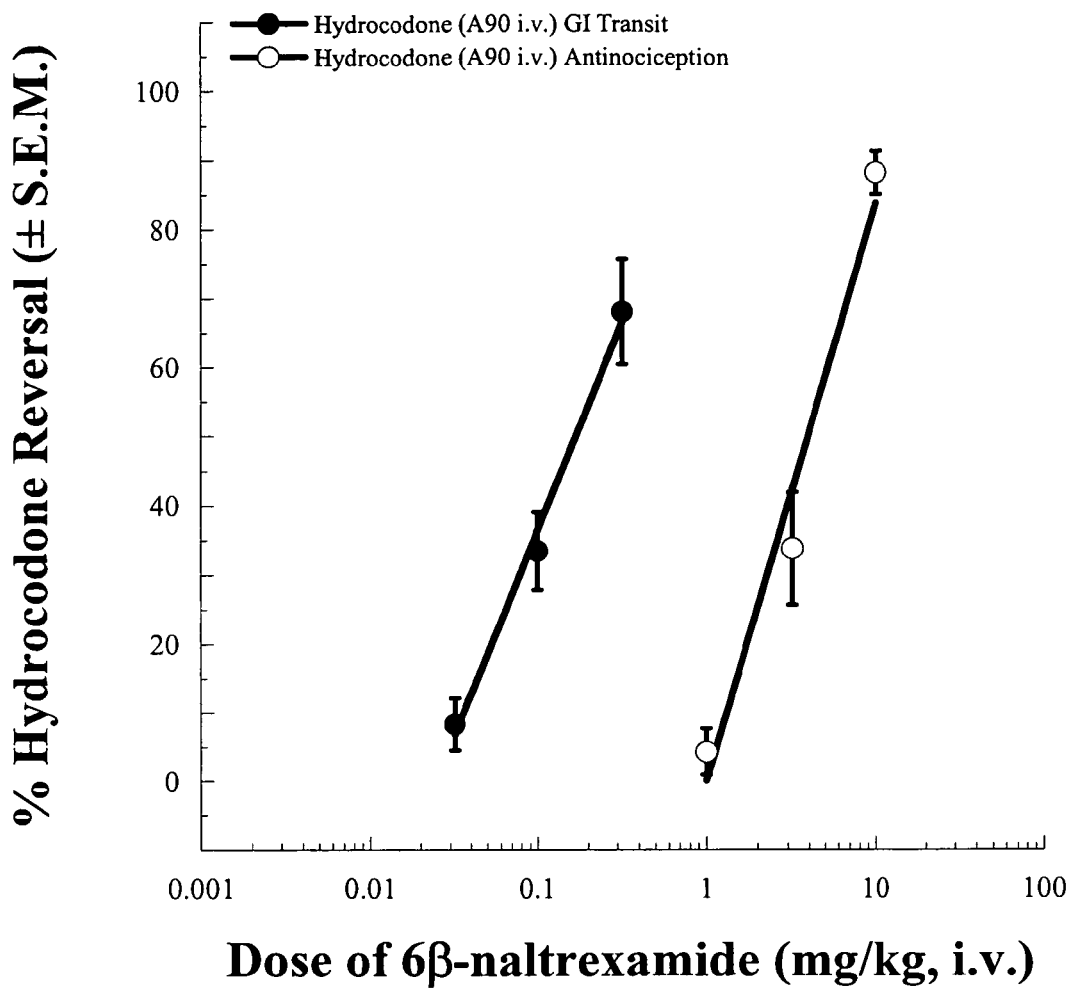
FIG. 11A shows the summarized potency data for inhibition of hydrocodone activity by 6β-naltrexamide in GI transit studies (peripheral effects) and antinociception studies (central effects), where both 6β-naltrexamide and hydrocodone were administered intravenously at different times.

Comparison of the calculated potencies (ID50) for 6β-naltrexamide to reverse either the central effects, antinociception, or peripheral effects, GI-transit slowing, induced by hydrocodone, led to the surprising discovery that 6β-naltrexamide is 14-25-fold more potent peripherally than centrally. FIGS. 11A and B demonstrate this potency difference showing data derived from the dose response curves described above.

Figure 11B:
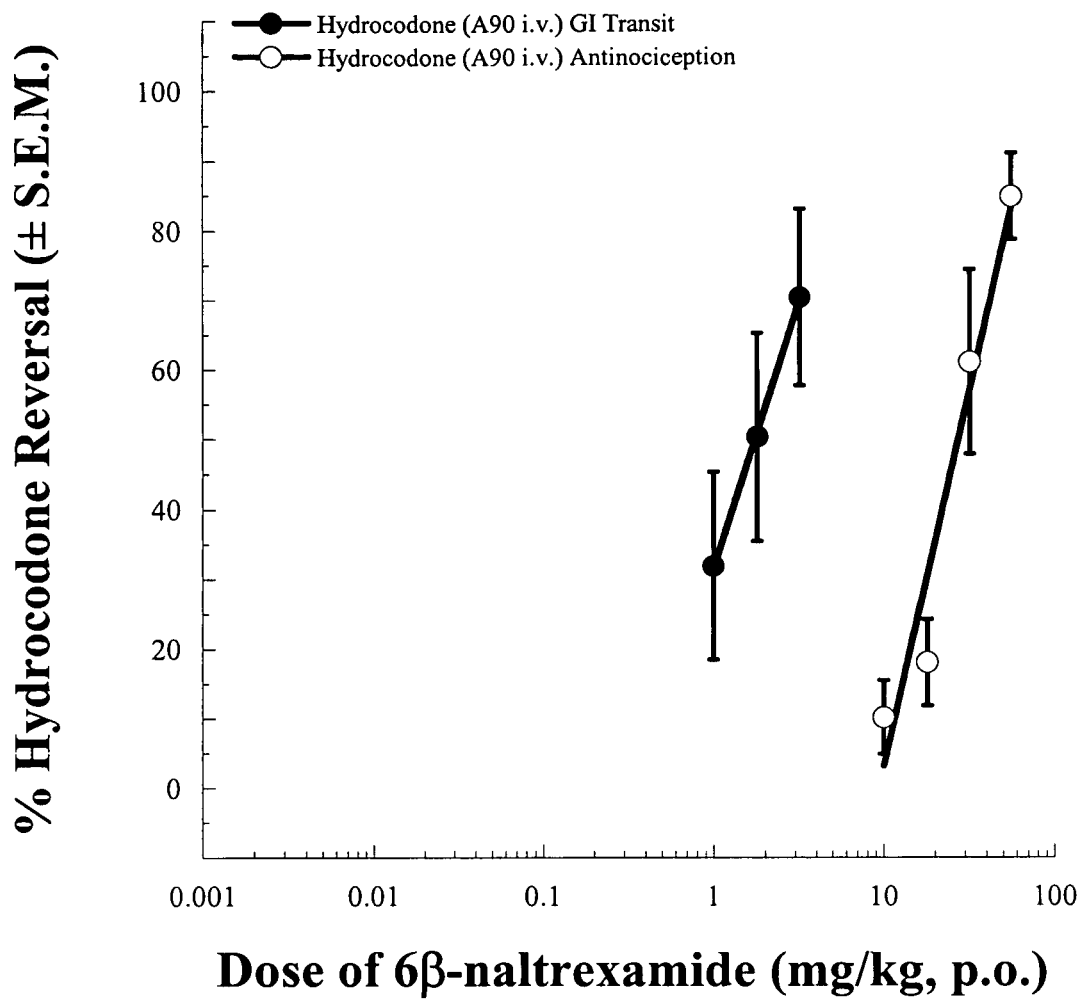
FIG. 11B shows the summarized potency data for inhibition of hydrocodone activity by 6β-naltrexamide in the GI transit studies (peripheral effects) and antinociception studies (central effects), where 6β-naltrexamide was administered orally and hydrocodone was administered intravenously at different times.

6β-naltrexamide was found to have significant shifts in potency between the two assays for all injection parameters. I.v. (FIG. 11A, Table 3) administration of 6β-naltrexamide was approximately 23-times more potent at reversing GI effects of i.v. hydrocodone than antinociceptive effects while orally administered 6β-naltrexamide demonstrated 14-fold more potency for reversing GI effects compared to antinociceptive effects (FIG. 11B, Table 3). These data suggest that 6β-naltrexamide is significantly more potent at inhibiting the peripheral effects than the central effects induced by opioids. Furthermore, oral co-administration with hydrocodone is expected to show a 10-25-fold and potentially up to a 50-fold shift in potency as well.

Thus, it is anticipated that 6β-naltrexamide will be 10-25-fold, and potentially 50-fold, more potent for slowing GI-transit than for reversing antinociception when both drugs are administered orally, so could be utilized for therapeutic use. The 6β-naltrexamide exhibited a much larger potency shift than predicted from its chemical structure, suggesting that 6β-naltrexamide may be actively prevented from entering, or is transported out of, the CNS compared to 6β-naltrexol, and thus may provide a larger therapeutic window than 6β-naltrexol.

TABLE 3

The fold-shift in peripheral vs. central potency was calculated and is shown as (antinociception $ID_{50}$)/(GI transit $ID_{50}$). A fold-shift less than 1.0 indicates a greater central potency over peripheral potency.

| Drug Combination | GI Transit $ID_{50}$ (95% CI) (mg/kg) | Antinociception $ID_{50}$ (95% CI) (mg/kg) | Fold-Shift |
|---|---|---|---|
| 6β-naltrexamide (i.v.)/ Hydrocodone (i.v.) | 0.173 (0.131-0.230) | 4.06 (3.27-5.04) | 23.5 |
| 6β-naltrexamide (p.o.)/ Hydrocodone (i.v.) | 1.92 (1.03-3.56) | 27.4 (22.6-33.2) | 14.3 |
| 6β-naltrexamide (p.o.)/ Hydrocodone (p.o.)* | 1-2 | 3-5 | 10-50 |

*Predicted

Effect of Naltrexone, a Well-Known and Characterized Antagonist, on Hydrocodone-Induced Antinociception.

Experiments with naltrexone illustrate the significant differences between the compounds taught by this application and known, characterized antagonists.

Example 6

Tail Flick Assay

The tail-flick assay was used to measure antinociception as described above under Example 1.

Antinociception Studies for Determining Time of Peak Effect of Naltrexone.

Figure 12A:
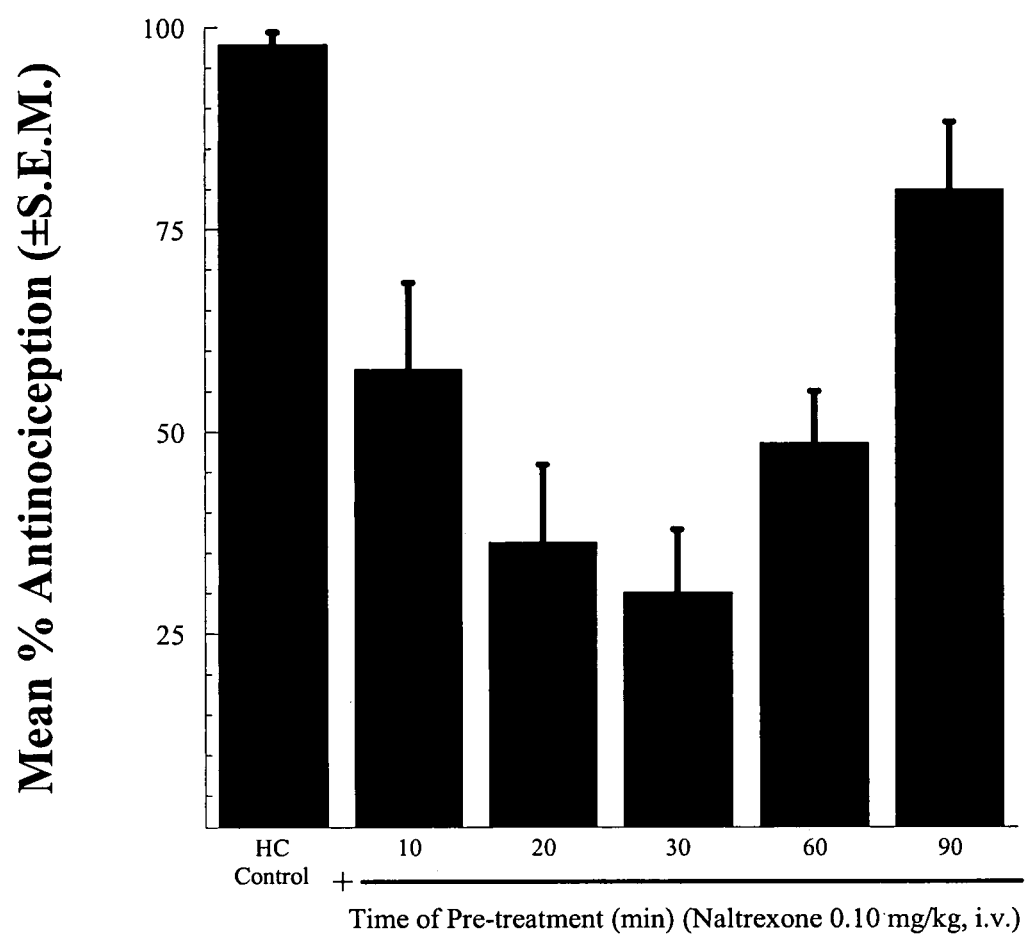
FIG. 12A is a graph that shows data reflecting the duration of the inhibitive effects of intravenously-administered naltrexone on an antinociceptive, intravenous dose of hydrocodone, and demonstrates the time of peak effect of antinociception inhibition.
Figure 12B:
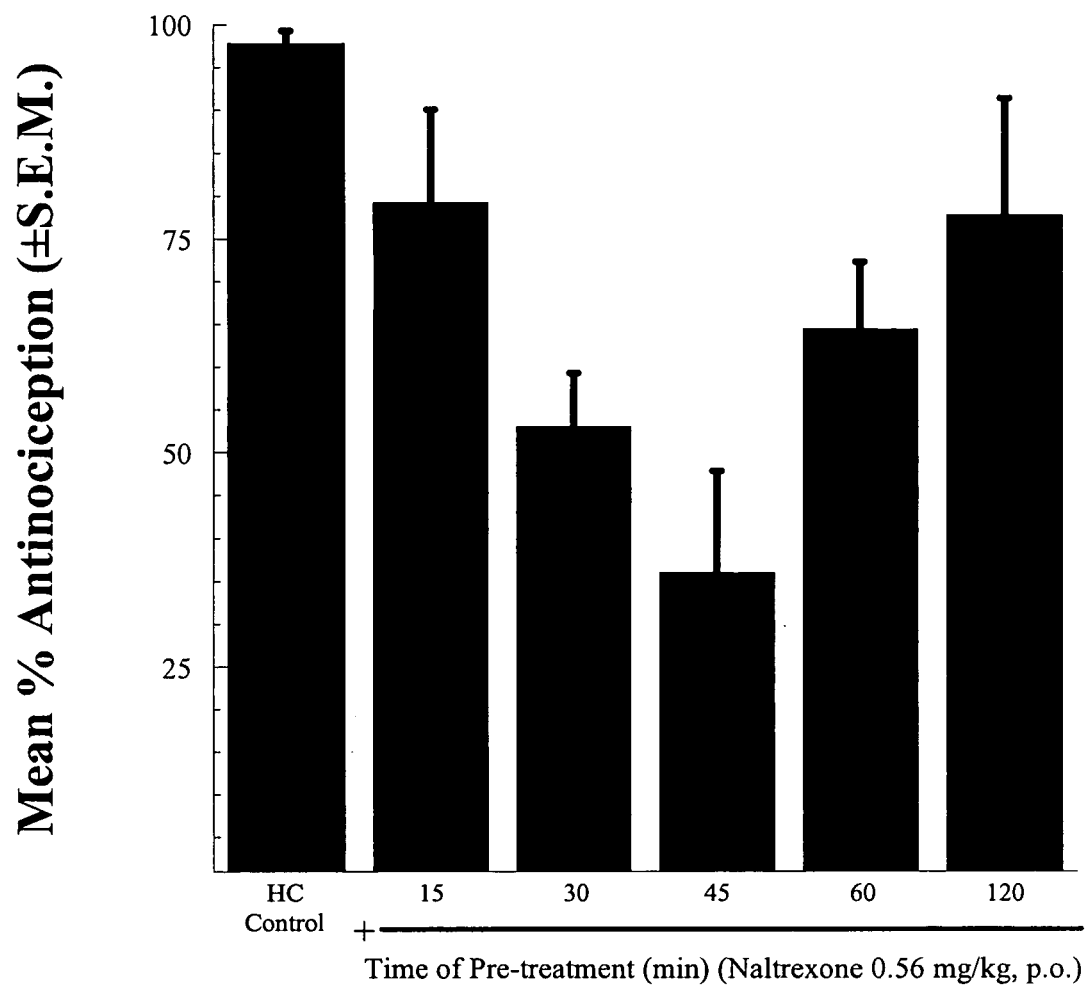
FIG. 12B is a graph that shows data reflecting the duration of the inhibitive effects of orally-administered naltrexone on an antinociceptive, intravenous dose of hydrocodone, and demonstrates the time of peak effect of antinociception inhibition.

The duration of naltrexone effects were measured by pre-treating mice with naltrexone at various times prior to an injection of an antinociceptive $A_{90}$ dose of hydrocodone (3.2 mg/kg, i.v., dose determined previously; data not shown). Mice were tested 10 min later at time of peak effect for hydrocodone in the tail-flick assay. Naltrexone doses of 0.10 mg/kg for i.v. (FIG. 12A) and 0.56 mg/kg for p.o. (FIG. 12B) were used.

Figure 13A:
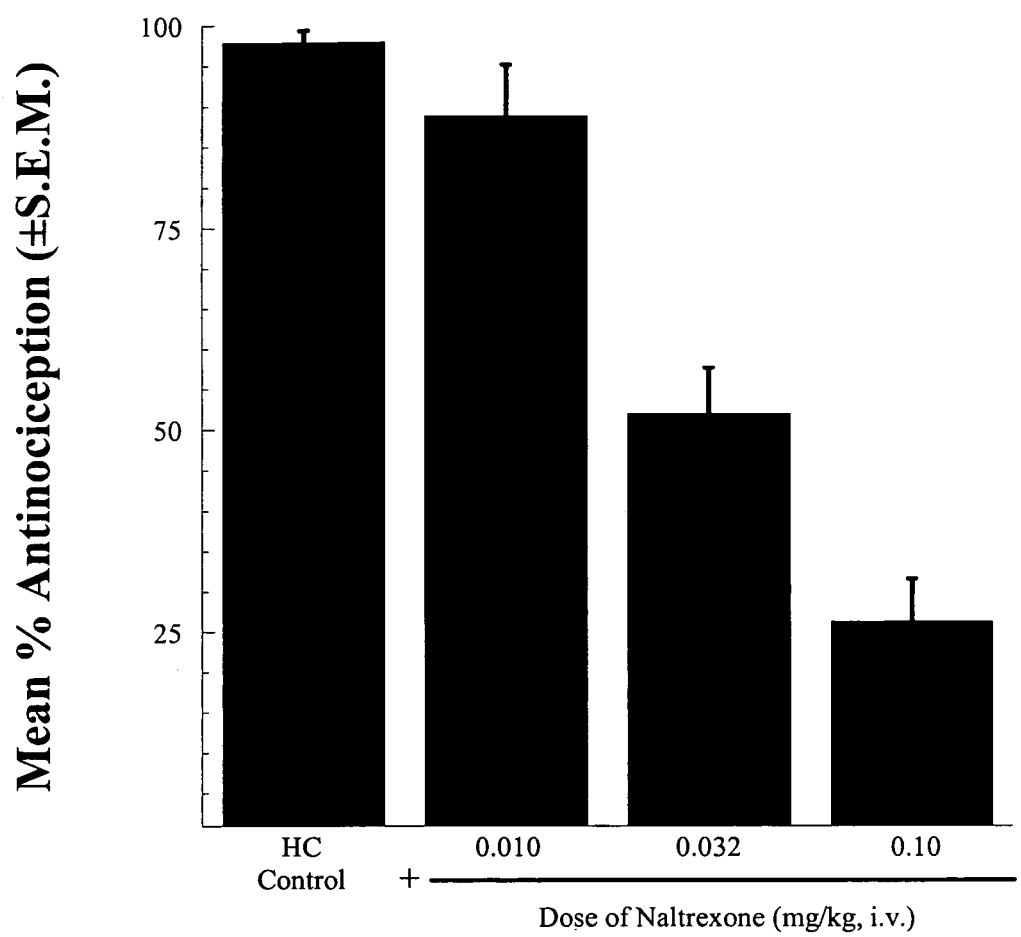
FIG. 13A is a dose response curve reflecting the potency of the inhibitive effects of intravenously-administered naltrexone on an antinociceptive, intravenous dose of hydrocodone.
Figure 13B:
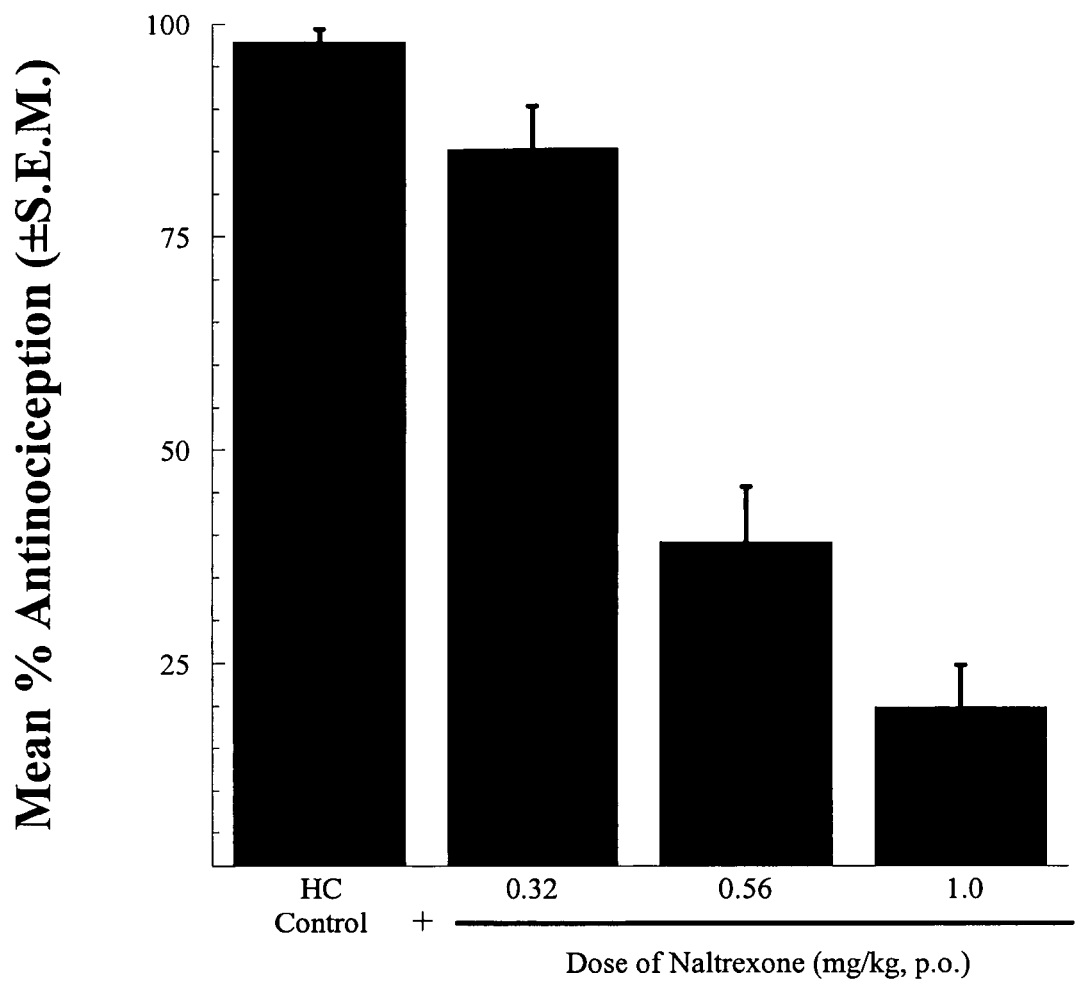
FIG. 13B is a dose response curve reflecting the potency of the inhibitive effects of orally-administered naltrexone on an antinociceptive, intravenous dose of hydrocodone.

These time ranging experiments illustrate that naltrexone was capable of reversing the centrally mediated antinociceptive effects of hydrocodone (FIGS. 13A and 13B), with a time of peak effect at 30 min for i.v. administration and 45 min when administered p.o.

Antinociception Studies for Determining Antagonist Potencies.

Both oral and i.v. potencies were determined by administering vehicle or various doses of naltrexone at appropriate times prior to an $A_{90}$ dose of hydrocodone (3.2 mg/kg, i.v.). The respective i.v. (FIG. 13A) and p.o. (FIG. 13B) pretreatment times were 30 and 45 min. Mice were tested 10 min post hydrocodone injection (time of hydrocodone peak effect) in the 55° C. tail-flick assay. At least three doses were tested to produce a dose-response curve. The percent antinociception was then calculated for each dose and compared to hydrocodone controls.

These dose response curves were used to determine $ID_{50}$ value for naltrexone in these experiments for comparison purposes. The percentage of inhibition or reversal of the hydrocodone-induced antinociception was calculated as (test−hydrocodone control)/(saline control−hydrocodone control)*100. From this data an $ID_{50}$ value (and 95% confidence interval) was calculated for each route using linear regression (FlashCalc software; Dr. Michael Ossipov, University of Arizona, Tucson, Ariz.). $ID_{50}$ values for naltrexone inhibition of hydrocodone-induced antinociception were determined to be 0.0411 (0.0319-0.0529) for i.v. administration, and 0.534 (0.471-0.605) for oral administration. These values are consistent with published values for the oral bioavailability of naltrexone and with the published observation that 6β-naltrexol is approximately 5-10-fold less potent than naltrexone for reversing morphine-induced antinociception (Wang D., Raehal K. M., Lin E. T., Lowery J. J., Kieffer B. L., Bilsky E. J., Sadee W. (2004 February Epub 2003 Nov. 4) "Basal signaling activity of mu opioid receptor in mouse brain: role in narcotic dependence," *J Pharmacol Exp Ther.*; 308(2):512-20; Raehal K. M., Lowery J. J., Bhamidipati C. M., Paolino R. M., Blair J. R., Wang D., Sadee W., Bilsky E. J. (2005 June; Epub 2005 Feb. 16), depending on route of administration.

Antinociception Studies for Oral Co-Administration.

Figure 15A:
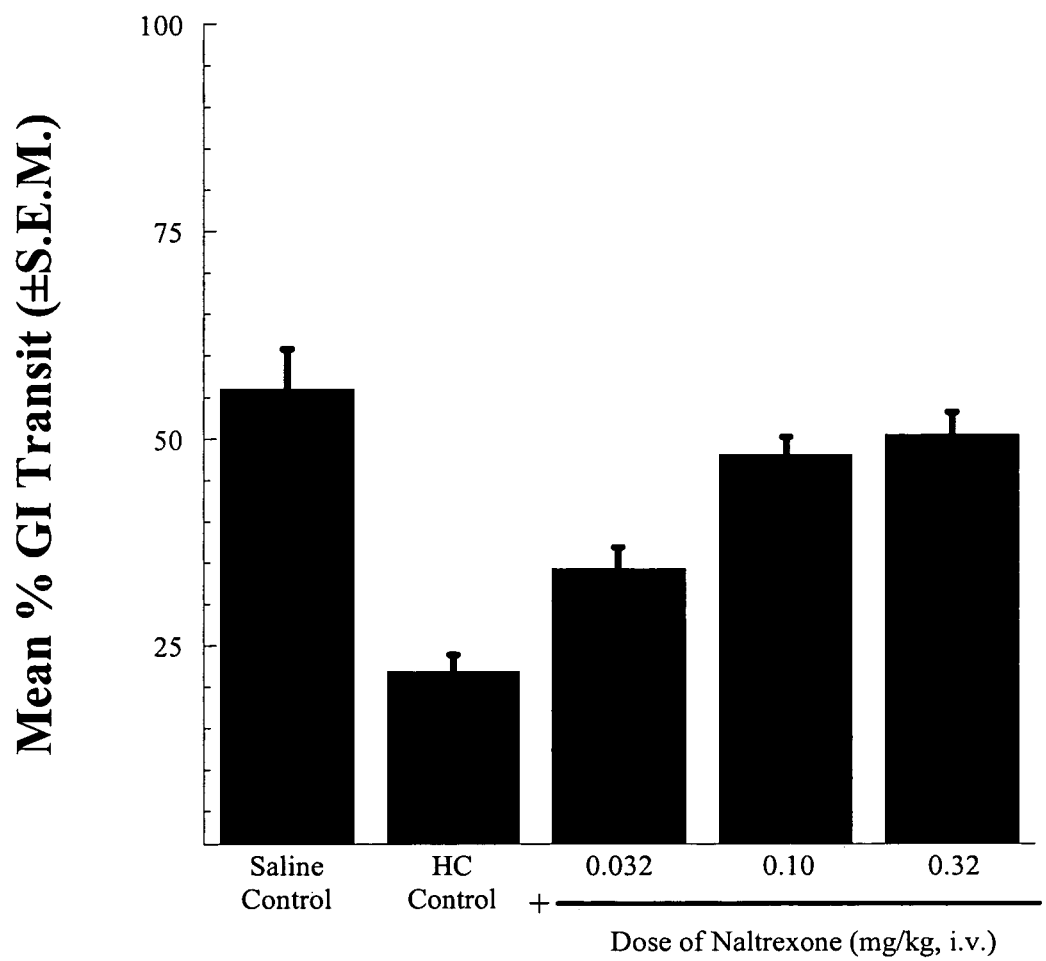
FIG. 15A is a dose response curve reflecting the potency of intravenously-administered naltrexone to reverse hydrocodone-induced GI transit slowing.
Figure 15B:
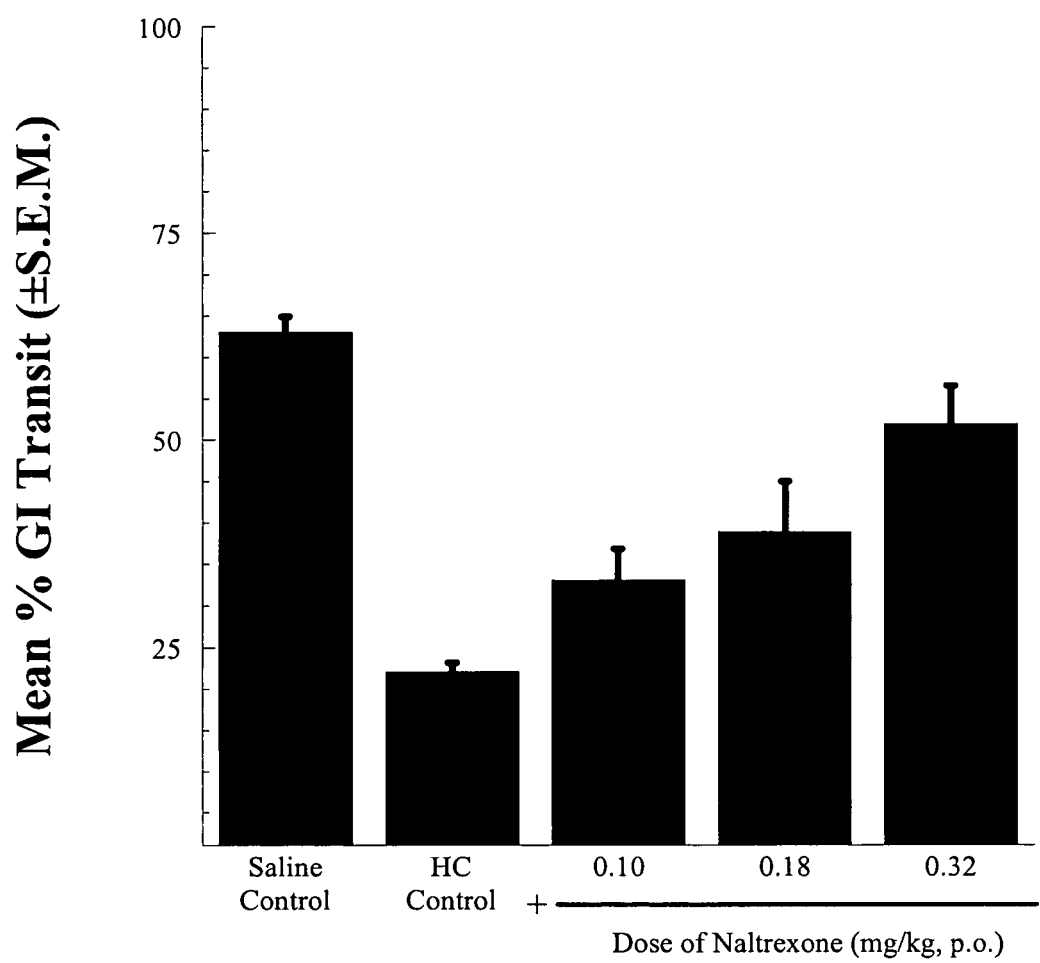
FIG. 15B is a dose response curve reflecting the potency of orally-administered naltrexone to reverse hydrocodone-induced GI transit slowing.

The tail-flick assay was used to construct full dose- and time-response summaries for naltrexone in combination with hydrocodone. Vehicle or various doses of antagonist were orally co-administered with an $A_{90}$ dose of hydrocodone (32 mg/kg, p.o.) determined previously (data not shown). Tail-flick latencies were determined at t=10, 20, 30, 45, 60, 90, 120 and 180 minutes post injection (or until 20% MPE was reached) and % antinociception was calculated for each mouse (FIG. 15).

Figure 14:
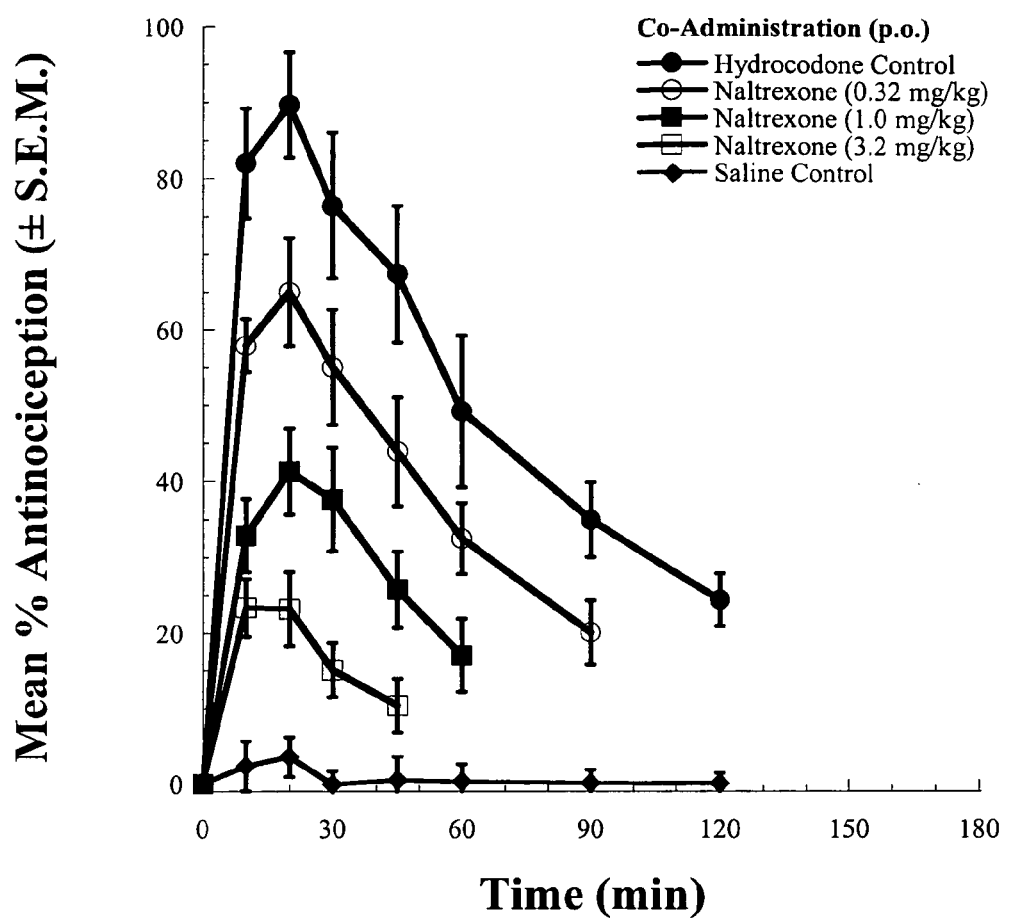
FIG. 14 is a graph that shows data reflecting the potency of the antinociception-inhibitive effects of various concentrations of orally-administered naltrexone on an orally-co-administered, antinociceptive dose of hydrocodone.

The antinociception experiments shown in FIG. 14 yield an $ID_{50}$ value of 0.914 mg/kg (95% CI=3.27-5.04) for naltrexone co-administered with hydrocodone.

The experiments shown in FIG. 12-14 demonstrate that naltrexone blocks hydrocodone-induced antinociception regardless of the route of administration, consistent with the many published reports on naltrexone and its clinical use for the treatment of alcoholism and opioid addiction.

Effect of Naltrexone on Hydrocodone-Induced Gastrointestinal Tract Slowing

Example 7

GI Transit Assay

Opioid-induced GI transit inhibition was measured using standard protocols as described above under Example 2.

GI Transit Studies for Determining Naltrexone Potency.

The ability of naltrexone to block hydrocodone-induced GI inhibition was assessed. Both i.v. (FIG. 15A) and oral potencies (FIG. 15B) were determined by administering vehicle or various doses of naltrexone prior to an antinociceptive $A_{90}$ dose of hydrocodone (3.2 mg/kg, i.v.). The pretreatment times corresponded with the time of peak effect for the antinociception studies. The charcoal meal was given 10 min following the injection of hydrocodone. Vehicle (saline) controls were also assessed i.v. The percentage of GI transit was calculated for each mouse and a dose-response curve was constructed. At least three doses were used for each route and the results were compared to saline and hydrocodone controls.

$ID_{50}$ values were calculated for naltrexone to determine potency to inhibit hydrocodone effects. Naltrexone and hydrocodone were administered at appropriate times so that time of peak effect (as determined in the tail-flick assay) occurred during charcoal administration. When given by i.v. (FIG. 15a) and p.o. (FIG. 15b) naltrexone dose-dependently reversed the inhibition of GI transit by hydrocodone ($A_{90}$ dose, i.v.), yielding $ID_{50}$ values of 0.0456 (95% CI=0.0275-0.0757) for i.v. and 0.194 (95% CI=0.136-0.277) for p.o. administration, respectively.

GI Transit Studies for Oral Co-Administration.

Figure 16:
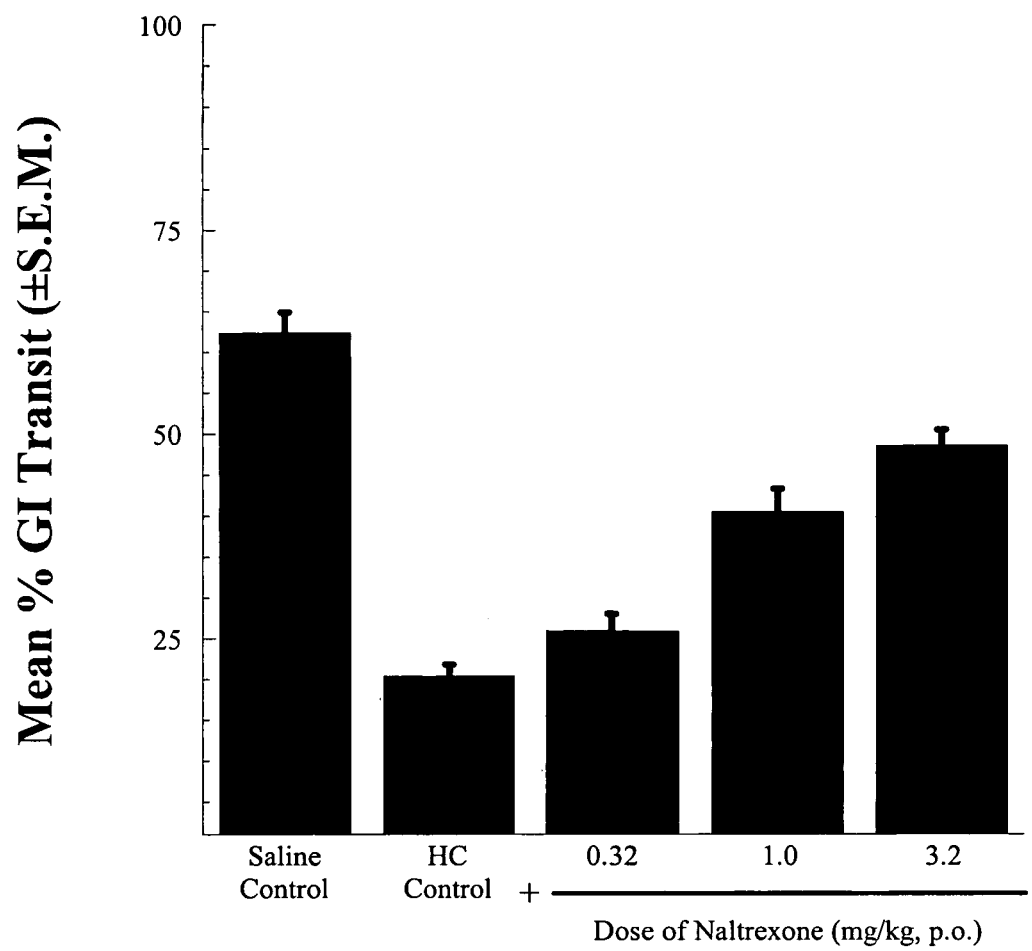
FIG. 16 is a dose response curve reflecting the potency of naltrexone to reverse hydrocodone-induced GI transit slowing when the two compounds are orally co-administered.

Vehicle (saline) or various doses of naltrexone was orally co-administered with an antinociceptive $A_{90}$ dose of hydrocodone (32 mg/kg, p.o.) 15 min prior to charcoal administration (FIG. 16). This time was chosen so that the time of peak effect for the antagonist would occur during the GI transit of the charcoal meal. Vehicle (saline) controls were also assessed p.o. to compare the observed effects to opioid naïve mice. The percentage of GI transit was calculated for each mouse and a dose-response curve was constructed. At least three doses were used for each antagonist and the results were compared to saline and hydrocodone controls.

Naltrexone orally co-administered with hydrocodone ($A_{90}$ dose, p.o.) again dose-dependently reversed GI inhibition (FIG. 16) with an $ID_{50}$ of 1.40 mg/kg (95% CI=1.07-1.84).

Statistical Analysis.

The dose-response curves shown in FIG. 13-16 were used to estimate and compare central (antinociception) to peripheral (GI transit) potencies for naltrexone. The percentage of inhibition or reversal of the hydrocodone effect in either assay was determined for each mouse in the naltrexone groups. The percent reversal was calculated as (test−hydrocodone control)/(saline control−hydrocodone control)*100. From this data an $ID_{50}$ value (and 95% confidence interval) was calculated for each route/antagonist/assay using linear regression (FlashCalc software; Dr. Michael Ossipov, University of Arizona, Tucson, Ariz.).

Potency of Naltrexone for Slowing GI-Transit and for Reversing Antinociception.

Comparison of the calculated potencies ($ID_{50}$) for naltrexone to reverse either the central effects, antinociception, or peripheral effects, GI-transit slowing, demonstrated that naltrexone was nearly equipotent peripherally and centrally.

Figure 17A:
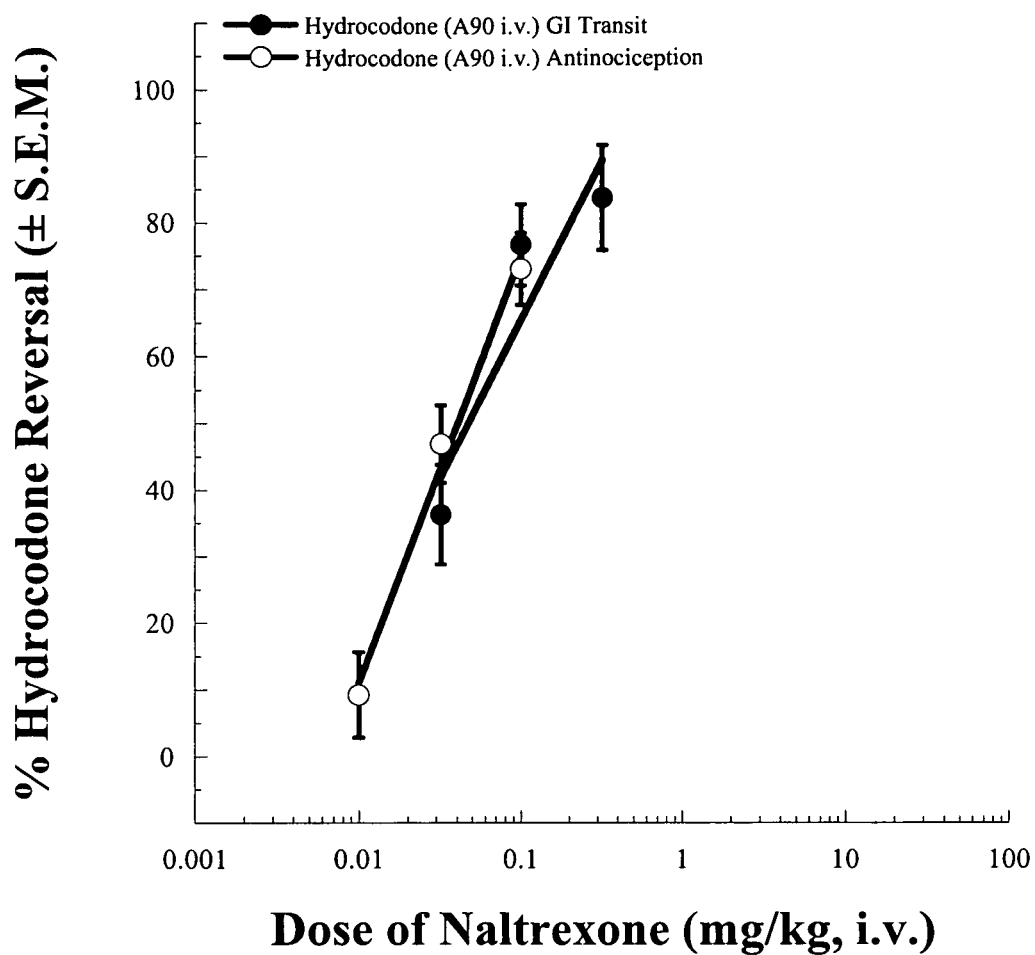
FIG. 17A shows the summarized potency data for inhibition of the effects of intravenously-administered hydrocodone by intravenously-administered naltrexone in the GI transit studies (peripheral effects) and antinociception studies (central effects).
Figure 17B:
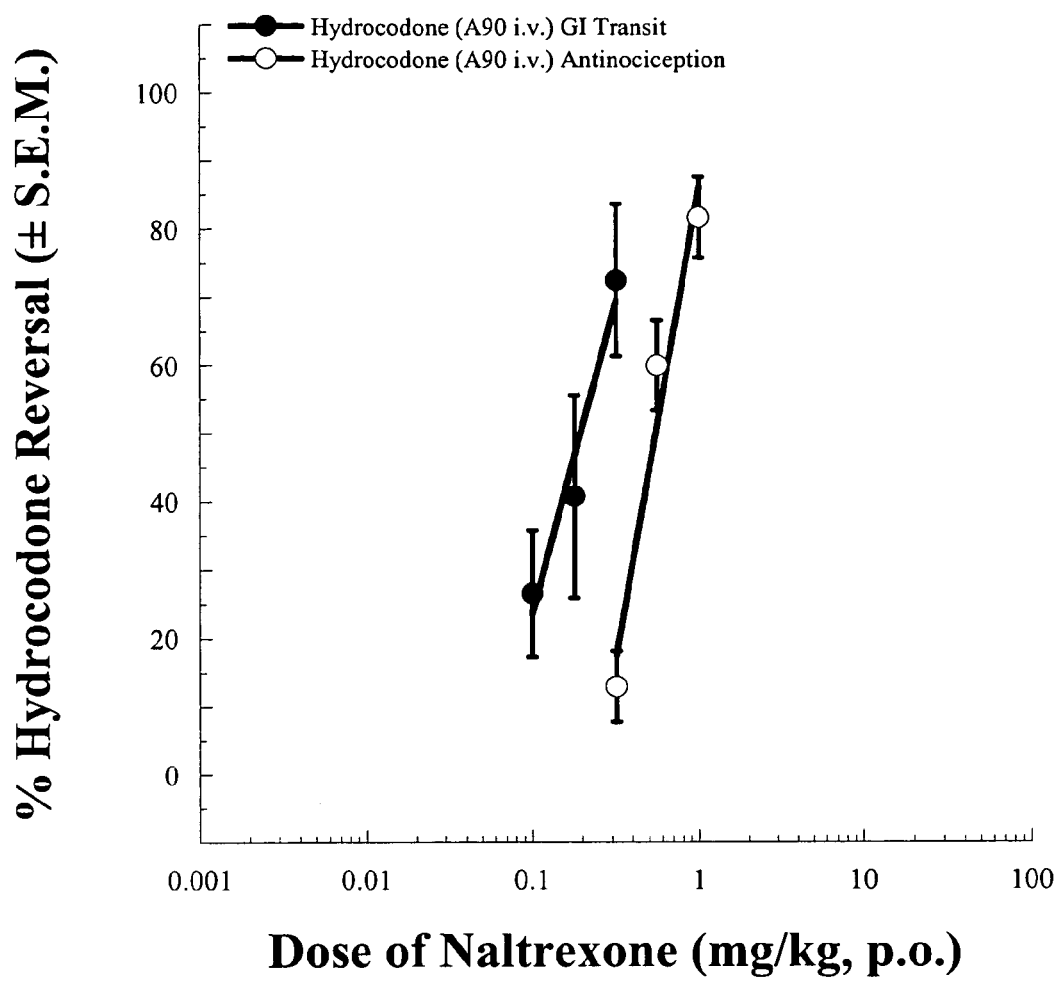
FIG. 17B shows the summarized potency data for inhibition of the effects of intravenously-administered hydrocodone by orally-administered naltrexone in the GI transit studies (peripheral effects) and antinociception studies (central effects).

FIG. 17A-B illustrate the potency differences showing data derived from the dose response curves described above.

Figure 17C:
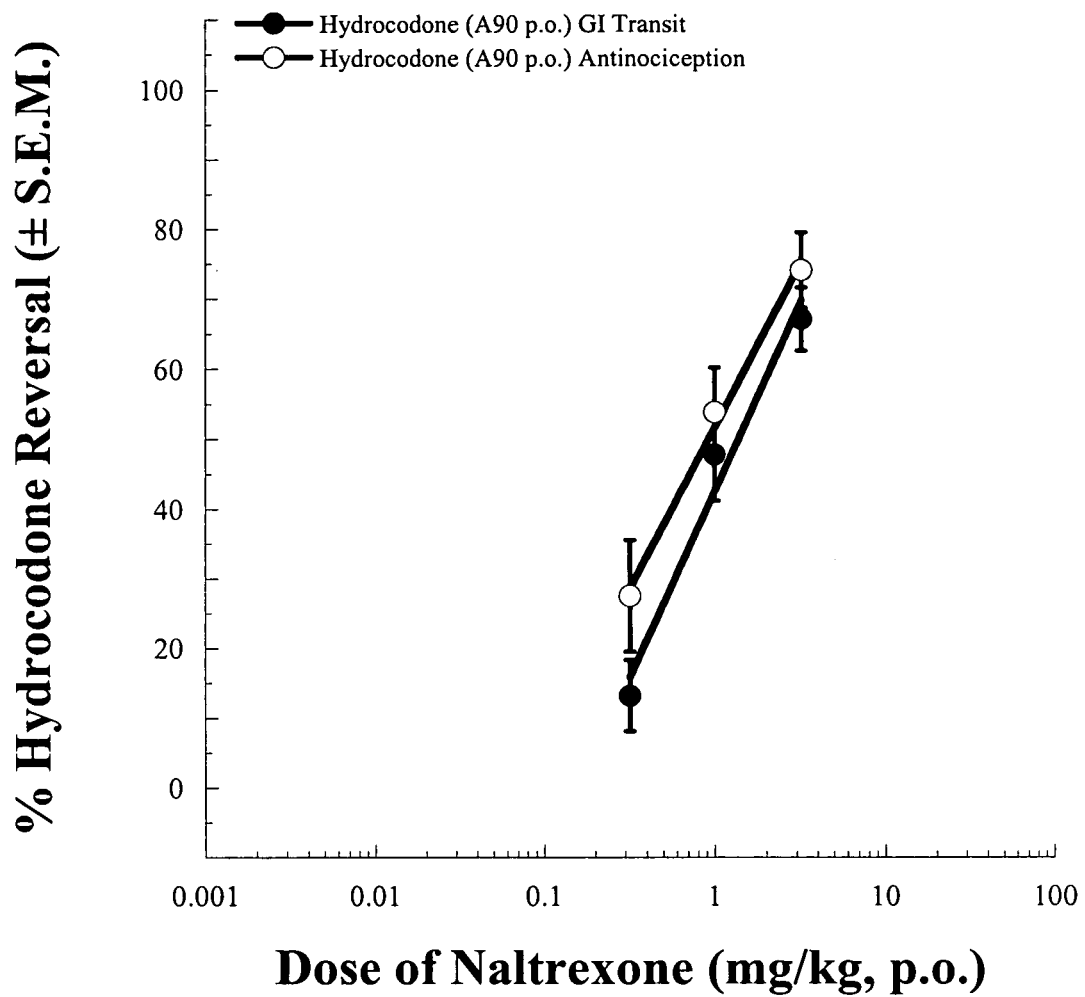
FIG. 17C shows the summarized potency data for inhibition of the effects of hydrocodone by naltrexone in the GI transit studies (peripheral effects) and antinociception studies (central effects) where both compounds are orally co-administered.

Naltrexone was found to have small or negligible shifts in potency between the two assays for all injection parameters. I.v. (FIG. 17A, Table 4) administration of naltrexone was approximately equipotent at reversing GI effects of i.v. hydrocodone than antinociceptive effects while orally administered naltrexone demonstrated only a 3-fold difference in potency for reversing GI effects compared to antinociceptive effects (FIG. 17B, Table 4). Furthermore, oral co-administration with hydrocodone resulted in a 0.6-fold shift in potency, actually exhibiting more central than peripheral potency (FIG. 17C, Table 4). These data suggest that naltrexone is nearly equipotent for inhibiting peripheral effects and central effects induced by opioids, consistent with its medicinal use as a treatment for alcoholism and opioid addiction.

TABLE 4

The fold-shift in peripheral vs. central potency was calculated and is shown in Table 4 as (antinociception $ID_{50}$)/(GI transit $ID_{50}$). A fold-shift less than 1.0 indicates a greater central potency over peripheral potency.

| Drug Combination | GI Transit $ID_{50}$ (95% CI) (mg/kg) | Antinociception $ID_{50}$ (95% CI) (mg/kg) | Fold-Shift |
|---|---|---|---|
| Naltrexone (i.v.)/ Hydrocodone (i.v.) | 0.0456 (0.0275-0.0757) | 0.0411 (0.0319-0.0529) | 0.901 |
| Naltrexone (p.o.)/ Hydrocodone (i.v.) | 0.194 (0.136-0.277) | 0.534 (0.471-0.605) | 2.75 |
| Naltrexone (p.o.)/ Hydrocodone (p.o.) | 1.40 (1.07-1.84) | 0.914 (0.628-1.33) | 0.653 |

These data illustrate the difference in activity between known, clinically used antagonists and the novel activities of the neutral antagonists taught in this application.

Moreover, a strong induction of diarrhea was present with administration of naltrexone, but was absent with naltrexol and naltrexamide.

What is claimed is:

1. A unit dosage of an analgesic composition comprising:
an opioid agonist in an amount sufficient to confer analgesia in a mammalian subject; and
a neutral opioid antagonist in an amount sufficient to substantially inhibit peripheral effects, and insufficient to block substantial central effects, of the opioid agonist in the subject, wherein the agonist and antagonist are selected so that a ratio of antinociception ID50 to GI transit ID50 for the agonist and the antagonist is between about 5 and about 50.

2. A unit dosage of analgesic composition according to claim 1, wherein the opioid agonist is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, noroxycodone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tilidine and tramadol.

3. A unit dosage of an analgesic composition according to claim 2, wherein the subject is a human.

4. A unit dosage of an analgesic composition according to claim 3, such composition being suitable for oral, peroral, intragastric, sublingual, suppository, or intravenous administration.

5. A unit dosage according to claim 4, wherein the neutral opioid antagonist has a blood half-life substantially longer than the blood half-life of the opioid agonist, so that repeated administration of the dosage or administration above a prescribed dosage causes a greater increase in blood concentration of the antagonist than of the agonist, so as to deter diversion, discourage abuse and/or reduce addiction liability to the agonist resulting from such administration.

6. A unit dosage according to claim 4, wherein the neutral opioid antagonist and/or agonist are suitable for formulation in a slow-release formulation, slow-release co-formulation, or are formulated in a slow-release formulation or co-formulation, either separately or together.

7. A unit dosage of an analgesic composition according to claim 1 wherein the opioid agonist is hydrocodone.

8. A unit dosage according to claim 1 that deters abuse of the opioid agonist, wherein the opioid agonist has a blood half-life; and the neutral opioid antagonist has a blood half-life substantially longer than the blood half-life of the opioid agonist and is also present in an amount effective so that, upon successive administration of the unit dosage, the blood concentration ratio of neutral opioid antagonist to opioid agonist increases with each successive administration until a steady state is reached, as measured in mg per kg of body weight of the subject, and repeated administration of the unit dosage exceeding therapeutically recommended limits results in reduced euphoria and reduced pain relief in the subject so as to deter abuse.

9. A pharmaceutical composition according to claim 8, wherein the neutral opioid antagonist and/or agonist are suitable for formulation in a slow-release formulation, slow-release co-formulation, or are formulated in a slow-release formulation or co-formulation, either separately or together.

10. A unit dosage according to claim 1, wherein the opioid antagonist is a naltrexone analog represented by formula Iα or Iβ:

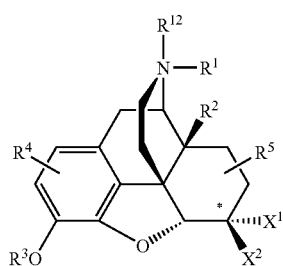

(Iα)

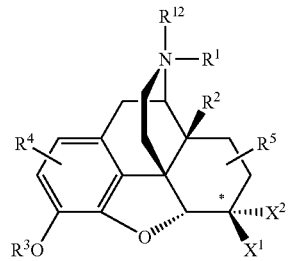

(Iβ)

wherein:
R$^1$ is $C_3$-$C_6$ (cycloalkyl)(alkyl) or $C_5$-$C_7$ (cycloalkenyl) alkyl;
R$^2$ is H, OH or esters thereof;
R$^3$ is H, alkyl or $C_1$-$C_6$ alkyl-C=O;
R$^4$ and R$^5$ are independently H, halogen, $C_1$-$C_6$ alkyl, $C_1$-$C_4$ alkoxy, nitro, amino, cyano, carboxyl or acyl which may be substituted for one or more hydrogens on the ring;
X$^1$ and X$^2$ are the same or different, and may be H, alkyl, —OR$^6$, —NR$^7$R$^8$R$^9$, —NCOR$^{10}$, —NO$_2$, or —SR$^{11}$, wherein,
R$^6$ and R$^{11}$ are independently H, alkyl, substituted alkyl, cycloalkyl, substituted cycloalkyl, aryl, substituted aryl, acyl, aroyl, polyethyleneglycyl (PEGyl) or a polyether group;
R$^7$, R$^8$ and R$^{10}$ are independently hydrogen, alkyl, substituted alkyl, cycloalkyl, substituted cycloalkyl, aryl, or substituted aryl;
R$^9$ and R$^{12}$ can be present or absent and are independently hydrogen, alkyl, substituted alkyl, cycloalkyl, substituted cycloalkyl, aryl, or substituted aryl or pharmaceutically acceptable salts thereof.

11. A unit dosage according to claim 1, wherein the opioid antagonist is a naloxone analog represented by formula Iα or Iβ:

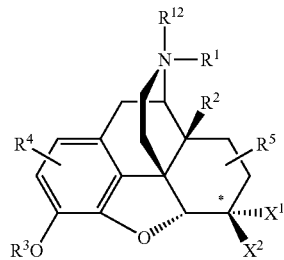

(Iα)

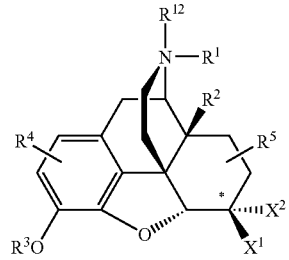

(Iβ)

wherein:
R$^1$ is $C_3$-$C_6$ alkenyl;
R$^2$ is H, OH or esters thereof;

$R^3$ is H, alkyl or $C_1$-$C_6$ alkyl-C=O;

$R^4$ and $R^5$ are independently H, halogen, $C_1$-$C_6$ alkyl, $C_1$-$C_4$ alkoxy, nitro, amino, cyano, carboxyl or acyl which may be substituted for one or more hydrogens on the ring;

$X^1$ and $X^2$ are the same or different, and may be H, alkyl, —$OR^6$, —$NR^7R^8R^9$, —$NCOR^{10}$, —$NO_2$, or —$SR^{11}$, wherein, $R^6$ and $R^{11}$ are independently H, alkyl, substituted alkyl, cycloalkyl, substituted cycloalkyl, aryl, substituted aryl, acyl, aroyl, polyethyleneglycyl (PEGyl) or a polyether group;

$R^7$, $R^8$ and $R^{10}$ are independently hydrogen, alkyl, substituted alkyl, cycloalkyl, substituted cycloalkyl, aryl, or substituted aryl;

$R^9$ and $R^{12}$ can be present or absent and are independently hydrogen, alkyl, substituted alkyl, cycloalkyl, substituted cycloalkyl, aryl, or substituted aryl or pharmaceutically acceptable salts thereof.

12. A unit dosage according to claim 1, wherein the neutral opioid antagonist is selected from the group consisting of 6β-naltrexamide, a pharmaceutically acceptable isomorph thereof, and a pharmaceutically acceptable salt thereof.

13. A unit dosage according to claim 1, wherein the neutral opioid antagonist is selected from the group consisting of 6β-naltrexol, a pharmaceutically acceptable isomorph thereof, and a pharmaceutically acceptable salt thereof.

14. A composition according to claim 1, wherein the neutral opioid antagonist is 6β-naltrexol present in an amount between about 0.008-0.25 mg/kg of body weight of the subject and the opioid agonist is a therapeutically effective amount of hydrocodone.

15. A unit dosage of analgesic composition according to claim 1, wherein the opioid agonist is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, noroxycodone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tilidine and tramadol.

16. A unit dosage of an analgesic composition according to claim 15, such composition being suitable for oral, peroral, intragastric, sublingual, suppository, or intravenous administration.

17. A unit dosage according to claim 16, wherein the neutral opioid antagonist has a blood half-life substantially longer than the blood half-life of the opioid agonist, so that repeated administration of the dosage or administration above a prescribed dosage causes a greater increase in blood concentration of the antagonist than of the agonist, so as to deter diversion, discourage abuse and/or reduce addiction liability to the agonist resulting from such administration.

18. A pharmaceutical composition according to claim 17, wherein the neutral opioid antagonist and/or agonist are suitable for formulation in a slow-release formulation, slow-release co-formulation, or are formulated in a slow-release formulation or co-formulation, either separately or together.

19. A unit dosage according to claim 16, wherein the neutral opioid antagonist and/or agonist are suitable for formulation in a slow-release formulation, slow-release co-formulation, or are formulated in a slow-release formulation or co-formulation, either separately or together.

20. A unit dosage of an analgesic composition comprising:
an opioid agonist in an amount sufficient to confer analgesia in a mammalian subject; and
a neutral opioid antagonist in an amount sufficient to produce nearly complete inhibition of peripheral effects, and insufficient to block substantial central effects, of the opioid agonist in the subject.

21. A unit dosage of an analgesic composition according to claim 20, wherein the subject is a human.

22. A unit dosage of an analgesic composition according to claim 20, wherein the opioid agonist is hydrocodone.

23. A unit dosage according to claim 20 that deters abuse of the opioid agonist, wherein the opioid agonist has a blood half-life; and the neutral opioid antagonist has a blood half-life substantially longer than the blood half-life of the opioid agonist and is also present in an amount effective so that, upon successive administration of the unit dosage, the blood concentration ratio of neutral opioid antagonist to opioid agonist increases with each successive administration until a steady state is reached, as measured in mg per kg of body weight of the subject, and repeated administration of the unit dosage exceeding therapeutically recommended limits results in reduced euphoria and reduced pain relief in the subject so as to deter abuse.

24. A unit dosage according to claim 20, wherein the opioid antagonist is a naltrexone analog represented by formula Iα or Iβ:

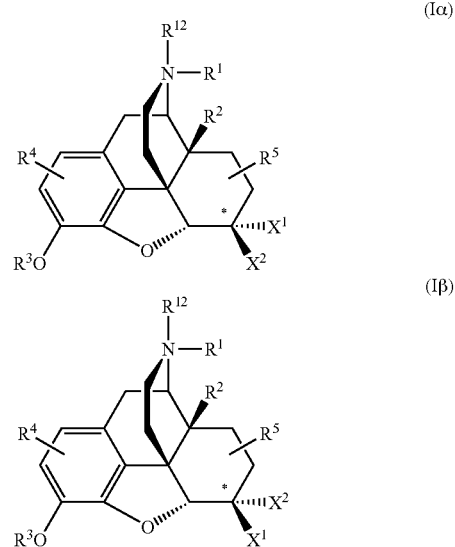

wherein:
$R^1$ is $C_3$-$C_6$ (cycloalkyl)(alkyl) or $C_5$-$C_7$ (cycloalkenyl) alkyl;
$R^2$ is H, OH or esters thereof;
$R^3$ is H, alkyl or $C_1$-$C_6$ alkyl-C=O;
$R^4$ and $R^5$ are independently H, halogen, $C_1$-$C_6$ alkyl, $C_1$-$C_4$ alkoxy, nitro, amino, cyano, carboxyl or acyl which may be substituted for one or more hydrogens on the ring;

$X^1$ and $X^2$ are the same or different, and may be H, alkyl, —$OR_6$, —$NR^7R^8R^9$, —$NCOR^{10}$, —$NO_2$, or —$SR^{11}$, wherein, $R^6$ and $R^{11}$ are independently H, alkyl, substituted alkyl, cycloalkyl, substituted cycloalkyl, aryl, substituted aryl, acyl, aroyl, polyethyleneglycyl (PEGyl) or a polyether group;

$R^7$, $R^8$ and $R^{10}$ are independently hydrogen, alkyl, substituted alkyl, cycloalkyl, substituted cycloalkyl, aryl, or substituted aryl;

$R^9$ and $R^{12}$ can be present or absent and are independently hydrogen, alkyl, substituted alkyl, cycloalkyl, substituted cycloalkyl, aryl, or substituted aryl or pharmaceutically acceptable salts thereof.

25. A unit dosage according to claim 20, wherein the opioid antagonist is a naloxone analog represented by formula Iα or Iβ:

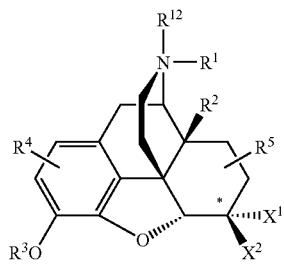

(Iα)

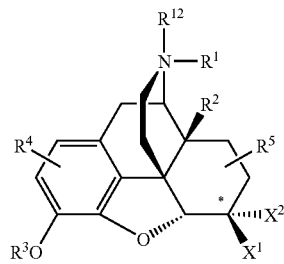

(Iβ)

wherein:

$R^1$ is $C_3$-$C_6$ alkenyl;

$R^2$ is H, OH or esters thereof;

$R^3$ is H, alkyl or $C_1$-$C_6$ alkyl-C=O;

$R^4$ and $R^5$ are independently H, halogen, $C_1$-$C_6$ alkyl, $C_1$-$C_4$ alkoxy, nitro, amino, cyano, carboxyl or acyl which may be substituted for one or more hydrogens on the ring;

$X^1$ and $X^2$ are the same or different, and may be H, alkyl, —$OR^6$, —$NR^7R^8R^9$, —$NCOR^{10}$, —$NO_2$, or —$SR^{11}$, wherein, $R^6$ and $R^{11}$ are independently H, alkyl, substituted alkyl, cycloalkyl, substituted cycloalkyl, aryl, substituted aryl, acyl, aroyl, polyethyleneglycyl (PEGyl) or a polyether group;

$R^7$, $R^8$ and $R^{10}$ are independently hydrogen, alkyl, substituted alkyl, cycloalkyl, substituted cycloalkyl, aryl, or substituted aryl;

$R^9$ and $R^{12}$ can be present or absent and are independently hydrogen, alkyl, substituted alkyl, cycloalkyl, substituted cycloalkyl, aryl, or substituted aryl or pharmaceutically acceptable salts thereof.

26. A unit dosage according to claim 20, wherein the neutral opioid antagonist is selected from the group consisting of 6β-naltrexamide, a pharmaceutically acceptable isomorph thereof, and a pharmaceutically acceptable salt thereof.

27. A unit dosage according to claim 20, wherein the neutral opioid antagonist is selected from the group consisting of 6β-naltrexol, a pharmaceutically acceptable isomorph thereof, and a pharmaceutically acceptable salt thereof.

28. A composition according to claim 20, wherein the neutral opioid antagonist is 6β-naltrexol present in an amount between about 0.008-0.25 mg/kg of body weight of the subject and the opioid agonist is a therapeutically effective amount of hydrocodone.

\* \* \* \* \*

UNITED STATES PATENT AND TRADEMARK OFFICE
CERTIFICATE OF CORRECTION

PATENT NO.         : 8,883,817 B2                                Page 1 of 1
APPLICATION NO.    : 12/288347
DATED              : November 11, 2014
INVENTOR(S)        : Wolfgang Sadée et al.

It is certified that error appears in the above-identified patent and that said Letters Patent is hereby corrected as shown below:

IN THE CLAIMS

In Col. 29, line 7
replace "papavereturn"
with "papaveretum"

In Col. 31, line 49
replace "papavereturn"
with "papaveretum"

In Col. 33, line 2
replace "$OR_6$"
with "$OR^6$"

Signed and Sealed this
Fifteenth Day of March, 2016

Michelle K. Lee
*Director of the United States Patent and Trademark Office*